(12) United States Patent
Tehrani et al.

(10) Patent No.: US 8,140,164 B2
(45) Date of Patent: Mar. 20, 2012

(54) THERAPEUTIC DIAPHRAGM STIMULATION DEVICE AND METHOD

(75) Inventors: Amir J. Tehrani, San Francisco, CA (US); Rose Province, San Jose, CA (US); Alan Schwartz, Baltimore, MD (US); David Hillman, West Australia (AU); Peter Eastwood, West Australia (AU); David Ligon, San Francisco, CA (US); Chang Lee, Redwood City, CA (US); Drew Hoffmann, Portola Valley, CA (US); Amy Michelle Goodman, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 327 days.

(21) Appl. No.: 11/981,342

(22) Filed: Oct. 31, 2007

(65) Prior Publication Data

US 2008/0167695 A1     Jul. 10, 2008

Related U.S. Application Data

(63) Continuation-in-part of application No. 11/480,074, filed on Jun. 29, 2006, which is a continuation-in-part of application No. 11/271,726, filed on Nov. 10, 2005, now Pat. No. 7,970,475, which is a continuation-in-part of application No. 10/966,484, filed on Oct. 15, 2004, now abandoned, and a continuation-in-part of application No. 10/966,474, filed on Oct. 15, 2004, and a continuation-in-part of application No. 10/966,421, filed on Oct. 15, 2004, and a continuation-in-part of application No. 10/966,472, filed on Oct. 15, 2004, which is a continuation-in-part of application No. 10/686,891, filed on Oct. 15, 2003.

(51) Int. Cl.
*A61N 1/36* (2006.01)

(52) U.S. Cl. .......................................... 607/42

(58) Field of Classification Search .................... 607/42; 600/529
See application file for complete search history.

(56) References Cited

U.S. PATENT DOCUMENTS

| | | | |
|---|---|---|---|
| 4,827,935 A | 5/1989 | Geddes et al. | |
| 4,830,008 A * | 5/1989 | Meer | 607/42 |
| 5,056,519 A | 10/1991 | Vince | |
| 5,146,918 A | 9/1992 | Kallok et al. | |
| 5,174,287 A | 12/1992 | Kallok et al. | |

(Continued)

FOREIGN PATENT DOCUMENTS

WO    WO 1986/000234    1/1986

OTHER PUBLICATIONS

Aiyar, H. et al, "Laparoscopic Implant Instrument for the Placement of Intramuscular Electrodes in the Diaphragm," *Transactions on Rehabilitation Engineering*, pp. 360-371, Sep. 1999.

(Continued)

*Primary Examiner* — Niketa Patel
*Assistant Examiner* — Alyssa M Alter
(74) *Attorney, Agent, or Firm* — Levine Bagade Han LLP

(57) ABSTRACT

A device and method for treating a variety of conditions, disorders or diseases with diaphragm/phrenic nerve stimulation is provided.

18 Claims, 23 Drawing Sheets

U.S. PATENT DOCUMENTS

| | | | |
|---|---|---|---|
| 5,190,036 A | 3/1993 | Linder | |
| 5,211,173 A | 5/1993 | Kallok et al. | |
| 5,215,082 A | 6/1993 | Kallok et al. | |
| 5,233,983 A | 8/1993 | Markowitz | |
| 5,265,604 A | 11/1993 | Vince | |
| 5,281,219 A | 1/1994 | Kallok | |
| 5,300,094 A | 4/1994 | Kallok et al. | |
| 5,423,327 A | 6/1995 | Clauson et al. | |
| 5,423,372 A | 6/1995 | Kearney | |
| 5,483,969 A | 1/1996 | Testerman et al. | |
| 5,485,851 A | 1/1996 | Erickson | |
| 5,522,862 A | 6/1996 | Testerman et al. | |
| 5,524,632 A | 6/1996 | Stein et al. | |
| 5,540,731 A | 7/1996 | Testerman | |
| 5,540,732 A | 7/1996 | Testerman | |
| 5,540,733 A | 7/1996 | Testerman et al. | |
| 5,546,952 A | 8/1996 | Erickson | |
| 5,549,655 A | 8/1996 | Erickson | |
| 5,572,543 A | 11/1996 | Heinemann et al. | |
| 5,678,535 A | 10/1997 | DiMarco | |
| 5,766,228 A | 6/1998 | Bonnet et al. | |
| 5,797,923 A | 8/1998 | Aiyar et al. | |
| 5,800,470 A | 9/1998 | Stein et al. | |
| 5,814,086 A | 9/1998 | Hirschberg et al. | |
| 5,830,008 A | 11/1998 | Broschard, III | |
| 5,876,353 A | 3/1999 | Riff | |
| 5,895,360 A | 4/1999 | Christopherson et al. | |
| 5,911,218 A | 6/1999 | DiMarco | |
| 5,944,680 A | 8/1999 | Christopherson et al. | |
| 6,021,352 A | 2/2000 | Christopherson et al. | |
| 6,099,479 A | 8/2000 | Christopherson et al. | |
| 6,212,435 B1 | 4/2001 | Lattner et al. | |
| 6,224,562 B1 | 5/2001 | Lurie et al. | |
| 6,251,126 B1 | 6/2001 | Ottenhoff et al. | |
| 6,269,269 B1 | 7/2001 | Ottenhoff et al. | |
| 6,312,399 B1 | 11/2001 | Lurie et al. | |
| 6,314,324 B1 | 11/2001 | Lattner et al. | |
| 6,345,202 B2 | 2/2002 | Richmond et al. | |
| 6,415,183 B1 * | 7/2002 | Scheiner et al. | 607/42 |
| 6,463,327 B1 | 10/2002 | Lurie et al. | |
| 6,480,733 B1 | 11/2002 | Turcott | |
| 6,489,447 B1 | 12/2002 | Basey et al. | |
| 6,512,949 B1 | 1/2003 | Combs et al. | |
| 6,527,729 B1 | 3/2003 | Turcott | |
| 6,542,774 B2 | 4/2003 | Hill et al. | |
| 6,572,543 B1 | 6/2003 | Christopherson et al. | |
| 6,574,507 B1 | 6/2003 | Bonnet | |
| 6,587,726 B2 | 7/2003 | Lurie et al. | |
| 6,589,188 B1 | 7/2003 | Street et al. | |
| 6,600,949 B1 | 7/2003 | Turcott | |
| 6,633,779 B1 | 10/2003 | Schuler et al. | |
| 6,651,652 B1 | 11/2003 | Ward | |
| 6,731,984 B2 | 5/2004 | Cho et al. | |
| 6,735,479 B2 | 5/2004 | Fabian et al. | |
| 6,752,765 B1 | 6/2004 | Jensen et al. | |
| 6,811,537 B2 | 11/2004 | Bardy | |
| 6,830,548 B2 | 12/2004 | Bonnet et al. | |
| 6,881,192 B1 | 4/2005 | Park | |
| 6,908,437 B2 | 6/2005 | Bardy | |
| 7,058,453 B2 | 6/2006 | Nelson et al. | |
| 7,070,568 B1 | 7/2006 | Koh et al. | |
| 7,082,331 B1 | 7/2006 | Park et al. | |
| 7,117,032 B2 | 10/2006 | Childre et al. | |
| 7,277,757 B2 | 10/2007 | Casavant et al. | |
| 7,532,934 B2 | 5/2009 | Lee et al. | |
| 7,840,270 B2 | 11/2010 | Ignagni et al. | |
| 2002/0049482 A1 | 4/2002 | Fabian et al. | |
| 2002/0193697 A1 | 12/2002 | Cho et al. | |
| 2002/0193839 A1 | 12/2002 | Cho et al. | |
| 2003/0127091 A1 | 7/2003 | Chang | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0195571 A1 | 10/2003 | Burnes et al. | |
| 2003/0204213 A1 | 10/2003 | Jensen et al. | |
| 2003/0225339 A1 | 12/2003 | Orr et al. | |
| 2004/0059240 A1 | 3/2004 | Cho et al. | |
| 2004/0077953 A1 | 4/2004 | Turcott | |
| 2004/0088015 A1 | 5/2004 | Casavant et al. | |
| 2004/0111040 A1 | 6/2004 | Ni et al. | |
| 2004/0122484 A1 | 6/2004 | Hatlestad et al. | |
| 2004/0134496 A1 | 7/2004 | Cho et al. | |
| 2004/0138719 A1 | 7/2004 | Cho et al. | |
| 2004/0176809 A1 | 9/2004 | Cho et al. | |
| 2004/0199221 A1 | 10/2004 | Fabian et al. | |
| 2004/0225226 A1 | 11/2004 | Lehrman et al. | |
| 2004/0237963 A1 | 12/2004 | Berthon-Jones | |
| 2005/0021102 A1 | 1/2005 | Ignagni et al. | |
| 2005/0039745 A1 | 2/2005 | Stahmann et al. | |
| 2005/0043644 A1 | 2/2005 | Stahmann et al. | |
| 2005/0043772 A1 | 2/2005 | Stahmann et al. | |
| 2005/0055060 A1 | 3/2005 | Koh et al. | |
| 2005/0061315 A1 | 3/2005 | Lee et al. | |
| 2005/0061319 A1 | 3/2005 | Hartley et al. | |
| 2005/0061320 A1 | 3/2005 | Lee et al. | |
| 2005/0065563 A1 | 3/2005 | Scheiner | |
| 2005/0065567 A1 | 3/2005 | Lee et al. | |
| 2005/0074741 A1 | 4/2005 | Lee et al. | |
| 2005/0076909 A1 | 4/2005 | Stahmann et al. | |
| 2005/0080461 A1 | 4/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0101833 A1 | 5/2005 | Hsu et al. | |
| 2005/0107860 A1 | 5/2005 | Ignagni et al. | |
| 2005/0115561 A1 | 6/2005 | Stahmann et al. | |
| 2005/0119711 A1 | 6/2005 | Cho et al. | |
| 2005/0145246 A1 | 7/2005 | Hartley et al. | |
| 2005/0148897 A1 | 7/2005 | Cho et al. | |
| 2005/0165457 A1 | 7/2005 | Benser et al. | |
| 2005/0224076 A1 | 10/2005 | Pflichner et al. | |
| 2005/0240240 A1 | 10/2005 | Park et al. | |
| 2005/0261600 A1 | 11/2005 | Aylsworth | |
| 2005/0261747 A1 | 11/2005 | Schuler et al. | |
| 2006/0030894 A1 | 2/2006 | Tehrani | |
| 2006/0036294 A1 | 2/2006 | Tehrani | |
| 2006/0058852 A1 | 3/2006 | Koh et al. | |
| 2006/0064030 A1 | 3/2006 | Cosentino et al. | |
| 2006/0064325 A1 | 3/2006 | Matsumoto et al. | |
| 2006/0122622 A1 | 6/2006 | Truckai et al. | |
| 2006/0122661 A1 | 6/2006 | Mandell | |
| 2006/0122662 A1 | 6/2006 | Tehrani | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0224211 A1 | 10/2006 | Durand et al. | |
| 2006/0247729 A1 | 11/2006 | Tehrani et al. | |
| 2006/0282131 A1 | 12/2006 | Caparso et al. | |
| 2007/0021795 A1 | 1/2007 | Tehrani | |
| 2008/0177347 A1 | 7/2008 | Tehrani et al. | |
| 2008/0188903 A1 | 8/2008 | Tehrani et al. | |

OTHER PUBLICATIONS

Bernardi, L. et al, "Effect of Rosary Prayer and Yoga Mantras on Autonomic Cardiovascular Rhythms: Comparative Study," *BMJ*, 323:22-29, Dec. 2001.

Bernardi, L. et al, "Slow Breathing Increases Arterial Baroreflex sensitivity in Patients with Chronic Heart Failure," *Circulation*, 105; 143-145, 2002, *American Heart Association*.

DiMarco, A. F. et al, "Phrenic Nerve Pacing in a Tetraplegic Patient via Intramuscular Diaphragm Electrodes," *American Journal of Respiratory and Critical Care Medicine*, 144:1604-1606, 2002.

Glenn, W. W. L., "Diaphragm Pacing: Present Status," *PACE*, 1: 357-370, Jul.-Sep. 1978.

Gosselink, R. "Controlled Breathing and Dyspnea in Patients With Chronic Obstructive Pulmonary Disease," *Journal of Rehabilitaiton Research and Development*, 40(5):20-31, Supplement 2, Sep./Oct. 2003.

Harish, A. et al, "Laparoscopic Implant Device for Intramuscular Electrodes," *IEEE-EMBC and CMBCC*, pp. 1167-1168, 1995.

Iazzo, P. ed., "Handbook of Cardiac Anatomy, Physiology, and Devices", p. 398, 2009.
Jensen, A. et al, "Signal Transduction in Smooth Muscle: Airway caliber in healthy and asthmatic subjects effects of bronchial challenge and deep inspirations," *J. Appl Physiol*, 91:506-515, 2001.
Liem, L.B., "EP 101: Ventricular Tachycardia", EP Lab Digest, v.7, No. 8, Aug. 2007.
Malkin R. et al., "The Effect of Inducing Ventricular Fibrillation with 50-Hz Pacing Versus T are Stimulation on the Ability to Defibrillate", Pacing and Clinical Electrophysiology, vol. 21, issue 5, May 1998.
Mitsuyana, T. et al, "Diaphragm Pacing With the Spinal Cord Stimulator," *Aeta Neurochir*, 87:89-92, 2003.
Noshiro, M. et al., "Method of Electrophrenic Respiration for Producing a Natural Respiratory Flow Rate Using Feedback Control of Tidal Volume Waveform," *Med. & Bio. Eng. & Comput.*, 20:765-71, Nov. 1982.
Patroniti, M.D., et al "Sigh Improves Gas Exchange and Lung Volume In Patients with Acute Respiratory Distress Syndrome Undergoing Pressure Support Ventilation," *Anesthesiology*,96:788-794, 2002.
Reeve, C., "New Implantable Breathing Device," University Hospitals of Cleveland, pp. 1-4, 2003.
Reeve, C., Christopher Reeve Paralysis Foundation Questions & Answers, pp. 1-3, Mar. 13, 2003.
Sauermann, S. et al, "Computer Aided Adjustment of the Phrenic Pacemaker: Automatic Functions. Documentation, and Quality Control," *Artificial Organs*, 21(3):216-217, 1997.
Schmit, B. D. et al, "Laparoscopic Placement of Electrodes for Diaphragm Pacing Using Stimulation to Locate the Phrenic Nerve Motor Points," *Transactions on Rehabilitation Engineering*, 6(4):382-390, Dec. 1998.
Schmit, B.D. et al, "An Implantable Impedance Pneumograph Monitor for Detection of Diaphragm Contraction and Airway Obstruction During Diaphragm Pacing," *Medical & Biological Engineering & Computing*, 37:162-168, 1999.
Series, F. et al, "Increasing the Functional Residual Capacity May Reverse Obstructive Sleep Apnea Sleep," 11(4):349-353, 1988.
Shaul, D.B. et al, "Thoracoscopic Placement of Phrenic Nerve Electrodes for Diaphragmatic Pacing in Children," *Journal of Pediatric Surgery*, 37:974-978, Jul. 2002.
Shier, D. et al, *Hole's Human Anatomy & Physiology*,pp. 798 (2 pages total).
Simon, P. et al, "Vagal Feedback in the Entrainment of Respiration to Mechanical Ventilation in Sleeping Humans," *J. App. Physiol*, 89:760769, 2000.
Sin, D. "Effects of Continuous Positive Airway Pressure on Cardiovascular Outcomes in Heart Failure Patients With and Without Cheyne-Stokes Respiration," *Circulation*, 102:61-66, Jul. 4, 2000.
Taira, T. et al, "Phrenic Nerve Stimulation for Diaphragm Pacing With a Spinal Cord Stimulator," *Surg Neurol*. 59:128-132, 2003.
U.S. Appl. No. 10/686,891, filed Oct. 15, 2003 in the name of Tehrani, final Office Action mailed Sep. 15, 2010.
U.S. Appl. No. 10/686,891, filed Oct. 15, 2003 in the name of Tehrani, non-final Office Action mailed Sep. 18, 2009.
U.S. Appl. No. 10/966,421, filed Oct. 15, 2004 in the name of Tehrani, Final Office Action mailed Oct. 26, 2009.
U.S. Appl. No. 10/966,421, filed Oct. 15, 2004 in the name of Tehrani, non-final Office Action mailed Jun. 9, 2010.
U.S. Appl, No. 10/966,472, filed Oct. 15, 2004 in the name of Tehrani et al., non-final Office Action mailed Feb. 23, 2010.
U.S. Appl. No. 10/966,474, filed Oct. 15, 2004 in the name of Tehrani, Final Office Action mailed Jan. 21, 2010.
U.S. Appl. No. 11/246,439, filed Oct. 11, 2005 in the name of Tehrani, final Office Action mailed Jun. 29, 2010.
U.S. Appl. No. 11/246,439, filed Oct. 11, 2005 in the name of Tehrani, non-final Office Action mailed Sep. 30, 2009.
U.S. Appl. No. 11/249,718, filed Oct. 13, 2005 in the name of Tehrani, final Office Action mailed Apr. 1, 2009.
U.S. Appl. No. 11/249,718, filed Oct. 13, 2005 in the name of Tehrani, final Office Action mailed Sep. 14, 2010.
U.S. Appl. No. 11/249,718, filed Oct. 13, 2005 in the name of Tehrani, non-final Office Action mailed Apr. 18, 2008.
U.S. Appl. No. 11/249,718, filed Oct. 13, 2005 in the name of Tehrani, non-final Office Action mailed Nov. 25, 2009.
U.S. Appl. No. 11/271,264, filed Nov. 10, 2005 in the name of Tehrani et al., non-final Office Action mailed Mar. 30, 2010.
U.S. Appl. No. 11/271,315, filed Nov. 10, 2005 in the name of Tehrani et al., Final Office Action mailed Mar. 31, 2010.
U.S. Appl. No. 11/271,315, filed Nov. 10, 2005 in the name of Tehrani et al., non-final Office Action mailed Oct. 3, 2008.
U.S. Appl. No. 11/271,554, filed Nov. 10, 2005 in the name of Tehrani et al., final Office Action mailed Jan. 31, 2011.
U.S. Appl. No. 11/271,554, filed Nov. 10, 2005 in the name of Tehrani et al., non-final Office Action mailed Dec. 24, 2009.
U.S. Appl. No. 11/271,726, filed Nov. 10, 2005 in the name of Tehrani et al., non-final Office Action mailed Mar. 31, 2010.
U.S. Appl. No. 11/480,074, filed Jun. 29, 2006 in the name of Tehrani et al., Final Office Action mailed Apr. 30, 2010.
U.S. Appl. No. 11/526,949, filed Sep. 25, 2006 in the name of Tehrani, final Office Action mailed Mar. 19, 2010.
U.S. Appl. No. 11/526,949, filed Sep. 25, 2006 in the name of Tehrani, non-final Office Action mailed Oct. 5, 2010.
U.S. Appl. No. 11/981,800, filed Oct. 31, 2007 in the name of Tehrani et al., final Office Action mailed Jan. 20, 2011.
U.S. Appl. No. 11/981,800, filed Oct. 31, 2007 in the name of Tehrani et al., non-final Office Action mailed Oct. 7, 2009.
U.S. Appl. No. 11/981,831, filed Oct. 31, 2007 in the name of Tehrani et al., non-final Office Action mailed Jan. 6, 2010.
U.S. Appl. No. 12/080,133, filed Apr. 1, 2008 in the name of Tehrani et al., non-final Office Action mailed Jun. 10, 2010.
U.S. Appl. No. 10/966,421, filed Apr. 8, 2008 in the name of Tehrani, final Office Action mailed Feb. 17, 2011.
U.S. Appl. No. 11/480,074, filed Jun. 29, 2006 in the name of Tehrani et al., non-final Office Action mailed Mar. 16, 2011.
U.S. Appl. No. 10/686,891, filed Oct. 15, 2003 in the name of Tehrani , non-final Office Action mailed Mar. 30, 2011.
U.S. Appl. No. 11/981,727, filed Oct. 31, 2007 in the name of Tehrani et al., non-final Office Action mailed Apr. 4, 2011.
U.S. Appl. No. 11/249,718, filed Oct. 13, 2005 in the name of Tehrani, non-final Office Action mailed Apr. 1, 2011.
U.S. Appl. No. 11/271,726, filed Nov. 10, 2005 in the name of Tehrani et al., non-final Office Action mailed Apr. 4, 2011.
U.S. Appl. No. 10/966,474, filed Oct. 15, 2004 in the name of Tehrani et al., non-final Office Action mailed Mar. 30, 2011.
U.S. Appl. No. 11/271,726, filed Nov. 10, 2005 in the name of Tehrani et al., Notice of Allowance mailed May 18, 2011.
U.S. Appl. No. 11/271,264, filed Nov. 10, 2005 in the name of Tehrani et al., Notice of Allowance mailed May 20, 2011.
Viasys Healthcare, "Ventilation Requires Perfect Balance", *SensorMedics® 3100A HFOV*, Viasys Healthcare Brochure, 2 pages.
Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.
DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.
Dunn, R., "Diaphragm and Accessory Respiratory Muscle Stimulation Using Intramuscular Electrodes" *Arch Phys Med Rehabil*, vol. (76), pp. 266-271, 1995.
Glenn, W., et al. "Diaphragm Pacing" *Journal of Thoracic and Cardiovascular Surgery*, vol. (75):2, pp. 273-281, 1978.

\* cited by examiner

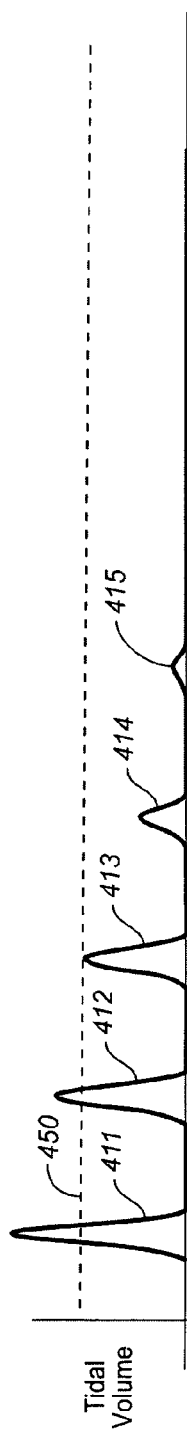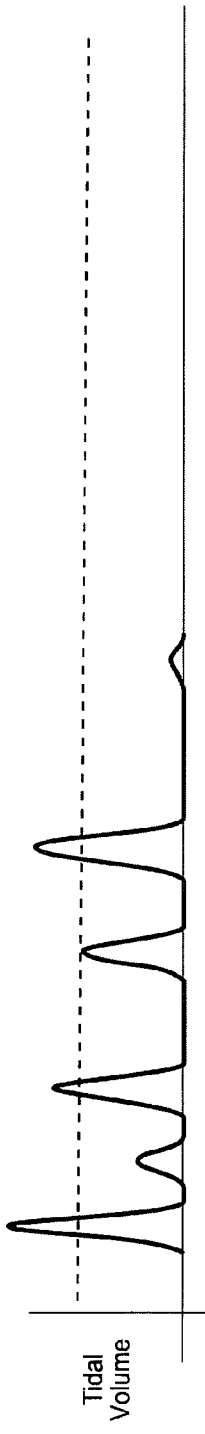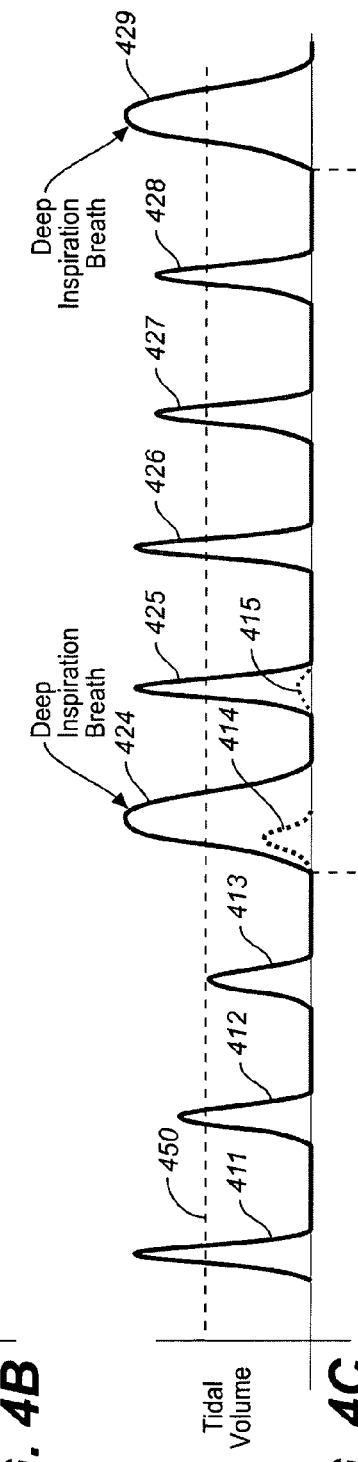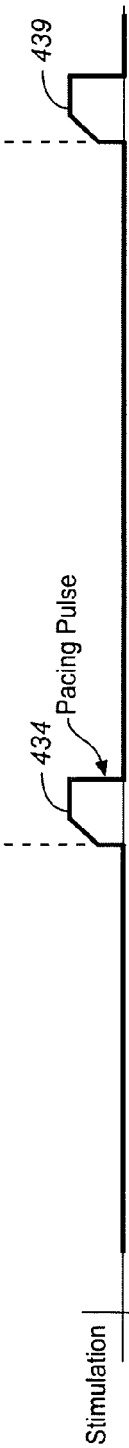

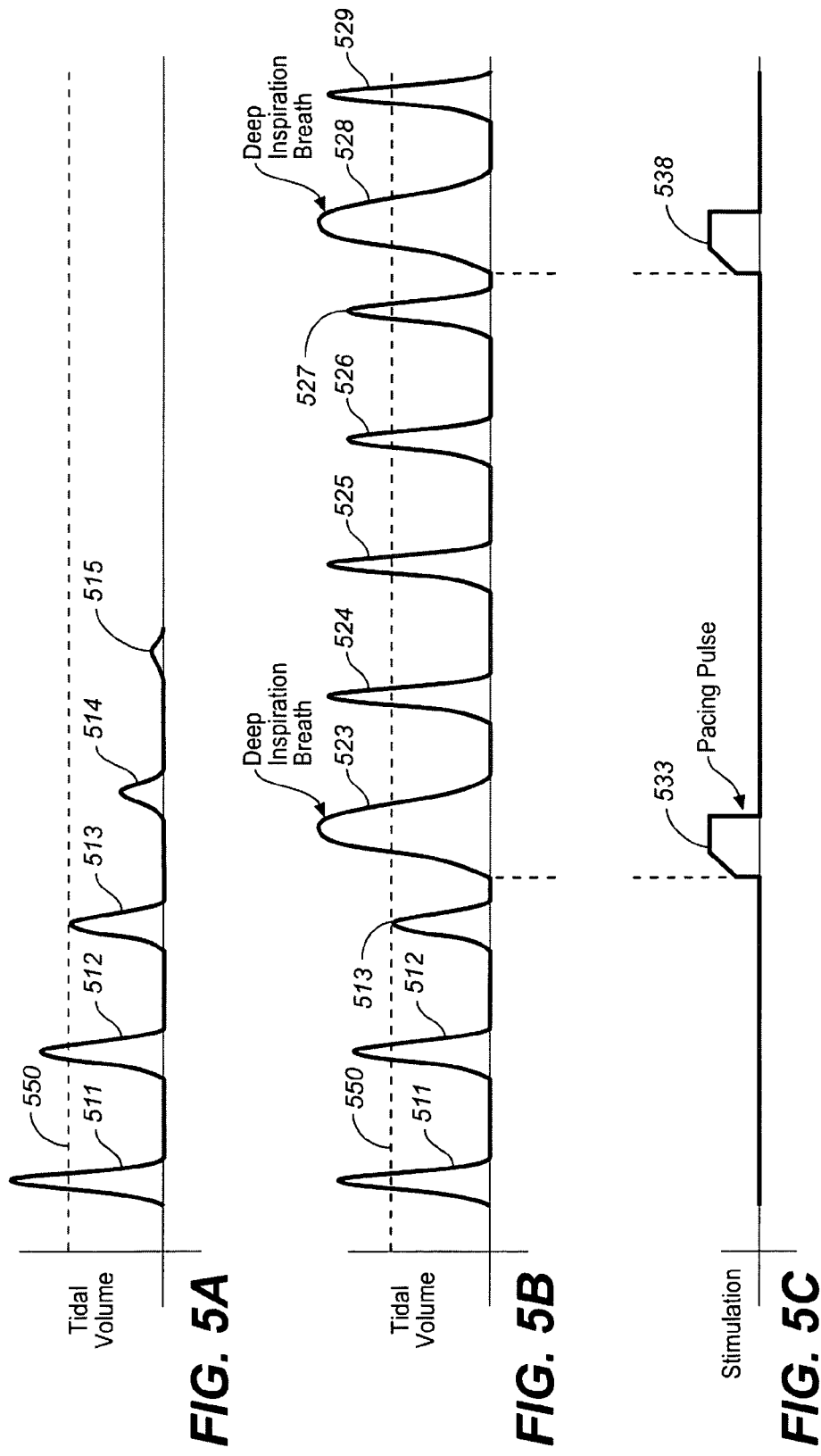

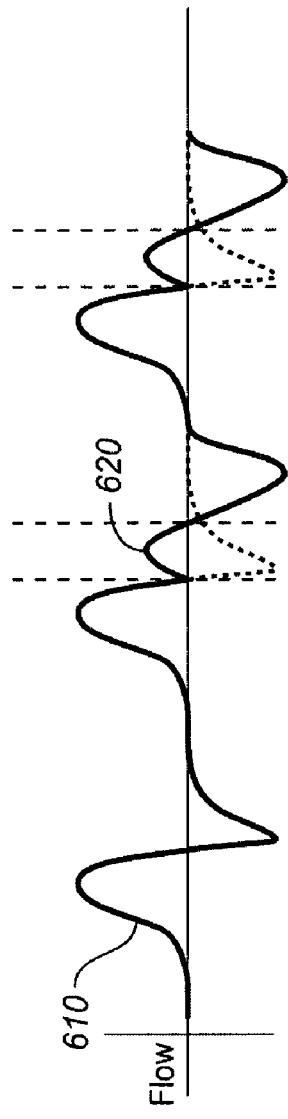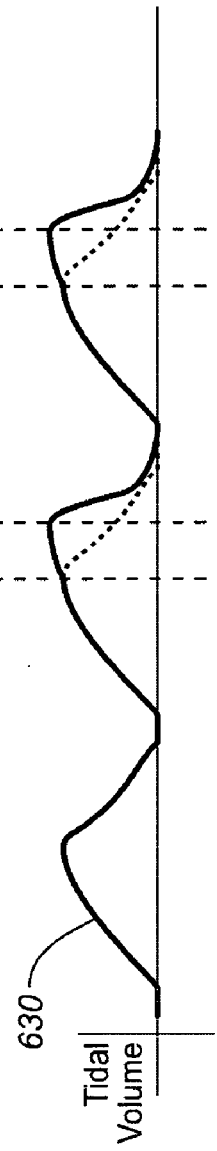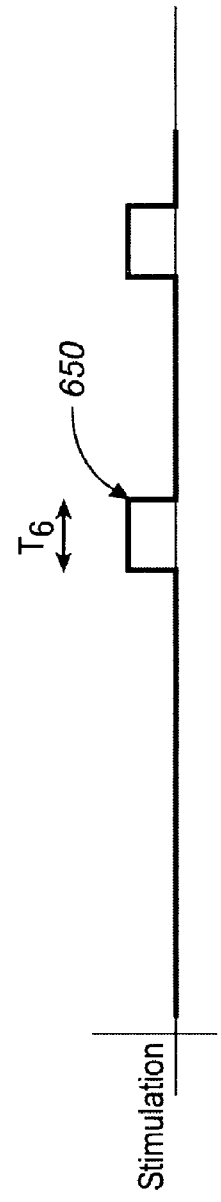

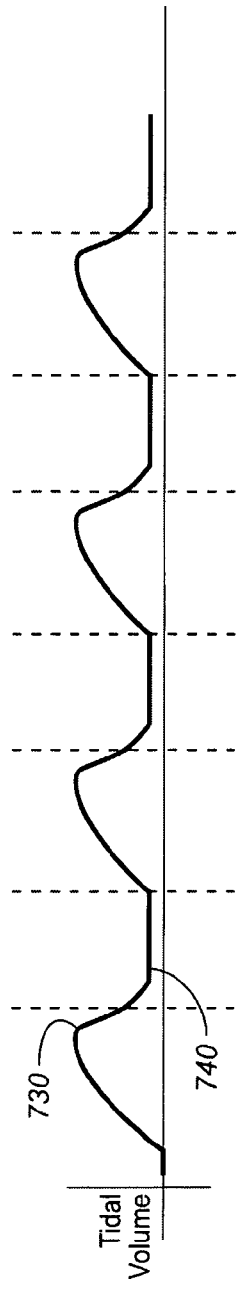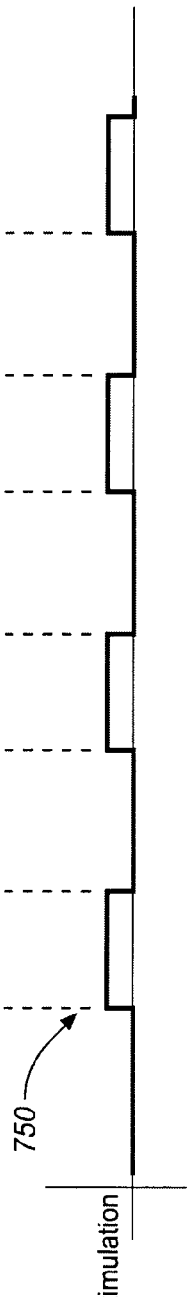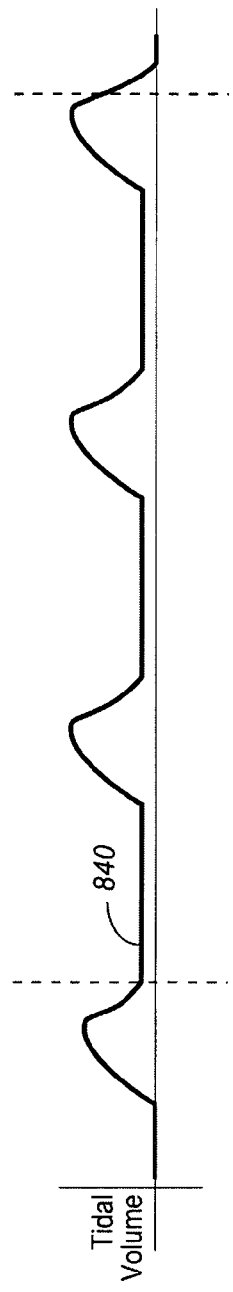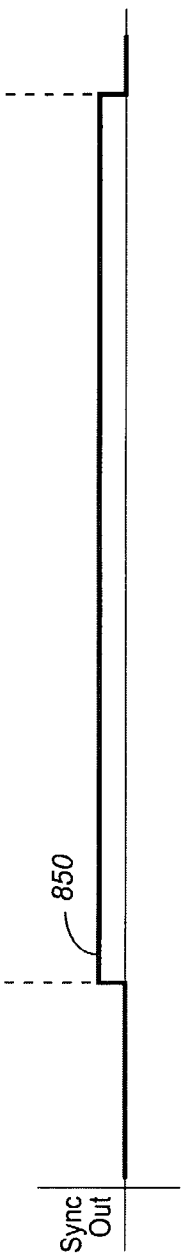
FIG. 7A
FIG. 7B
FIG. 8A
FIG. 8B

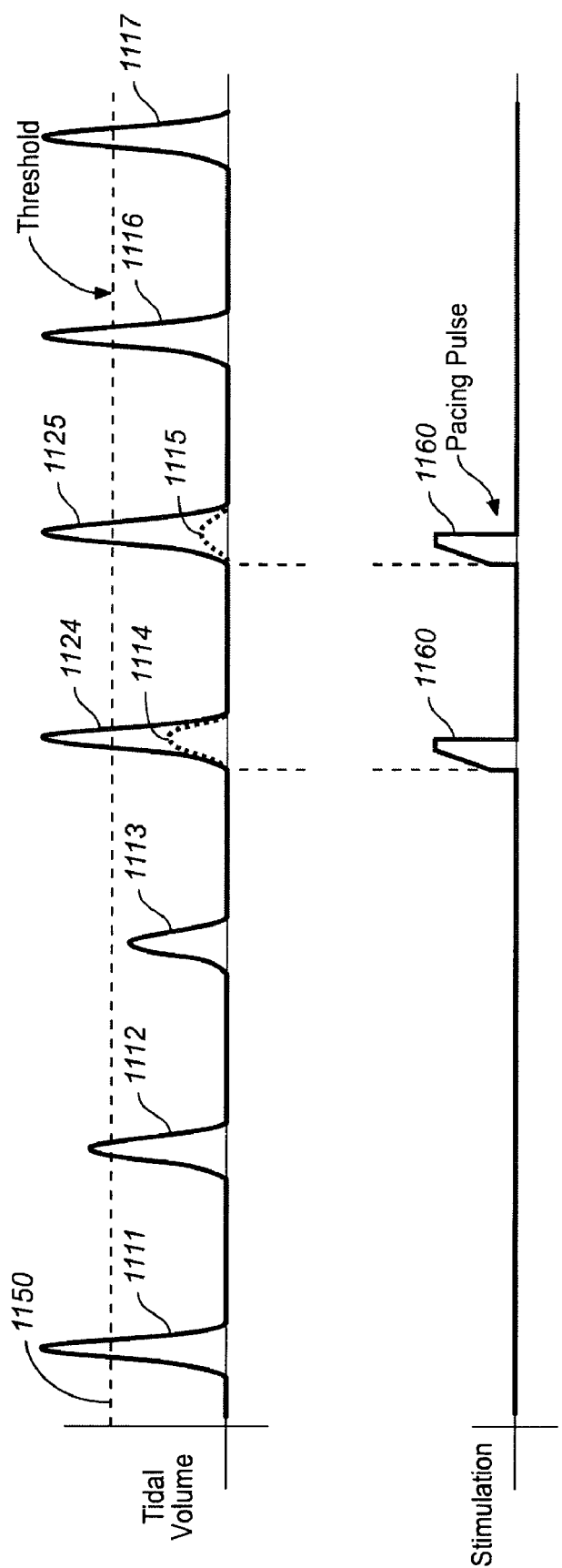

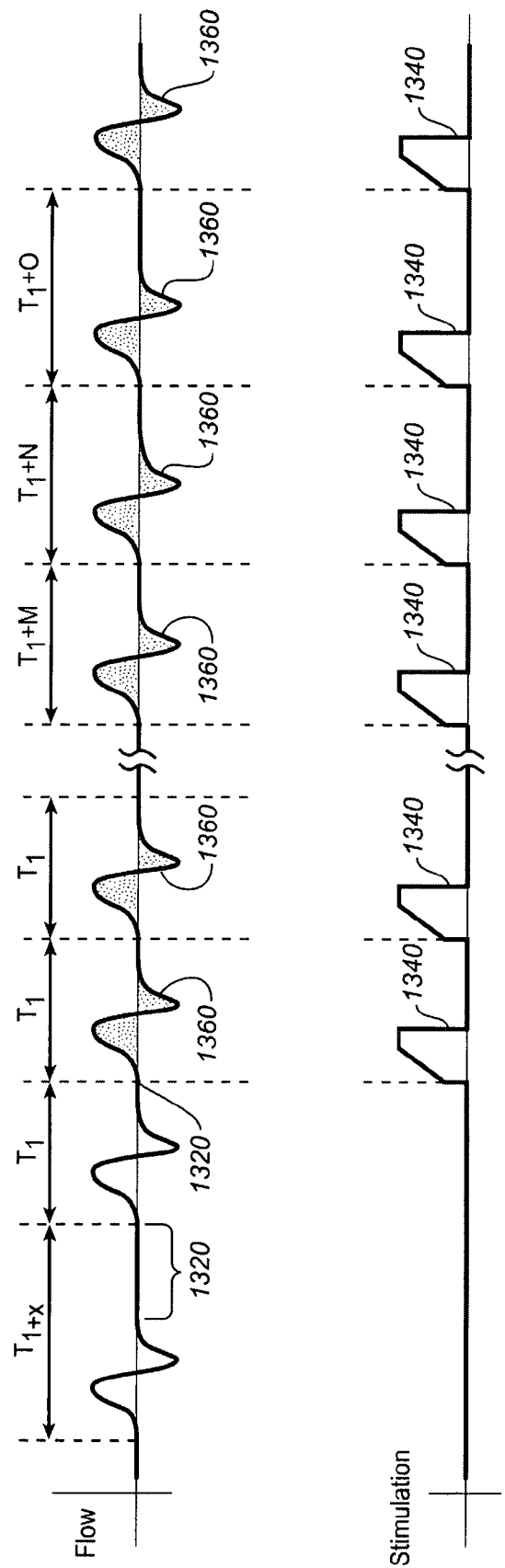

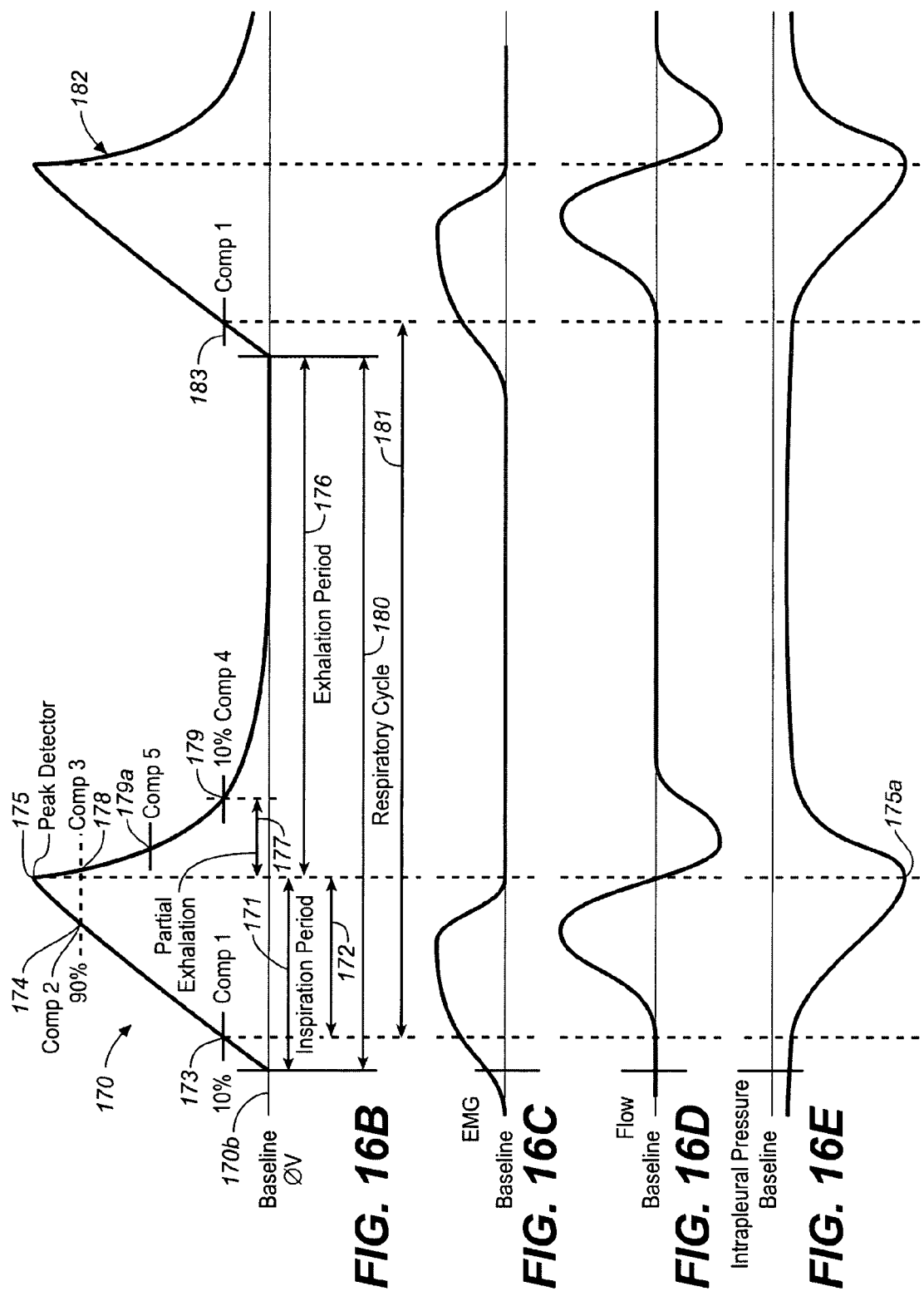

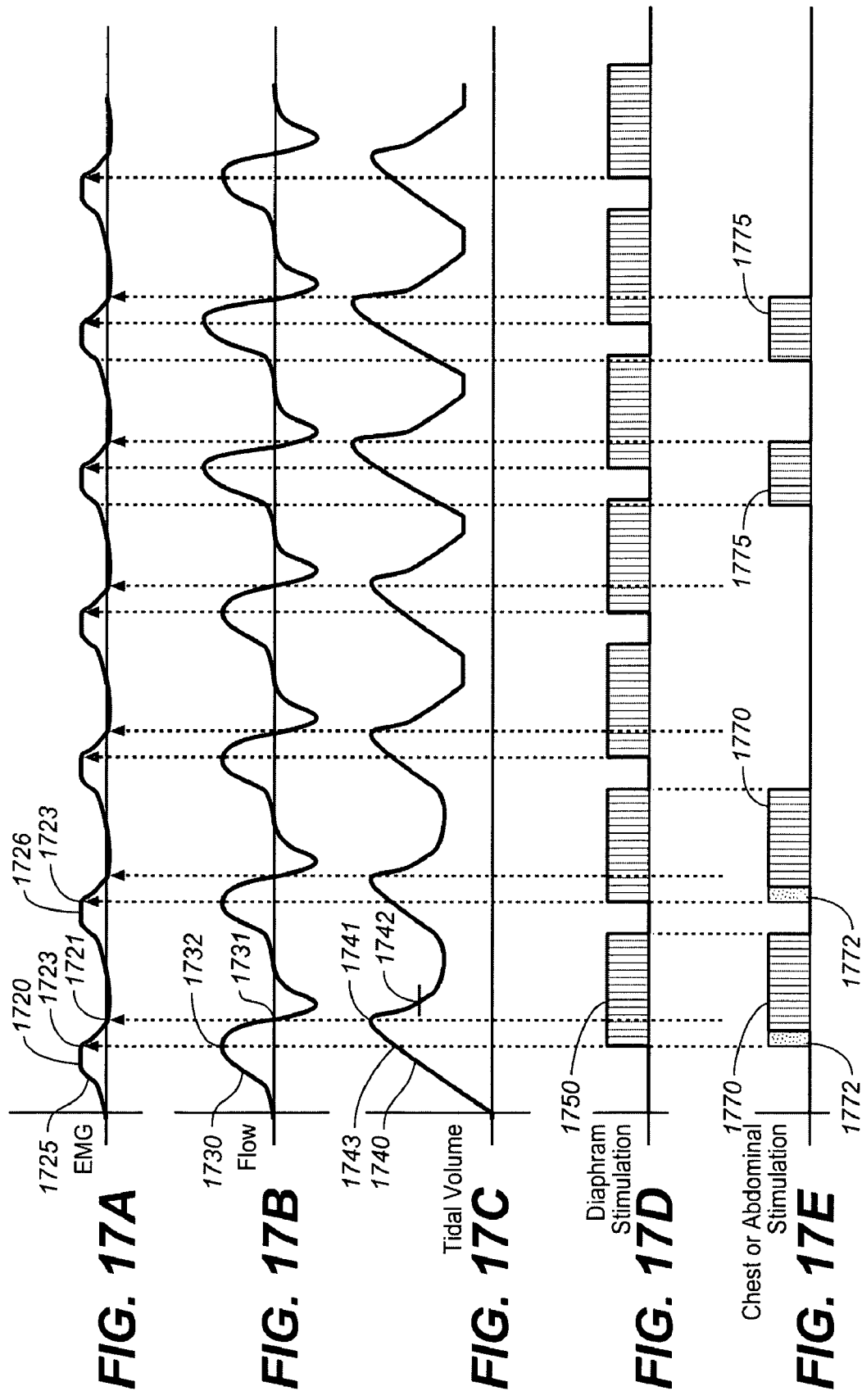

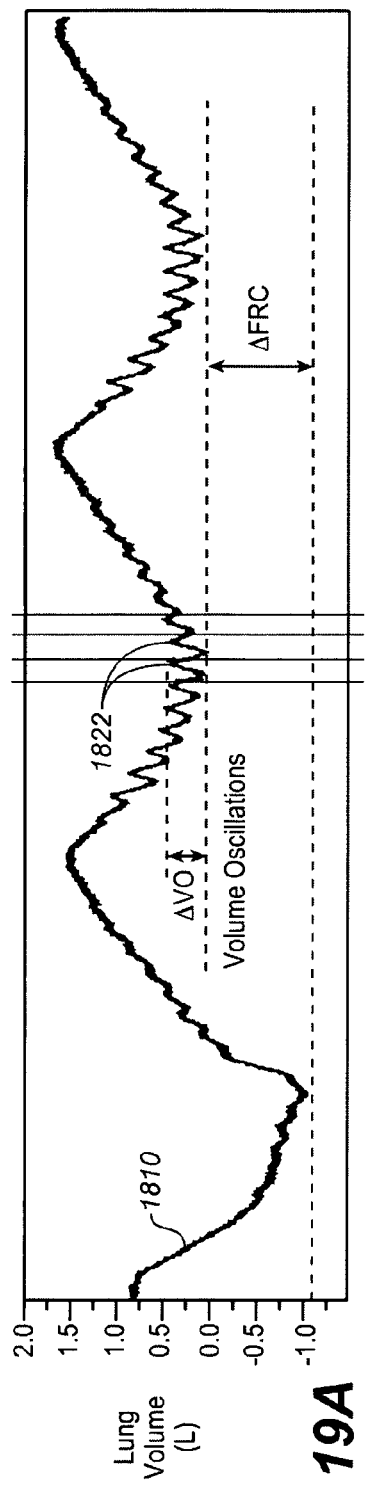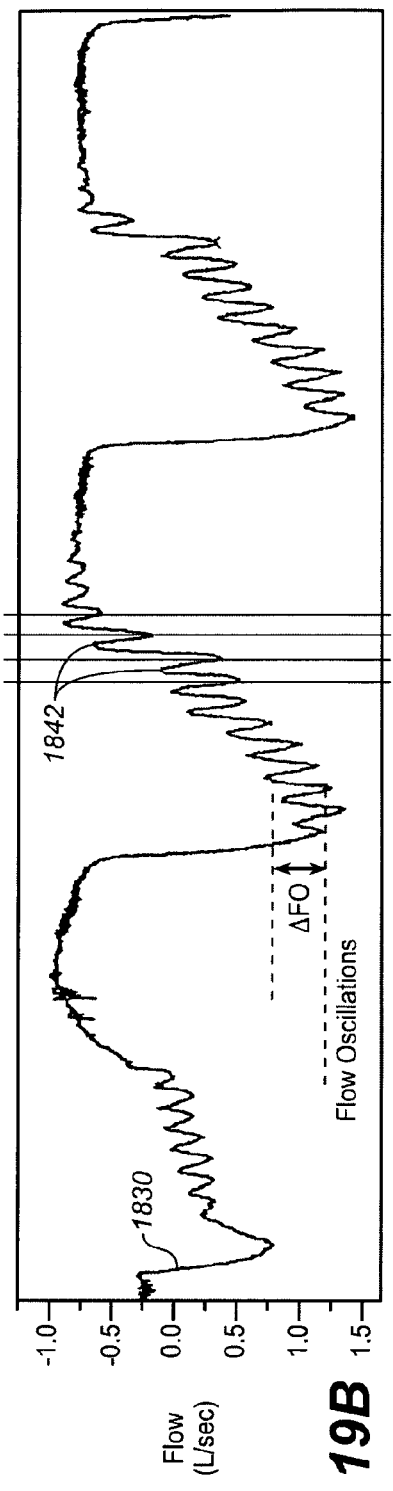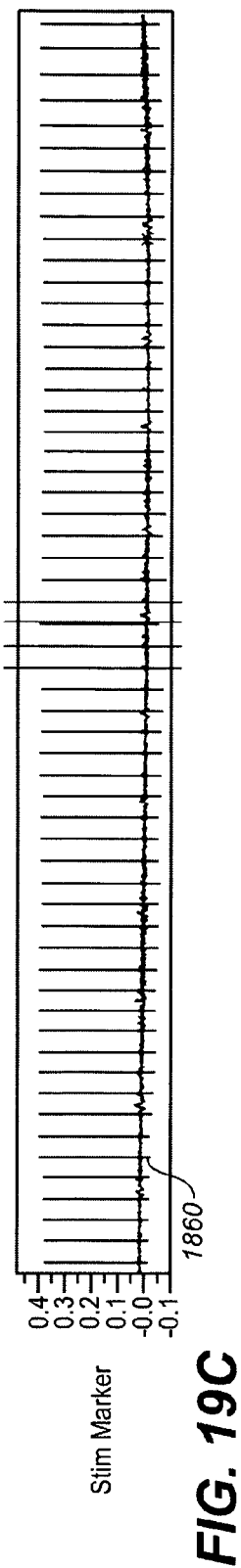
FIG. 19A
FIG. 19B
FIG. 19C

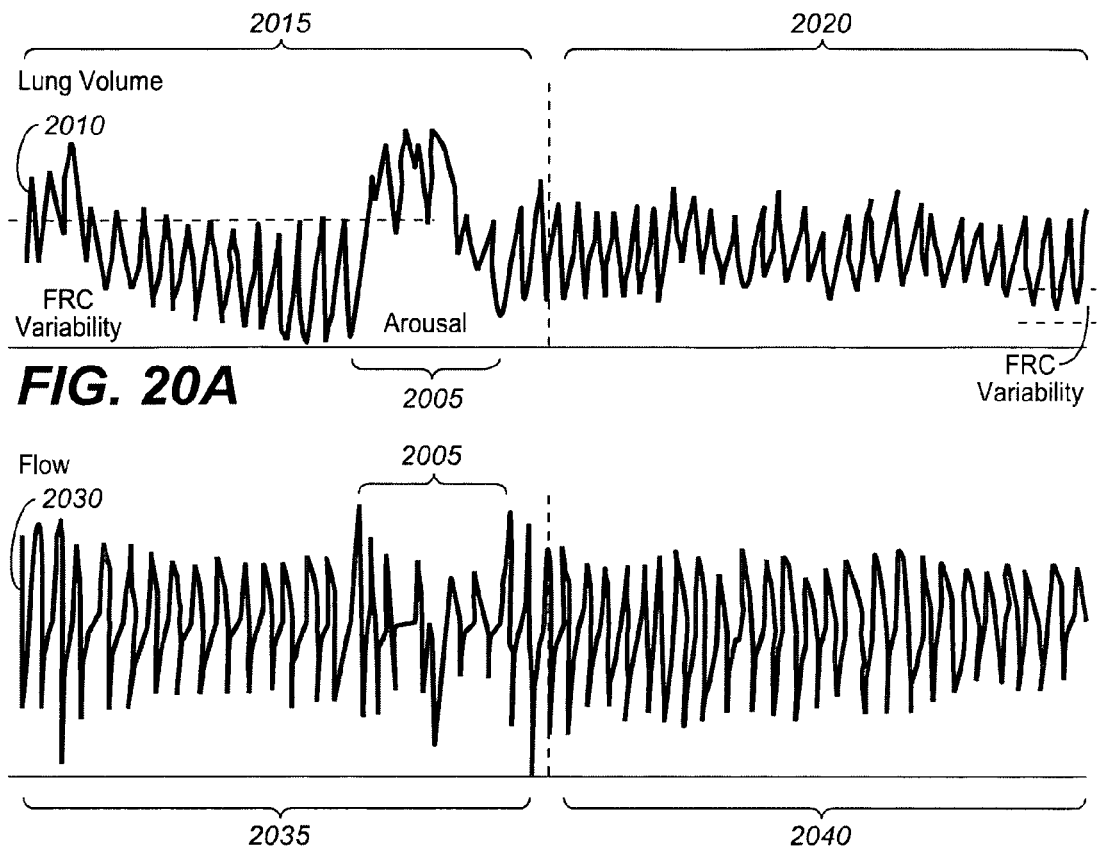
FIG. 20A
FIG. 20B
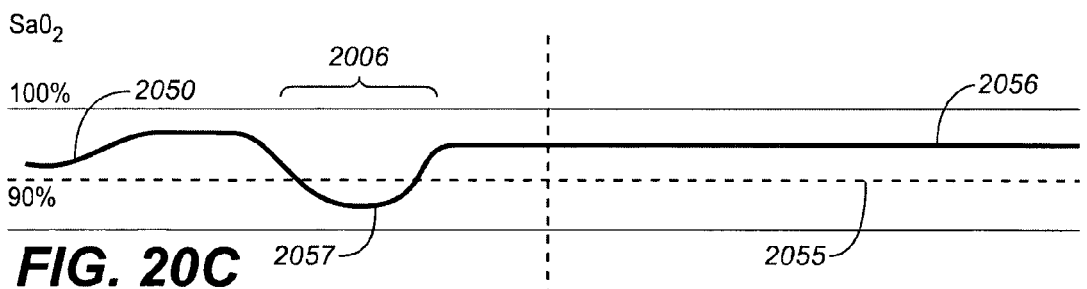
FIG. 20C
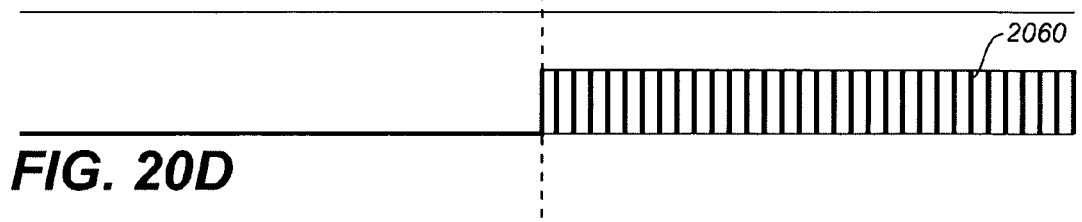
FIG. 20D

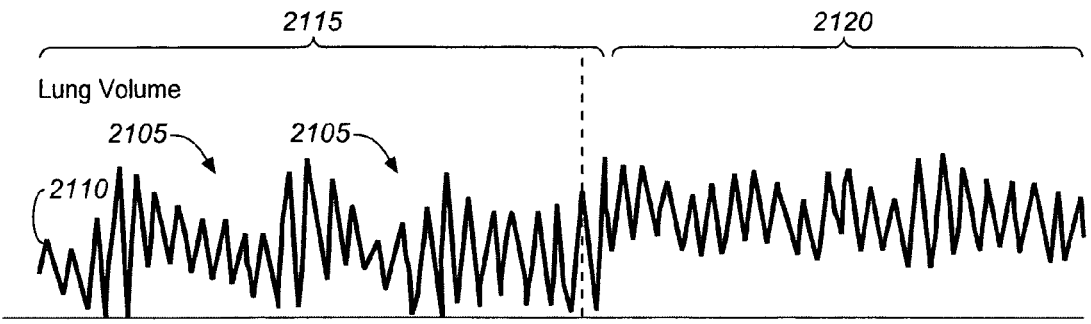
FIG. 21A
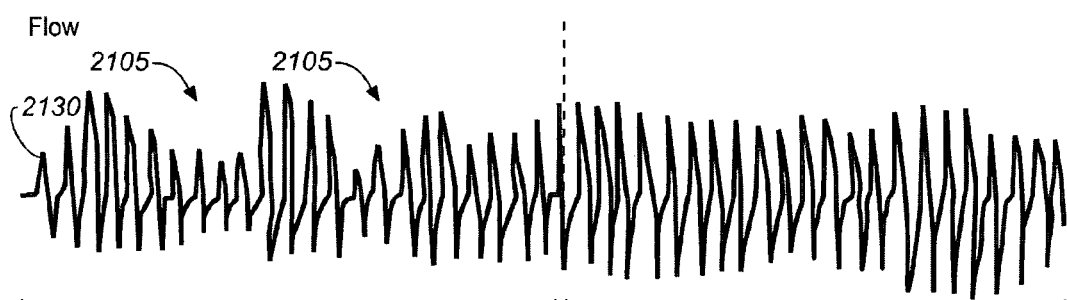
FIG. 21B
FIG. 21C
FIG. 21D

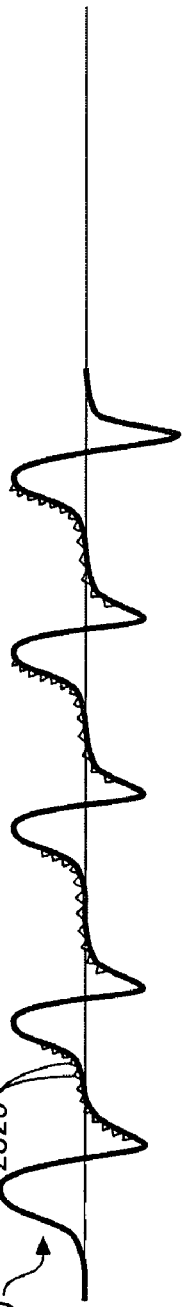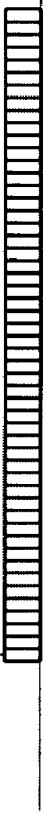

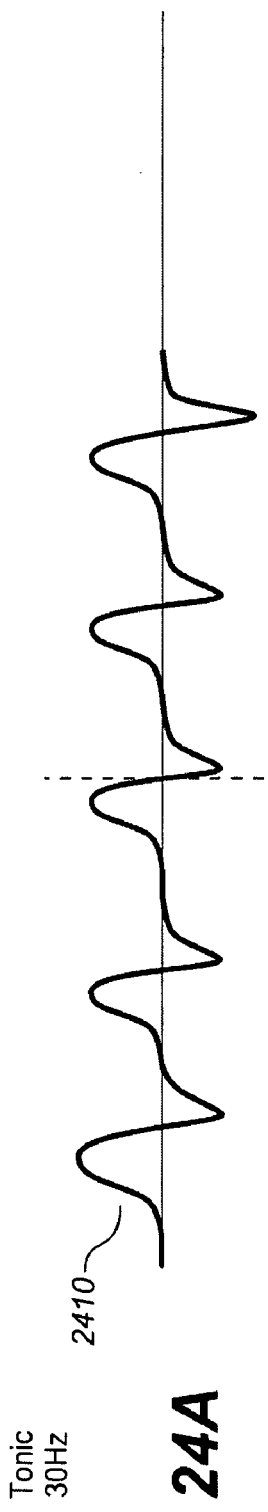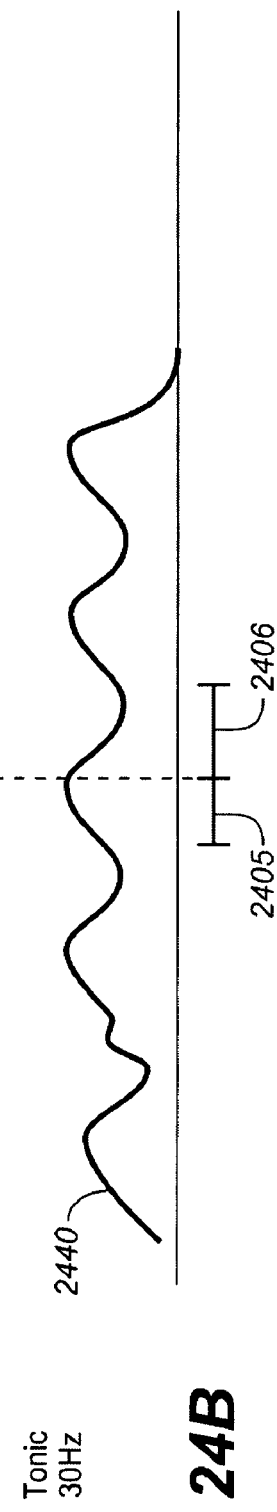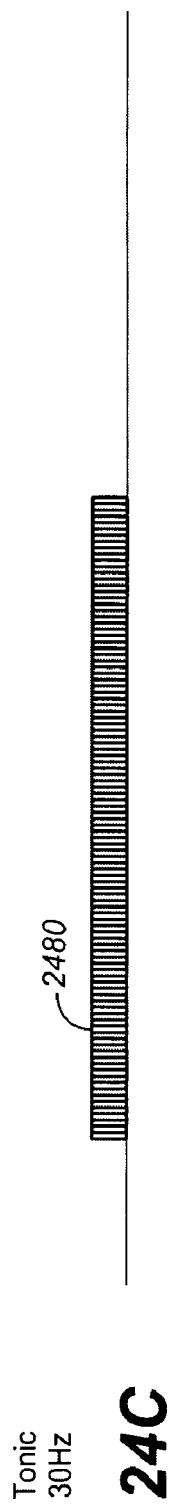

THERAPEUTIC DIAPHRAGM STIMULATION DEVICE AND METHOD

RELATED APPLICATION DATA

This application is a continuation in part of U.S. application Ser. No. 11/480,074 filed Jun. 29, 2006 which is a continuation in part of U.S. application Ser. No. 11/271,726 filed Nov. 10, 2005 which is a continuation in part of U.S. application Ser. No. 10/966,484 filed Oct. 15, 2004; U.S. application Ser. No. 10/966,474, filed Oct. 15, 2004; U.S. application Ser. No. 10/966,421, filed Oct. 15, 2004; and U.S. application Ser. No. 10/966,472 filed Oct. 15, 2004 which are continuations in part of U.S. application Ser. No. 10/686,891 filed Oct. 15, 2003 entitled: BREATHING DISORDER DETECTION AND THERAPY DELIVERY DEVICE AND METHOD all of which are incorporated herein by reference.

FIELD OF THE INVENTION

This invention relates to a device and method for treating a variety of conditions, disorders or diseases with diaphragm/phrenic nerve stimulation.

BACKGROUND OF THE INVENTION

Diaphragm stimulation has been proposed when neurological activation of the diaphragm is not present, for example in quadriplegics. Diaphragm stimulation has been proposed for treating central sleep apnea by providing respiration when absent.

A number of diseases, disorders and conditions may relate to, have comorbidities with, affect, be affected by respiratory or lung health status, respiration, ventilation, or blood gas levels. Such diseases and disorders may include but are not limited to obstructive respiratory disorders, upper airway resistance syndrome, snoring, obstructive apnea; central respiratory disorders, central apnea; hypopnea, hypoventilation; obesity hypoventilation syndrome; other respiratory insufficiencies, inadequate ventilation or gas exchange, chronic obstructive pulmonary diseases; asthma; emphysema; chronic bronchitis; circulatory disorders; hemodynamic disorders; hypertension; heart disease; chronic heart failure; cardiac rhythm disorders; obesity or injuries in particular affecting breathing or ventilation. Treatments of such diseases, disorders and conditions have varied substantially.

It would be desirable to provide treatment for one or more of these various diseases, disorders and conditions.

As noted, an example of disorders that may be treated include obstructive respiratory disorders such as obstructive apnea. There are several factors believed to contribute to the occurrence of obstructive respiratory events including anatomical deficiencies, deformities or conditions that increase the likelihood or occurrence of upper airway collapse; ventilatory instability; and fluctuations in lung volumes. There is believed to be a relationship between lung volume and the aperture of the upper airway with larger lung volume leading to greater upper airway patency.

Some obstructive sleep apnea (OSA) patients have increased upper airway resistance and collapsibility that may contribute to vulnerability to obstructive respiratory events. The pharyngeal airway is not supported by bone or cartilaginous structure and accordingly relies on contraction of the upper airway dilator muscles to maintain patency. The pharyngeal airway represents a primary site of upper airway closure.

Some OSA therapy has been based on a belief that OSA results from the size and shape of the upper airway muscles or conditions such as obesity that create a narrowing of the upper air passageway and a resulting propensity for its collapse.

In patients with obstructive sleep apnea, various treatment methods and devices have been used with very limited success.

CPAP machines have been used to control obstructive sleep apnea by creating a continuous positive airway pressure (CPAP) at night. External ventilatory control has been proposed including sensors that sense a cessation of breathing to determine when an obstructive sleep apnea event is occurring.

An implantable stimulator that stimulates the hypoglossal nerve after sensing an episode of obstructive sleep apnea has been proposed but has failed to provide satisfactory results in OSA patients.

Treating OSA has primarily relied on continuous treatment or detection of an obstructive respiratory event when it is occurring, i.e., when the upper air passageway has closed.

Drug therapy has not provided satisfactory results.

In central sleep apnea, as opposed to obstructive sleep apnea, it has been proposed to stimulate a patient's diaphragm or phrenic nerve to induce breathing where there is a lack of central respiratory drive. However, such therapy has been contraindicated for obstructive sleep apnea or respiratory events where there is an obstructive component, at least in part because stimulating a patient to breathe when the airway is obstructed is believed to further exacerbate the collapsing of the airway passage by creating a pressure that further closes the airway.

Accordingly, it would be desirable to provide an improved device and method for treating OSA.

SUMMARY OF THE INVENTION

The present invention provides for treating diseases, disorders or conditions by stimulating tissue to cause a diaphragm response.

In accordance with one aspect of the invention treatment may be provided for number of diseases, disorders and conditions may relate to, have co-morbidities with, affect, be affected by respiratory or lung health status, respiration, ventilation, or blood gas levels. Such diseases and disorders may include but are not limited to obstructive respiratory disorders, upper airway resistance syndrome, snoring, obstructive apnea; central respiratory disorders, central apnea; hypopnea, hypoventilation, obesity hypoventilation syndrome other respiratory insufficiencies, inadequate ventilation or gas exchange, chronic obstructive pulmonary diseases; asthma; emphysema; chronic bronchitis; circulatory disorders; hemodynamic disorders; hypertension; heart disease; chronic heart failure; cardiac rhythm disorders; obesity or injuries in particular affecting breathing or ventilation.

In accordance with one aspect of the invention stimulation is provided to tissue of a subject to elicit a diaphragm response. In addition to causing a direct diaphragm response, stimulation may be provided to elicit an indirect lung or related response when a diaphragm movement is elicited. For example, lung volume changes, remodeling of the lung structures and/or causing a feedback response due to lung movement (e.g. by affecting stretch receptor response, vagal response or other feedback mechanisms) may be elicited as well.

While electrical stimulation is described herein, other energies may be applied to tissue to elicit such a response, for example, magnetic stimulation.

According to one embodiment a fully implanted system is provided. However, other embodiments may include external sensing and/or control; internal microstimulators; external stimulation and control; or a combination of the foregoing. Also according to one variation, the desired effects may be achieved with stimulation of the intercostals and/or abdominal muscles.

In accordance with one aspect of the invention, stimulation is provided during intrinsic breathing. In accordance with another aspect of the invention an increased or supplemental lung volume is provided over intrinsic breathing. In accordance with one aspect of the invention such supplemental lung volume comprises an increase in tidal volume with respect to existing tidal volume. In accordance with another aspect of the invention such supplemental lung volume may comprise an increased functional residual capacity (FRC) or an increased end expiratory lung volume. In accordance with another aspect of the invention a biased lung volume may be provided. In accordance with one aspect, stimulation is provided during intrinsic breathing to provide improved gas exchange.

In accordance with another aspect of the invention, a flow limitation is reduced or removed providing improved flow or peak flow.

In accordance with another aspect of the invention, augmented ventilation is provided by increasing or adding to diaphragm EMG, i.e., supplementing diaphragm muscle contraction or contractions. Accordingly, augmented ventilation may provide flow during intrinsic respiration that improves gas exchange.

In accordance with one aspect of the invention, minute ventilation may be manipulated or altered, e.g. by manipulating one or more of the inspiration period, the non-inspiration period (exhalation), the ratio thereof, lung volume or the respiration rate.

According to one aspect of the invention, gas exchange may be altered e.g., by manipulating (with stimulation described herein) one or more of lung volume, tidal volume, FRC, flow characteristics, respiratory or lung structures such as alveoli or bronchioles, the inspiration period, the non-inspiration period (exhalation), the ratio of the inspiration period to the non-inspiration period, or the respiration rate.

According to one aspect of the invention gas exchange may be altered by manipulating functional residual capacity to thereby increase surface area in the alveoli to provide an increase in gas exchange during respiration. This increase in functional residual capacity as noted herein may be used to treat a variety of diseases, disorders or conditions.

In accordance with another aspect of the invention blood oxygen saturation levels may be increased, e.g. by manipulating (with stimulation described herein) one or more of lung volume, tidal volume, FRC, flow characteristics, respiratory or lung structures such as alveoli or bronchioles, the inspiration period, the non-inspiration period (exhalation), the ratio of the inspiration period to the non-inspiration period, the respiration rate. In accordance with one aspect of the invention, blood oxygen saturation levels are increased by providing stimulation to the diaphragm to elicit an augmented ventilation.

In accordance with another aspect of the invention, lung structures such as the alveoli or bronchioles are manipulated to provide a therapeutic benefit. For example, an increased FRC provided as described herein may increase the ventilated surface area of the alveoli or bronchioles to thereby provide an improved gas exchange. An increase in FRC may also reduce collapsing of such structures which may occur in a disease state, or may open constricted bronchioles (e.g. in asthma patients).

In accordance with the invention, stimulation may be provided to elicit a non-physiological effect, i.e., an effect that is not typically associated with normal intrinsic breathing. One example of such non-physiological effect may include flow oscillations that create one or more non-physiological flow characteristics such as turbulent flow, laminar flow with Taylor dispersion, or asymmetric velocity profiles.

In accordance with another aspect of the invention stimulation may be configured to elicit relatively fast short breaths, i.e., inflows or flow oscillations; short fast diaphragm contractions. These oscillations, contractions or breaths are shorter in duration than those of an intrinsic breath. The oscillations, contractions or breaths may also be lower in tidal volume than a volume of a typical intrinsic breath. In accordance with one aspect, small volume changes of about 20% or less than a normal intrinsic tidal volume are elicited. Such fast short contractions or breaths may provide an altered gas exchange and thereby treat one or more conditions, disorders or diseases, for example as set forth herein. Such short fast contractions or breaths may also be configured to increase lung volume, increase FRC, increase breathing stability, improve or augment ventilation, improve blood gas levels and/or increase SaO2 levels in subjects with one or more conditions, disorders or diseases, fore example, as set forth herein. Short fast pulses of stimulation according to one aspect of the invention provide a pulse of added volume in the lungs to slow exhalation. This is believed to increase FRC, improve gas exchange and thereby improve ventilatory stability as well as stabilize the upper airway. Such stimulation segment may be, for example, a stimulation applied during one or more intrinsic respiration cycles or portions thereof.

In accordance with another aspect of the invention low energy stimulation may be used to create one or more affects. Low energy stimulation as generally understood may mean a low pulse frequency, low pulse amplitude, low pulse duration, low pulses per burst, low burst duration, low burst frequency, a combination of one or more of the foregoing, and/or low overall energy applied during a stimulation segment. Such low energy stimulation may comprise sequential low energy output whereby the individual pulses would not provide sufficient energy to elicit a normal intrinsic breath. Such low energy pulses may also be configured to control and manage the pulmonary stretch receptor threshold levels, in other words the low energy pulse or series of pulses may be designed so that any resulting diaphragm movement does not activate stretch receptors. Such low energy pulses may be configured to avoid airway closure because of a more gentle volume and flow increases and lower negative pressures at the upper airway. These and other affects of low energy stimulation may reduce arousals during sleep. The resulting elicited movement may accordingly be sufficiently low and/or gradual so as not to elicit substantial stretch receptor response thereto. Such low energy stimulation may provide an altered gas exchange and thereby treat one or more conditions, disorders or diseases, for example as set forth herein. Such low energy stimulation may also be configured to increase lung volume, increase FRC, increase breathing stability, improve or augment ventilation, improve blood gas levels and/or increase SaO2 levels in subjects with one or more conditions, disorders or diseases, for example, as set forth herein. Low energy pulses may be used to elicit short fast breaths or diaphragm contractions or high frequency contractions as described herein. Such stimulation segment may be, for example, a stimulation applied during one or more intrinsic respiration cycles or portions thereof.

According to another aspect of the invention, stimulation may be configured to elicit twitch therapeutic contractions of the diaphragm to achieve a desired therapeutic benefit. In electrical stimulation of a diaphragm, frequency is directly related to the contractile force of the induced muscle contraction and the stimulation amplitude is directly related to spread of induced contraction within the stimulated muscle. Stimulation pulses cause release of calcium ions and rise in the intracellular calcium ion concentration which is directly related to contractile force produced by the muscle cell. There is a one to one relationship between the individual stimulation pulses and rise in intracellular calcium ion concentration where the pulses have high enough amplitude to trigger an action potential initiation. Once the calcium ion concentration rises, ion pumps activate to quickly reduce the intracellular ion concentration. This rise and fall of calcium concentration is characterized by a spike followed by more gradual decrease. If the stimulation pulses are delivered quickly enough, it is possible that rate of rise of intracellular ion concentration is much greater than rate of decrease of intracellular calcium ion caused by the ion pumps. Such scenario would lead to a constant high intracellular calcium concentration which causes a sustained contraction of the muscle or diaphragm. If the stimulation pulses are delivered slow enough to allow full extraction of intracellular calcium ions by the ion pumps, the muscle would twitch in response to each stimulation pulses but will not have sustained contraction, i.e. will have twitch contractions. If the pulses are delivered at an intermediate rate such that increase in calcium ion concentration occurs before the calcium pumps could decrease the calcium ion concentration to basal level, there will be a gradual accumulation of steady-state calcium concentration in addition to spikes caused by the individual pulses. In such case, the muscle will have both twitch contractions from the rapid increase of calcium concentration as well as increasing sustained contraction due to rising steady-state calcium concentration level, i.e., a combination of both sustained and twitch diaphragm contractions. According to one variation of the invention stimulation is provided to elicit twitch contractions to achieve a desired therapeutic benefit. According to one variation of the invention stimulation is provided to elicit a combination of sustained and twitch contractions to achieve a desired therapeutic benefit. According to one variation of the invention stimulation is provided to elicit a sustained contraction to achieve a desired therapeutic benefit.

In accordance with another aspect of the invention, stimulation may be provided at a pulse energy and frequency that produces both sustained and twitch activation of the diaphragm muscle. According to one aspect, such stimulation may be provided during or on top of intrinsic breathing. Such stimulation may be configured to produce a sustained effect, i.e., so that the lung volume or FRC change will be produced over a longer period of time, 1 or more breaths for example. A slower increase in volume, FRC or flow may be beneficial for a number of reasons, including but not limited to, in avoiding arousals when stimulation is delivered during sleep. Such stimulation may provide a more gradual transition into and out of one or more stimulated effects. Such stimulation may provide a more gradual change in volume and flow reducing the possibility of flow limitation or obstruction due to increased negative pressure in the airway. According to one aspect, a bias of lung volume is produced with a stimulation having a sustained contraction component and twitch contraction component. Furthermore, with pulses of added lung volume the multi-component stimulation may increase the ventilatory benefits that are described above, such as improved gas exchange, increased FRC, improved upper airway tonicity, and stabilized ventilation.

A stimulation having a component of twitch contraction stimulation may be configured to elicit one or more of the following affects: an altered gas exchange, an increased lung volume, an increased FRC, a lung volume bias, increased breathing stability, improved or augmented ventilation, improved blood gas levels and/or increased SaO2 levels in subjects with one or more of the conditions, disorders or diseases described herein. Twitch contraction stimulation may comprise a lower signal frequency stimulation having sufficient energy to cause muscle contraction and volume change may be applied, e.g. less than 5 Hz. A combined stimulation of twitch and sustained contractions may comprise a medium frequency signal of about 3 Hz to about 30 Hz and more preferably of about 5 to 20 Hz. The stimulation may also be tailored to an individual to provide the desired diaphragm response. The frequencies may vary to some extent based on the total stimulation energy of the stimulation signal and the type or location of stimulation provided, e.g., diaphragm or phrenic nerve.

According to another aspect of the invention, high frequency contraction stimulation is provided. High frequency contractions are defined as contractions that occur at a rate greater than an intrinsic breathing rate. While not intending to be limited thereto, in one variation, high frequency contractions occur at a rate of e.g. between 10 to 150 times greater that intrinsic breathing, and more preferably between about 15 to 50 times greater than intrinsic breathing. The high frequency contractions may occur on top of intrinsic breathing. High frequency contractions may be comprised of a plurality of short fast breaths. The high frequency contractions may be configured to provide an altered or improved gas exchange, to increase lung volume, increase FRC, increase breathing stability, improve or augment ventilation, improve blood gas levels and/or increase SaO2 levels in subjects with one or more of conditions, disorders or diseases, for example as described herein. These effects may occur due to one or more mechanisms. In accordance with one aspect, the high frequency contraction stimulation may be configured to elicit non-physiologic flow characteristics to thereby improve gas exchange and/or provide one or more of the effects described herein. According to one aspect, such non-physiological flow may be achieved, among other things, by providing contractions in a range of about 3 to 15 contractions per second. High frequency stimulation may provide small gas exchanges or flow oscillations to achieve one or more affects as described herein. Such high frequency contraction stimulation may be configured to augment or add to ventilation. Twitch stimulation whether or not combined with sustained stimulation, may be used to create a high frequency contraction stimulation, i.e. contraction at a rate that provides multiple contractions within an intrinsic breath.

According to one aspect of the invention, a lower energy stimulation signal having sufficient energy to cause twitch muscle contraction may be applied.

Depending on the desired therapeutic benefit, various stimulation provided herein may be directed to achieving one or more affects. For example, a plurality of small gas exchanges or flow oscillations may be beneficial during intrinsic breathing, or an increase in resting lung volume or FRC may be desired. To achieve desired contractions a stimulation energy is provided that is sufficient to cause a contraction having a desired therapeutic benefit.

According to one example causing gas exchange without a lung expansion typically associated with a normal breath, may benefit patients with diseased lungs that do not have healthy viscoelastic properties or that may be disturbed or further damaged by higher lung expansion, e.g., of a normal breath of a healthy patient or by repetitive higher lung inflations. Such gas exchanges may be elicited using low energy stimulation, twitch contraction stimulation and/or high frequency contraction stimulation. Accordingly, twitch, high frequency or low energy stimulation may be used to improve gas exchange in disease states where sustained contractions may exacerbate conditions.

Small flow oscillations produced by the stimulus may also reduce pressure swings in lung alveoli, while providing sufficient volume for ventilation. The low energy stimulation or pulses may cause increased alveolar ventilation in a number of pulmonary diseases or disorders, or in other disease states (e.g., heart failure related). While not limiting the application of this invention, diseases that may be treated with high frequency stimulation, twitch contraction stimulation or low energy stimulation may include diseases that may benefit from increased gas exchange such as COPD, asthma, emphysema, and/or conditions that contribute to hyponea or hypercapnia. Stimulation may be applied to treat asthma or COPD whereby the high frequency contraction stimulation promotes expansion or reduces contraction of the bronchioli or alveoli. This may be accomplished by applying stimulation for a period of time, e.g. 30 minutes at a time thereby stretching or helping the alveoli or bronchioles become resistant to constriction that occurs during one or more disease states. Smaller breaths, gas exchanges may be used in surgery or post surgically to improve blood gas concentrations of such patients. A number of these diseases, disorders or conditions as described herein may benefit from a therapeutic stimulation that increases FRC. Increasing FRC may help avoid collapse of alveoli which may occur in a disease state, or help open constricted bronchioles in asthma subjects.

Twitch contraction, high frequency contraction, or low energy stimulation may also be provided in a manner that improves gas exchange while not significantly increasing functional residual capacity. In some diseases, disorders or conditions an increase in FRC is not desirable, for example where there is a limitation of exhalation. Emphysema is one of such conditions. In emphysema the elasticity of the bronchial tubes is lost, and collapse of bronchial tubes will occur during fast, high volume exhalation. The described therapies, including high frequency contraction stimulation, twitch contraction and/or low energy contraction, may decrease the chance of this collapse by providing additional ventilation without increasing the rate and volume of exhalation.

Smaller breaths or augmented gas exchanges may also provide improved gas exchange in patients with obstructive disorders or who have a tendency to have upper airway obstructions when stimulation is provided (i.e. stimulation may be provided in such circumstances to augment intrinsic breathing and/or provide higher frequency contractions). Shorter, faster and/or lower amplitude breaths or gas exchanges my beneficial in patients with flow limitation or obstructive tendencies where the upper airway may respond to greater negative pressure swings by obstructing or becoming flow limited.

In accordance with another aspect of the invention, ventilatory or breathing stability may be provided. According to one aspect of the invention, stimulation is provided to stabilize flow. According to another aspect of the invention stimulation is provided to stabilize functional residual capacity or minimum lung volume. According to one aspect of the invention, stimulation is provided to increase tidal volume, e.g., to compensate for reduced central drive. Ventilatory or breathing stability may be determined a number of ways. One such measure of ventilatory stability is the deviation or variation of one or more measures of respiration. While not intending to be limiting, deviations or variations in peak flow is one measure of ventilatory stability. Deviations or variations in lung volume may be another measure. Deviations and variations in functional residual capacity may be a measure. Deviations and variations in tidal volume or minute ventilation may be a measure. One or more deviations or variations in ventilatory stability may be determined by changes in variability or by deviations in one or more measures of respiratory effort, diaphragm EMG, phrenic nerve signals, other sensed respiratory related information such as pressure, thoracic impedance, as well as other sensed signals known in the art. According to one aspect of the invention improved ventilatory stability may be provided by eliciting twitch contractions of the diaphragm or a combination of twitch and sustained contraction. According to one aspect of the invention ventilatory stability may be provided by providing high frequency contraction stimulation, i.e., contractions, at a frequency greater than the frequency of intrinsic or desired normal breathing on top of intrinsic breathing. According to one aspect of the invention ventilatory stability may be provided by providing low energy stimulation. According to another aspect of the invention ventilatory stability may be provided by increasing lung volume. According to another aspect of the invention ventilatory stability may be provided by controlling breathing or entraining breathing.

In accordance with another aspect of the invention twitch or high frequency contraction stimulation is provided on top of paced breathing.

While lung volume bias may be achieved with stimulation having a component of twitch stimulation described herein, it may also be achieved with stimulation that produces a sustained contraction.

According to another aspect of the invention, twitch stimulation, high frequency stimulation and/or low energy stimulation may be provided during an exhalation phase to manipulate exhalation, minute ventilation blood gas exchange and/or oxygen saturation levels.

According to another aspect of the invention the stimulation protocols herein may be provided on a continuous or intermittent basis during intrinsic breathing. For example stimulation may be provided for a predetermined number of breaths or a predetermined time period, and then may be turned off for a predetermined number of breaths or a predetermined time period. This may be constant, or on and off. The durations may be selected based on ventilatory stability criteria or respiration events detected (AHI or other measure of events, disorders or conditions) or other criteria related to a disease, disorder or condition. Stimulation may also be triggered or timed to portions of a respiration cycle.

In accordance with one aspect of the invention, in a patient diagnosed with obstructive sleep apnea, tissue associated with the diaphragm or phrenic nerve is electrically stimulated to prevent obstructive respiratory events.

In accordance with one aspect of the invention stimulation of the diaphragm or phrenic nerve is provided to such obstructive sleep apnea patients to reduce the occurrence of upper airway collapse or upper airway flow limitation.

In accordance with one aspect of the invention, a device and method for increasing functional residual capacity (i.e., end expiratory lung volume) is provided for treating obstructive respiratory disorders such as obstructive sleep apnea or other disorders diseases or conditions.

In accordance with one aspect of the invention, a device and method for increasing upper airway patency is provided.

In accordance with one aspect of the invention, a device and method are provided for providing ventilatory stability in an obstructive sleep apnea patient or patients with other diseases, disorders or conditions.

In accordance with one aspect of the invention, an indicator of an impending obstructive respiratory event is detected prior to event onset.

In accordance with an aspect, unstable breathing may be detected, arousals may be detected and stimulation may be provided to stabilize breathing, reduce oxygen desaturation and/or reduce or avoid arousal events.

In accordance with one aspect of the invention, a method for mitigating (i.e., preventing or lessening) obstructive respiratory events is provided. In accordance with an aspect of the invention, oxygen saturation levels are stabilized or generally increased to avoid desaturations. In accordance with another aspect of the invention, flow limitations leading to arousals are reduced to avoid arousals.

In accordance with one aspect of the invention, a method and device is provided for synchronizing stimulation with one or more portions of an intrinsic breathing cycle.

In accordance with one aspect of the invention, a device and method for eliciting deep inspiration while avoiding airway closure or other flow limitation are provided.

In accordance with one aspect of the invention, a device and method for normalizing or reducing peak flow while increasing tidal volume are provided.

In accordance with one aspect of the invention, a device and method for manipulating exhalation are provided.

In accordance with one aspect of the invention, a device and method for entraining breathing are provided.

In accordance with another aspect of the invention, a device detects when an obstruction has occurred to a particular extent and refrains from stimulating if the collapse has occurred to a particular extent.

In accordance with another aspect of the invention, a low level of stimulation is provided for therapeutic effects. In other words, low level stimulation is a stimulation whereby intrinsic breathing is permitted during stimulation.

In accordance with another aspect of the invention, a low level of stimulation to the diaphragm or phrenic nerve is provided through or after airway closure to speed up airway opening and reduce arousal.

According to another aspect of the invention, at least two groups of muscles associated with respiration may be controlled or coordinated.

In accordance with an aspect of the invention, an increase in FRC or a supplemental lung volume may be provided to reduce upper airway resistance. A reduction in arousals due to upper airway resistance may be provided by stimulating to reduce upper airway resistance. Upper airway resistance syndrome UARS has been clinically defined by decreased oronasal airflow and increased negative inspiratory esophageal pressure (i.e., flow limitation and snoring), without frank apnea or oxygen desaturation below apneaic threshold. Accordingly stimulation as set forth herein may be provided to treat UARS.

In accordance with another aspect of the invention a device and method for reducing snoring is provided. Accordingly, improving upper airway patency or functionality or reducing upper airway resistance associated with snoring may be provided as described herein.

In accordance with another aspect of the invention, a device and method for treating obesity hypoventilation syndrome is provided. In such patients, hypoventilation occurs primarily at night, or depending on patient position. According to one aspect, stimulation is provided to increase functional residual capacity. According to one aspect, stimulation is provided to stabilize breathing as described herein. In accordance with another aspect paced breathing is provided as described herein. According to another aspect, paced breathing and bias stimulation to increase functional residual capacity is provided to stabilize breathing.

In accordance with another aspect of the invention stimulation is provided to elicit a respiratory response that in turn reduces sympathetic bias that occurs during central sleep apnea and obstructive sleep apnea. In accordance with one aspect of the invention, increasing lung volume, particularly during exhalation is provided by stimulating the diaphragm in accordance with one or more devices or methods herein. The stimulation may be configured so that the increase in lung volume in a manner that thereby triggers vagal reflexes. For example, stimulation may be provide increases in lung volume during exhalation to thereby trigger vagal reflexes.

In accordance with another aspect of the invention, a device and method for treating one or more conditions related to COPD is provided. Accordingly stimulation is provided that increases gas exchange while avoiding a significant increase in functional residual capacity. For example, twitch stimulation as described herein may be provided without a substantial sustained contraction component. A multi-component stimulation may be provided to achieve such result. For example, twitch contraction stimulation may be provided in combination with other stimulation that slows exhalation, including but not limited to controlled breathing described in U.S. application Ser. No. 10/966,474 incorporated herein by reference.

In accordance with another aspect of the invention, a device and method for treating hypertension is provided. Hypertension may be treated by slowing respiration or increasing ventilatory stability using one or more techniques described herein. For example, FRC may be increased to slow breathing; high frequency contraction stimulation, low energy stimulation and/or twitch contraction stimulation may be used to increase ventilation while slowing respiration; or breathing also may be controlled or entrained to slow breathing.

In accordance with another aspect of the invention stimulation is provided to patients to reduce perioperative or post operative complications or respiratory related conditions. Such conditions may relate to patient position or anesthesia, as well as medical condition including for example those that reduce the FRC of the patient. Such stimulation may also be provided preoperatively, during anesthesia as well, and during operative procedures as well. Stimulation may be provided to such patients increase the functional residual capacity using one or more methods or devices herein. In accordance with an aspect of the invention, temporary leads are provided whether implanted or external, to provide temporary stimulation to perioperative or other patients.

In accordance with another aspect of the invention stimulation may be individually tailored for a patient to achieve one or more of the desired physiological or respiratory results discussed above.

These and other inventions are described herein and/or set forth in the claims herein.

BRIEF DESCRIPTION OF THE DRAWINGS

FIG. 4A is a schematic illustration of respiration of an exemplary obstructive sleep apnea patient as the patient is going into an obstructive sleep apnea event.

FIG. 4B is a schematic illustration of respiration of an exemplary obstructive sleep apnea patient as the patient is going into an obstructive sleep apnea event.

FIGS. 4C and 4D are schematic illustrations respectively of respiration response and stimulation waveforms illustrating a stimulation method using a stimulation device according to the invention in which the obstructive sleep apnea event illustrated in FIG. 4A is treated with deep inspiration stimulation.

FIG. 5A is a schematic illustration of respiration of an exemplary obstructive sleep apnea patient as the patient is going into an obstructive sleep apnea event.

FIGS. 5B and 5C are schematic illustrations respectively of respiration response and stimulation waveforms illustrating a stimulation method using a stimulation device according to the invention in which the obstructive sleep apnea event illustrated in FIG. 5A is treated with deep inspiration stimulation.

FIGS. 6A, 6B and 6C are schematic illustrations respectively of airflow, tidal volume and corresponding stimulation waveforms illustrating a stimulation method using a stimulation device according to the invention in which stimulation is applied during a portion of the respiration cycles.

FIGS. 7A and 7B are schematic illustrations respectively of tidal volume and corresponding stimulation waveforms illustrating a stimulation method using a stimulation device according to the invention in which stimulation is applied during a portion of the respiration cycles.

FIGS. 8A and 8B are schematic illustrations respectively of tidal volume and corresponding stimulation waveforms illustrating a stimulation method using a stimulation device in which stimulation is applied in accordance with the invention.

FIGS. 11A and 11B are schematic illustrations respectively of respiration response and stimulation waveforms illustrating a stimulation method using a stimulation device according to the invention.

FIGS. 13A and 13B are schematic illustrations respectively of respiration response and stimulation waveforms illustrating a stimulation method using a stimulation device according to the invention.

FIG. 16B is a schematic example of a waveform of an integrated signal processed by the signal processor of FIG. 16A.

FIG. 16C is a schematic EMG envelope waveform.

FIG. 16D is a schematic waveform corresponding to or correlated with air flow.

FIG. 16E is a schematic waveform correlated to intrapleural pressure.

FIGS. 17A, 17B, 17C, 17D, and 17E are schematic illustrations respectively of diaphragm EMG envelope; flow or inverse of upper airway pressure; tidal volume or inverse of intrapleural pressure; and corresponding diaphragm stimulation; illustrating a stimulation method using a stimulation device in which stimulation is applied in accordance with the invention.

FIGS. 19A, 19B and 19C are schematic illustrations respectively of lung volume, flow and diaphragm stimulation applied in accordance with the invention.

FIGS. 20A, 20B, 20C and 20D are schematic illustrations respectively of lung volume, flow and diaphragm stimulation applied in accordance with the invention.

FIGS. 21A, 21B, 21C and 21D are schematic illustrations respectively of lung volume, flow and diaphragm stimulation applied in accordance with the invention.

FIGS. 23A, 23B and 23C are schematic illustrations of respectively of flow, lung volume and diaphragm stimulation applied in accordance with the invention.

FIGS. 24A, 24B and 24C are schematic illustrations of respectively of flow, lung volume and diaphragm stimulation applied in accordance with the invention.

DETAILED DESCRIPTION

In accordance with one aspect of the invention treatment is provided for number of diseases, disorders and conditions may relate to, have co-morbidities with, affect, be affected by respiratory or lung health status, respiration, ventilation, or blood gas levels. Such diseases and disorders may include but are not limited to obstructive respiratory disorders, upper airway resistance syndrome, snoring, obstructive apnea; central respiratory disorders, central apnea; hypopnea, hypoventilation, obesity hypoventilation syndrome other respiratory insufficiencies, inadequate ventilation or gas exchange, chronic obstructive pulmonary diseases; asthma; emphysema; chronic bronchitis; circulatory disorders; hemodynamic disorders; hypertension; heart disease; chronic heart failure; cardiac rhythm disorders; obesity or injuries in particular affecting breathing or ventilation.

According to one embodiment, a device is provided that manipulates breathing according to one or more protocols, by stimulating the diaphragm or phrenic nerve to mitigate or prevent obstructive respiratory events including obstructive sleep apnea or other events with an obstructive component. The device may comprise a phrenic nerve or diaphragm stimulator and a sensor configured to sense a condition of a subject indicating a possibility that an obstructive respiratory event will occur or is occurring. In accordance with the invention, obstructive respiratory events are characterized by a narrowing of the air passageway, typically the upper air passageway. Examples of obstructive respiratory events include but are not limited to obstructive sleep apnea, obstructive hypopnea and other respiratory events with an obstructive component.

In another embodiment, stimulation is applied at a low level through or after an obstructive respiratory event has occurred. Low level is at a level that permits intrinsic breathing on top of the low level. Level refers to volume level achieved by a given stimulation parameter.

In addition, in accordance with the invention stimulation techniques for controlling or manipulating breathing may be used for therapeutic purposes in other non-OSA patients.

Figure 1:
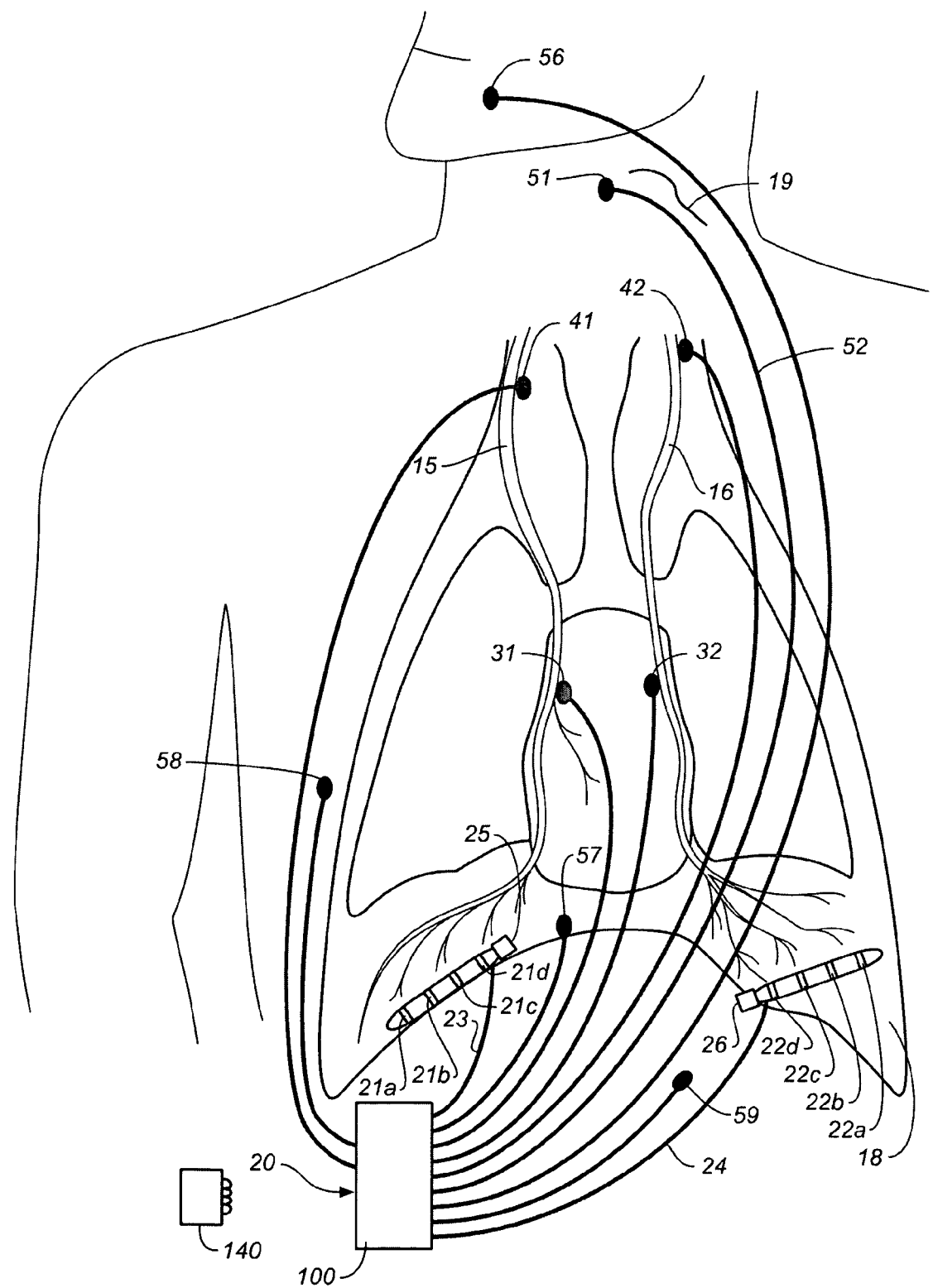
FIG. 1 is a schematic illustration of a device implanted in a subject in accordance with the invention.
Figure 2:
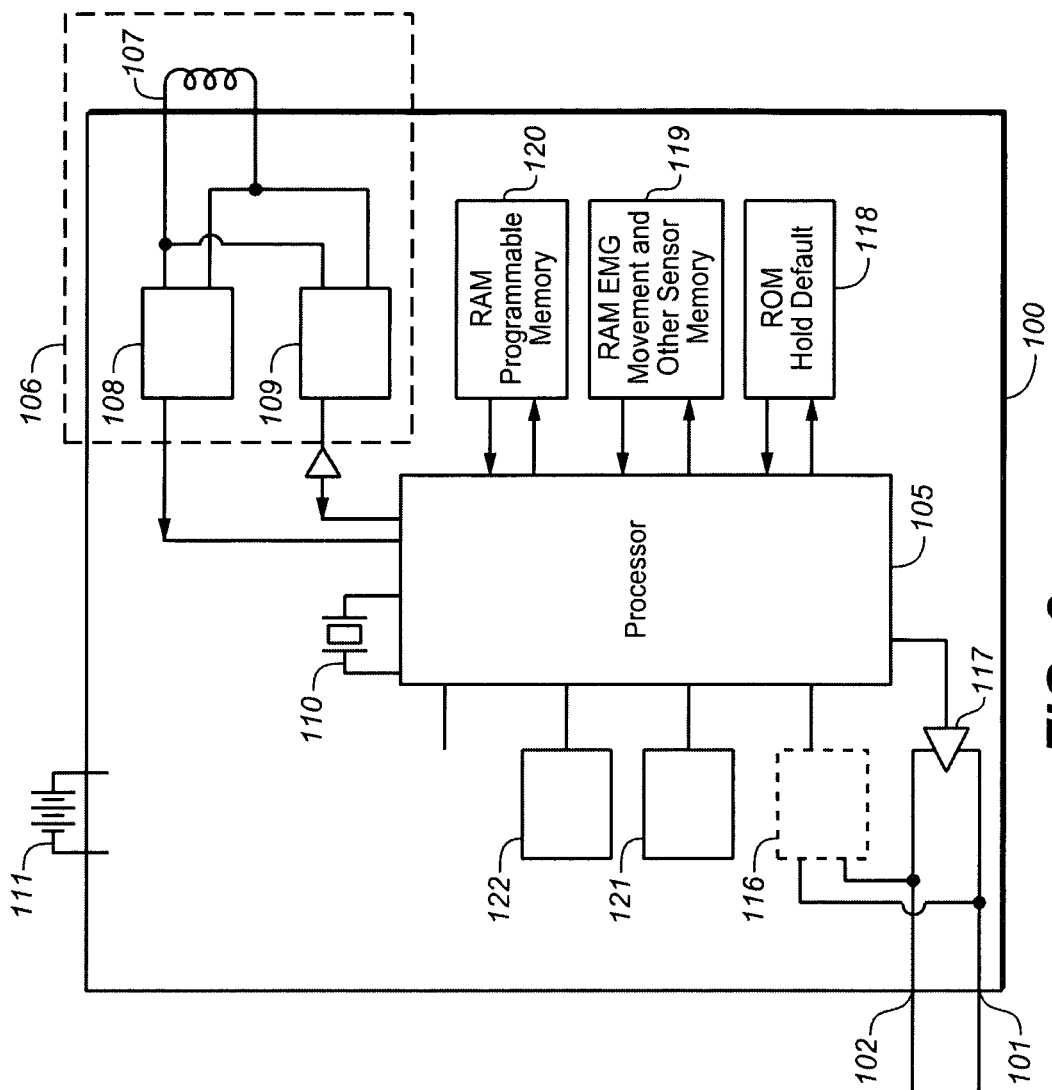
FIG. 2 is a schematic illustration of a processor unit of a sleep breathing disorder treatment device in accordance with the invention.

FIGS. 1 and 2 illustrate a stimulator 20 comprising electrode assemblies 21, 22, each comprising a plurality of electrodes 21a-d and 22a-d respectively. The electrode assemblies 21, 22 are implanted in the diaphragm muscle so that one or more of electrodes 21a-d and of electrodes 22a-d are approximately adjacent to one or more junctions of the phrenic nerves 15, 16, respectively, with the diaphragm 18 muscle. Alternatively or additionally, electrodes or electrode assemblies may be implanted on the diaphragm from the thoracic side, at a location along the phrenic nerve in the thoracic region, neck region or other location adjacent a phrenic nerve (e.g. transvenously) where stimulating the phrenic nerve affects breathing and/or diaphragm movement of the subject. In addition, leads may be subcutaneously placed to stimulate at least a portion of the diaphragm or phrenic nerve. The electrode assemblies 21, 22, 31, 32, 41, 42 described herein are coupled to outputs of a pulse generator and are configured to deliver electrically stimulating signals to tissue associated with the implanted electrode assemblies.

The electrode assemblies 21, 22 (31, 32, 41, 42) may sense as well as pace or electrically stimulate at the diaphragm muscle or at the phrenic nerve (whether internally or externally positioned). Electrode 51 may stimulate (as well as sense) at the upper airway muscles or hypoglossal nerve. Electrode 58 may stimulate (as well as sense) at the chest wall muscles or associated nerves. Electrode 59 may stimulate (as well as sense) at the abdominal muscles or associated nerves. Electrode assemblies 21, 22 may be implanted laparoscopically through the abdomen and into the muscle of the diaphragm 18 with needles, tissue expanding tubes, cannulas or other similar devices. The electrode assemblies 21, 22 may be anchored with sutures, staples, or other anchoring mechanisms. The electrode assemblies 21, 22 may be surface electrodes or alternatively intramuscular electrodes. The leads 23, 24 coupling the electrode assemblies 21, 22 to the control unit 100 are routed subcutaneously to the side of the abdomen where a subcutaneous pocket is created for the control unit 100. The electrode assemblies 21, 22 are each flexible members with electrodes 21a-d, assembled about 1-20 mm apart from one another and electrodes 22a-d assembled about 1-20 mm apart from one another. The electrode assemblies 21, 22 are coupled via leads 23, 24 to control unit 100. The stimulator 20 further comprises one or more sensors configured to sense one or more physiologic parameters. For example one or more sensors such as an accelerometer or movement sensor may sense information regarding movement pattern of the diaphragm muscles, intercostal muscles, and rib movement and thus determine overall respiratory activity and patterns. An electrode or electrodes may be used to sense the EMG of the diaphragm to determine respiration parameters. A flow sensor may be implanted in or near the trachea to sense tracheal air flow. A flow sensor 56 may be implanted in or near the mouth. An intrapleural pressure sensor 57 may be implanted on the top side of the diaphragm on its own or with one or more electrode assemblies 21, 22. The various sensors may be incorporated with electrode assemblies 21, 22, or may be separately implanted or otherwise coupled to the subject.

The control unit 100 is configured to receive and process signals corresponding to sensed physiological parameters, e.g., pressure, flow, nerve activity, diaphragm or intercostal muscle movement, and/or EMG of the diaphragm 18, to determine the respiratory parameters of the diaphragm 18. An EMG signal may be used or other sensed activity may also correspond with either tidal volume or airflow and may be used to identify different portions of a respiration cycle. An example of such signal processing or analysis is described in more detail herein with reference to a sensed respiration correlated signal, such as an EMG, flow, pressure or tidal volume correlated signal, in FIGS. 16A-16D.

The electrodes assemblies 21, 22 are coupled via leads 23, 24 to input/output terminals 101, 102 of a control unit 100. The leads 23, 24 comprise a plurality of electrical connectors and corresponding lead wires, each coupled individually to one of the electrodes 21a-d, 22a-d. Alternatively or in addition, electrodes 31, 32 implanted on or near the phrenic nerve in the thoracic region or electrodes 41, 42 implanted on or near the phrenic nerve in the neck region. Other locations at or near the phrenic nerve may be stimulated as well. Electrode (s) 51, may be placed at or near the hypoglossal nerve in accordance with a variation of the invention where stimulation of the diaphragm is coordinated with activation of upper airway muscles to open the airway passage just prior to stimulating the diaphragm muscles. Electrode(s) 51 is (are) coupled through lead(s) 52 to electronics in control unit 100. Control unit 100 is also configured to receive information from one or more sensors, including, for example upper airway pressure sensor 56 or intrapleural pressure sensor 57. Alternatively or in addition, electrode(s) 58 may be implanted at or near the chest wall muscles or associated nerves and may be used to stimulate chest wall muscles in coordination with diaphragm stimulation. According to one aspect, the chest wall stimulation may augment diaphragm stimulation to enhance breathing or lung volume control. Alternatively or in addition, electrode(s) 59 may be implanted at or near one or more abdominal muscle groups or associated nerves and may be used to stimulate abdominal muscles in coordination with diaphragm stimulation. According to one aspect, the abdominal muscle stimulation may augment diaphragm stimulation to enhance breathing or lung volume control. Chest wall and/or muscle stimulation may be used and coordinated with diaphragm stimulation to reduce paradoxical movement when diaphragm stimulation is being used.

The control unit 100 is implanted subcutaneously within the patient, for example in the chest region on top of the pectoral muscle. The control unit may be implanted in other locations within the body as well. The control unit 100 is configured to receive sensed nerve electrical activity from the sensors or electrode assemblies 21, 22, (31, 32, 41, 42, 51, 57, 58, 59) corresponding to respiratory effort or other respiration related parameters of a patient. The control unit 100 is also configured to receive information corresponding to other physiological parameters as sensed by other sensors. The control unit 100 delivers stimulation to the nerves 15, 16 or diaphragm as desired in accordance with the invention. The control unit 100 may also deliver stimulation to the hypoglossal nerve 19 as described for example in U.S. application Ser. No. 11/480,074. The control unit 100 may determine when to stimulate the diaphragm as well as specific stimulation parameters, e.g., based on sensed information. The control unit 100 may determine when to stimulate the chest wall or abdominal muscles, as well as specific stimulation parameters, e.g., based on sensed information.

Figure 16A:
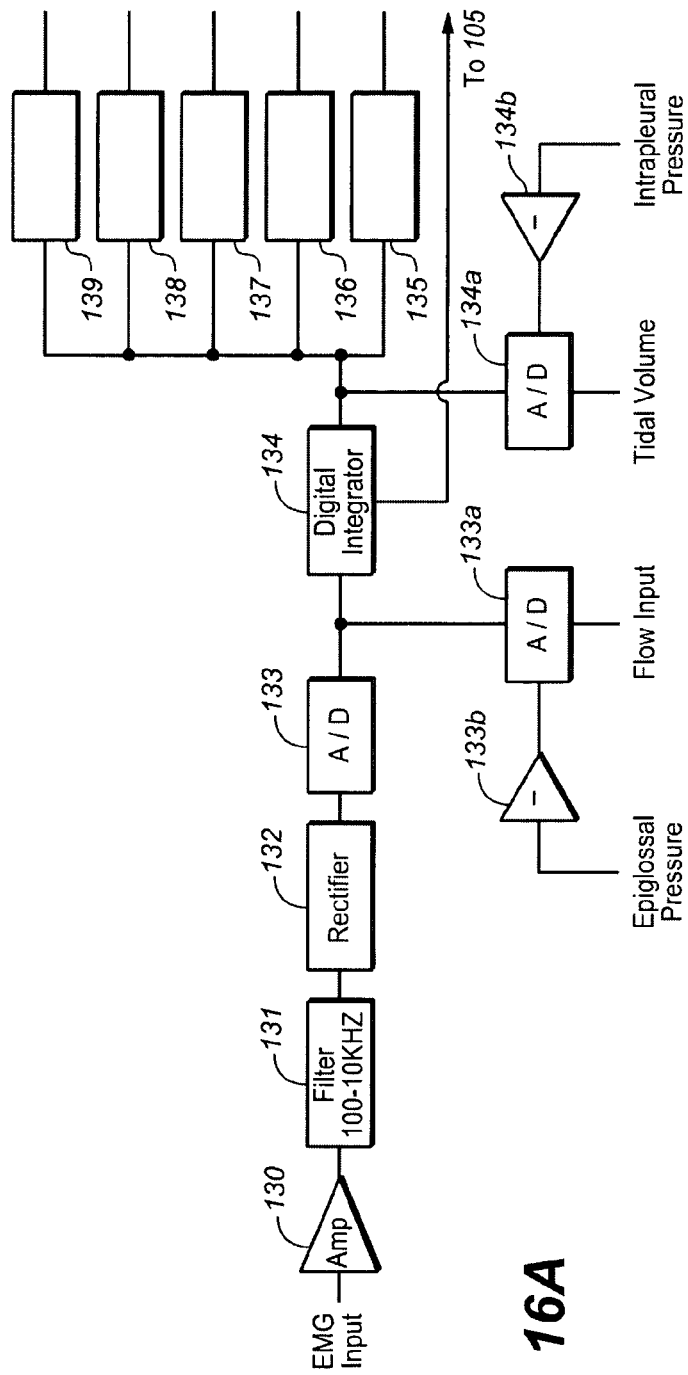
FIG. 16A is a schematic of a signal processor of the processor unit in accordance with the invention.

Additional sensors may comprise movement detectors 25, 26, in this example, strain gauges or piezo-electric sensors included with the electrode assemblies 21, 22 respectively and electrically connected through leads 23, 24 to the control unit 100. The movement detectors 25, 26 detect movement of the diaphragm 18 and thus the respiration parameters. The movement detectors 25, 26 sense mechanical movement and deliver a corresponding electrical signal to the control unit 100 where the information is processed by the processor 105. The movement information may correlate to airflow and may accordingly be used to determine related respiration parameters. Upper airway pressure sensor 56 is positioned for example in the mouth or trachea and provides a signal that may be correlated to flow inverse of flow. Intrapleural pressure sensor 57 provides a signal that is schematically illustrated in FIG. 16E and is generally correlated to the inverse of tidal volume. The signal from the positive airway pressure sensor and the intrapleural pressure sensor may be processed and used for example, as described with respect to FIGS. 16A and 16B.

Electrodes may be selected from the plurality of electrodes 21a-d and 22a-d once implanted, to optimize the stimulation response. Electrodes may also be selected to form bipolar pairs or multipolar groups to optimize stimulation response. Alternatively electrodes may be in a monopolar configuration. Testing the response may be done by selecting at least one electrode from the electrodes in an assembly or any other combination of electrodes to form at least one closed loop system, by selecting sequence of firing of electrode groups and by selecting stimulation parameters. The electrodes may be selected by an algorithm programmed into the processor that determines the best location and sequence for stimulation and/or sensing nerve and/or EMG signals, e.g., by testing the response of the electrodes by sensing respiratory effort or flow in response to stimulation pulses. Alternatively, the selection process may occur using an external programmer that telemetrically communicates with the processor and instructs the processor to cause stimulation pulses to be delivered and the responses to be measured. From the measured responses, the external programmer may determine the optimal electrode configuration, by selecting the electrodes to have an optimal response to delivery of stimulation.

Alternative mapping techniques may be used to place one or more stimulation electrodes on the diaphragm. Examples of mapping the diaphragm and/or selecting desired locations or parameters for desired stimulation responses are described for example in U.S. application Ser. No. 10/966,484 filed Oct. 15, 2004 and entitled: SYSTEM AND METHOD FOR MAPPING DIAPHRAGM ELECTRODE SITES; in U.S. application Ser. No. 10/966,474, filed Oct. 15, 2004 entitled: BREATHING THERAPY DEVICE AND METHOD; in U.S. application Ser. No. 10/966,472 filed Oct. 15, 2004 entitled: SYSTEM AND METHOD FOR DIAPHRAGM STIMULATION; U.S. application Ser. No. 10/966,421 filed Oct. 15, 2004 entitled: BREATHING DISORDER AND PRECURSOR PREDICTOR AND THERAPY DELIVERY DEVICE AND METHOD; and in U.S. application Ser. No. 10/686,891 filed Oct. 15, 2003 entitled BREATHING DISORDER DETECTION AND THERAPY DELIVERY DEVICE AND METHOD, all of which are fully incorporated herein by reference.

Any of the electrodes described in this application may be powered by an external source, e.g., an external control unit. Additionally, any of the electrodes herein may alternatively be microstimulators, including, for example, implanted microstimulators with electronic circuitry; and an external power source, e.g. an RF coupled source. In addition, percutaneous and transcutaneous stimulation may be used in accordance with various aspects of the invention.

FIG. 2 illustrates an implantable control unit 100. The control unit 100 includes electronic circuitry capable of generating and/or delivering electrical stimulation pulses to the electrodes or electrode assemblies 21, 22, 31, 32, 41, 42, through leads 23, 24, 33, 34, 43, 44, respectively, to cause a diaphragm respiratory response in the patient. The control unit 100 electronic circuitry is also configured to generate and/or deliver electrical stimulation to electrode 51, through lead 52, to cause an upper airway response such as increased tonicity and/or opening of upper airway (electrode 51 may also comprise a pair of bipolar electrodes). For purposes of illustration, in FIG. 2, the control unit 100 is shown coupled through leads 23, 24 to electrode assemblies 21, 22 respectively. Other leads as described herein may be connected to inputs 101, 102 or other inputs.

The control unit 100 comprises a processor 105 for controlling the operations of the control unit 100. The processor 105 and other electrical components of the control unit are coordinated by an internal clock 110 and a power source 111 such as, for example a battery source or an inductive coupling component configured to receive power from an inductively coupled external power source. The processor 105 is coupled to a telemetry circuit 106 that includes a telemetry coil 107, a receiver circuit 108 for receiving and processing a telemetry signal that is converted to a digital signal and communicated to the processor 105, and a transmitter circuit 109 for processing and delivering a signal from the processor 105 to the telemetry coil 107. The telemetry coil 107 is an RF coil or alternatively may be a magnetic coil. The telemetry circuit 106 is configured to receive externally transmitted signals, e.g., containing programming or other instructions or information, programmed stimulation rates and pulse widths, electrode configurations, and other device performance details. The telemetry circuit is also configured to transmit telemetry signals that may contain, e.g., modulated sensed and/or accumulated data such as sensed EMG activity, sensed flow or tidal volume correlated activity, sensed nerve activity, sensed responses to stimulation, sensed position information, sensed movement information and episode counts or recordings.

The leads 23, 24 are coupled to inputs 101, 102 respectively, of the control unit 100, with each lead 23, 24 comprising a plurality of electrical conductors each corresponding to one of the electrodes or sensors (e.g., movement sensor) of the electrode assemblies 23, 24. Thus the inputs 101, 102 comprise a plurality of inputs, each input corresponding to one of the electrodes or sensors. The signals sensed by the electrode assemblies 21, 22 are input into the control unit 100 through the inputs 101, 102. Each of the inputs are coupled to a separate input of a signal processing circuit 116 (schematically illustrated in FIG. 2 as one input) where the signals are then amplified, filtered, and further processed, and where processed data is converted into a digital signal and input into the processor 105. Each signal from each input is separately processed in the signal processing circuit 116.

The EMG/Phrenic nerve sensing has a dual channel sensor. One corresponding to each lung/diaphragm side. However, sensing can be accomplished using a single channel as the brain sends signals to the right and left diaphragm simultaneously. Alternatively, the EMG or phrenic nerve collective may be sensed using a single channel. Either a dual channel or single channel setting may be used and programmed.

The control unit 100 further includes a ROM memory 118 coupled to the processor 105 by way of a data bus. The ROM memory 118 provides program instructions to the control unit 100 that direct the operation of the stimulator 20. The control unit 100 further comprises a first RAM memory 119 coupled via a data bus to the processor 105. The first RAM memory 119 may be programmed to provide certain stimulation parameters such as pulse or burst morphology; frequency, pulse width, pulse amplitude, duration and a threshold or trigger to determine when to stimulate or how to coordinate stimulation of one or more muscle groups. A second RAM memory 120 (event memory) is provided to store sensed data sensed, e.g., by the electrodes of one or more electrode assemblies 21, 22 (EMG or nerve activity), position sensor 121, diaphragm movement sensors or strain gauges 25, 26, or the accelerometer 122 or other sensors such as flow or tidal volume correlated sensors (e.g. using movement sensors or impedance plethysmography with a sensor positioned at one or more locations in the body such as on the control unit 100. These signals may be processed and used by the control unit 100 as programmed to determine if and when to stimulate or provide other feedback to the patient or clinician. Also stored in RAM memory 120 may be the sensed waveforms for a given interval, and a count of the number of events or episodes over a given time as counted by the processor 105. The system's memory will be programmable to store information corresponding to breathing parameters or events, stimulation delivered and responses, patient compliance, treatment or other related information. These signals and information may also be compiled in the memory and downloaded telemetrically to an external device 140 when prompted by the external device 140.

An example of the circuits of the signal processing circuit 116 corresponding to one or more of the sensor inputs is illustrated schematically in FIG. 16A. A sensor input signal correlating or corresponding to EMG, tidal volume or flow is input into an amplifier 130 that amplifies the signal. The signal is then filtered to remove noise by filter 131. The amplified signal is rectified by a rectifier 132, is converted by an A/D converter 133 and then is integrated by integrator 134 to result in an integrated signal from which respiratory information can be ascertained. A flow correlated signal may be input through A/D converter 133a and then input through the integrator 134. A signal corresponding to upper airway (or epiglossal) pressure may also be used as a flow correlated signal by inverting an upper airway pressure signal with inverter 133b and inputting the signal through A/D converter 133a. The signal output of the integrator 134 is then coupled to the processor 105 and provides a digital signal corresponding to the integrated waveform to the processor 105. A tidal volume correlated signal or an intrapleural pressure correlated signal may also be input to the signal processing circuit through A/D converter 134a at the output of the integrator 134. Intrapleural pressure may first be inverted through inverter 134b before inputting into A/D converter 134a The signal output of the integrator 134 is coupled to a peak detector 135 that determines when the inspiration period of a respiratory cycle has ended and an expiration cycle has begun. The signal output of the integrator 134 is further coupled to a plurality of comparators 136, 137. The first comparator 136 determines when respiration has been detected based on when an integrated signal waveform amplitude has been detected that is greater than a percentage value of the peak of an intrinsic respiratory cycle or another predetermined amount (comp 1), for example between 1-25% of the intrinsic signal. In this example, the comparator is set at a value that is 10% of the waveform of an intrinsic respiratory cycle. The second comparator 137 determines a value of the waveform amplitude (comp 2) when an integrated signal waveform amplitude has been detected that is at a predetermined percentage value of the peak of an intrinsic respiratory cycle or another predetermined amount, for example between 75%-100% of the intrinsic signal. In this example, the comparator is set at a value that is 90% of the waveform of an intrinsic respiratory cycle. From this value and the comp 1 value, the slope of the inspiration period (between 10% and 90% in this example) may be determined. This slope may provide valuable diagnostic information as it shows how quickly a patient inhales.

In the case of a signal correlating to flow that is integrated or a signal correlated to tidal volume, after (or when) the peak detector detects the end of an inhalation period and the beginning of an exhalation period, the third comparator 138 determines an upper value for the waveform amplitude during active exhalation period, for example between 100% and 75% of the peak value detected by the peak detector 135. Then a lower value (comp 4) of the waveform during the exhalation period is determined by the fourth comparator 139, which compares the measured amplitude to a predetermined value, e.g. a percentage value of the peak amplitude. In this example, the value is selected to be 10% of the peak value. In one embodiment this value is selected to roughly coincide with the end of a fast exhalation period. From comp 3 and comp 4 values, the slope of the exhalation period (between 10% and 90% in this example) may be determined. This slope may provide valuable diagnostic information as it shows how quickly a patient exhales.

A non-integrated flow signal may also be used, for example in conjunction with EMG to detect airway closure where EMG is present in the absence of flow. An upper airway pressure signal is correlated with flow, so the absence of negative deflection corresponding to inhalation indicates airway closure. In accordance with another aspect of the invention, stimulation may be triggered where there is a flow limitation as opposed to an obstruction. Flow limitation may also be detected with diaphragm EMG increase and/or reduction or flattening of peak flow of the flow waveform. EMG may be used to detect flow obstructions or flow limitations, or to differentiate between obstructions and limitations or degrees thereof. An increase in EMG indicating an increase in effort, may be used where the increase for flow limitation is less than that of an obstruction. According to one aspect, a calculation of the running average of the peak EMG envelope may be made where stimulation is triggered when the current EMG envelope crosses a flow limitation threshold indicating flow limitation. Accordingly, where a degree of flow limitation indicates a degree of ventilatory instability or arousals occurring, stimulation may be triggered. Such flow limitation detection thresholds may be determined on a patient by patient basis, for example by observing a patient in sleep and then programming the device according to a patient's individual sleep and respiration patterns.

The intrapleural pressure signal is generally (correlated with) the inverse of tidal volume. Intrapleural pressure may be used to provide diagnostic information such as lung volume information, duration of respiratory cycles, and rate of inhalation and exhalation.

Intrapleural pressure may be used by setting threshold levels used to determine different phases of a respiration cycle. For example, the negative peak 175a of intrapleural pressure correlates generally with the start of the exhalation cycle. This point 175a or other information derived from the sensed signal (FIG. 16E) may be used to trigger stimulation in accordance with one or more stimulation protocols of the embodiments of the invention described herein.

The information ascertained from the sensed signals may be used to determine triggers for providing stimulation.

Examples of such triggers are described with reference to the various stimulation protocols and techniques described in the various embodiments herein.

FIG. 16B illustrates two sequential integrated waveforms of exemplary integrated signals corresponding to two serial respiratory cycles. An inspiration portion 172 may be observed using an EMG, flow or tidal volume correlated signal. An exhalation period 176 may be observed using a flow or tidal volume correlated signal. The waveform 170 has a baseline 170b, inspiration cycle 171, a measured inspiration cycle 172, a point of 10% of peak inspiration 173 (comp 1), a point of 90% of peak of inspiration 174 (comp 2), a peak 175 where inspiration ends and exhalation begins, and exhalation cycle 176 a fast exhalation portion 177 of the exhalation cycle 176, a 90% of peak exhalation point 178 (comp 3), a 10% of peak exhalation point 179 (comp 4), an actual respiratory cycle 180 and a measured respiratory cycle 181. The second waveform 182 is similarly shaped. The 10% inspiration 183 of the second waveform 182 marks the end of the measured respiratory cycle 181, while the 10% point 173 of the waveform 170 marks the beginning of the measured respiratory cycle 181. A tidal volume correlated signal as illustrated in FIG. 16B and other illustrations herein showing tidal volume, show tidal volume with a baseline zeroed from a reference point of an initial end expiratory lung volume such baseline which is know to one of ordinary skill in the art as a minimum lung volume or functional residual capacity. Techniques for changing that baseline are described and illustrated herein.

FIG. 16C illustrates a schematic EMG envelope corresponding to an inspiration portion e.g., 172 of a respiration cycle. FIG. 16D illustrates a schematic flow correlated signal corresponding to a respiration cycle.

The upper airway pressure sensed with sensor 56 provides a signal correlated to the inverse of flow. The inverse of the upper airway signal may be processed as a flow correlated signal as set forth herein to provide respiration information.

Intrapleural pressure may be sensed with sensor 57 to provide a signal as schematically set forth in FIG. 16E. This may be processed similarly to an integrated flow (or Tidal Volume signal) as described herein to provide exhalation cycle information or lung volume information. Exhalation cycle information or lung volume information may be used as a trigger for stimulation as set forth herein.

Figure 3:
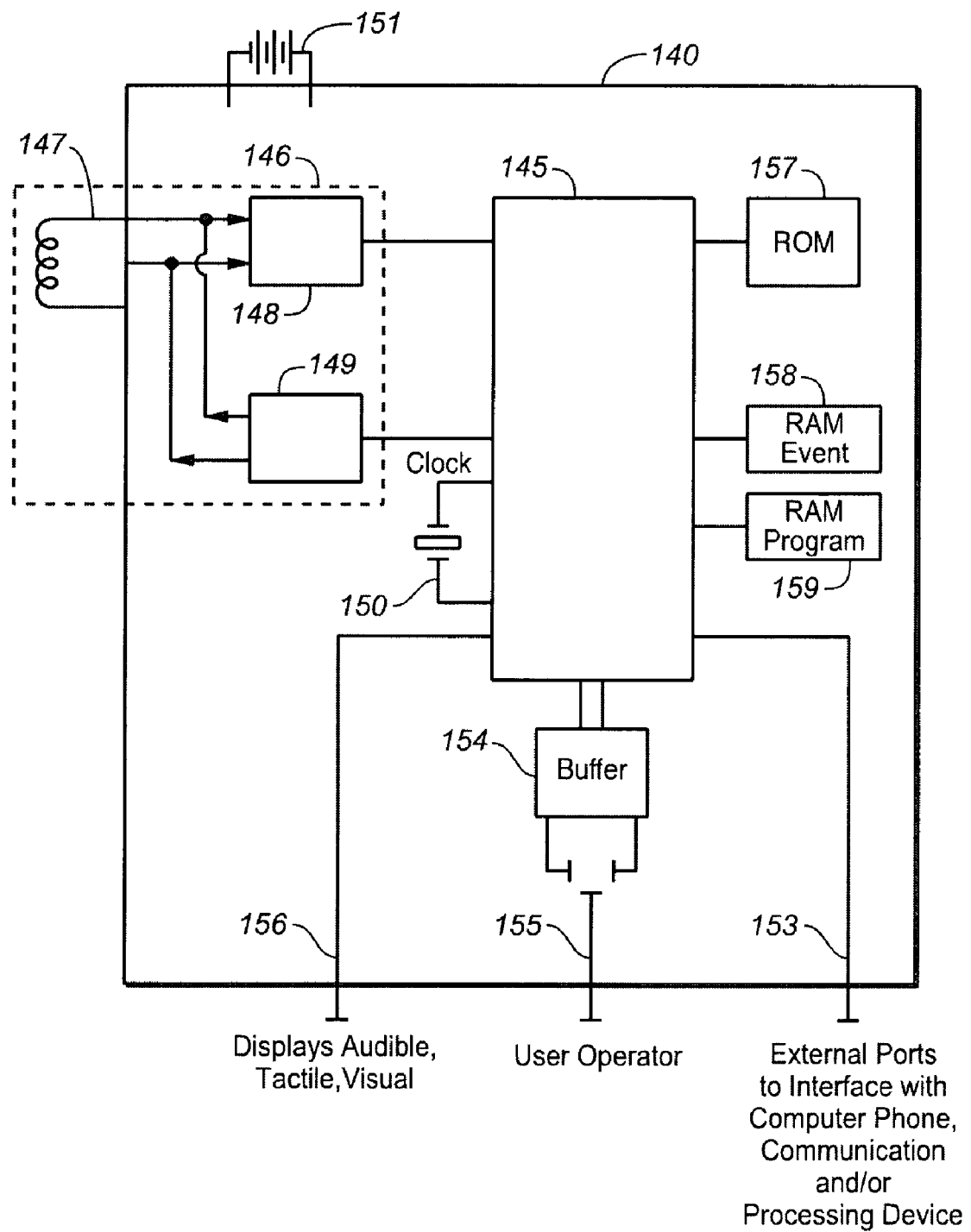
FIG. 3 is a schematic illustration of an external device of a stimulator in accordance with the invention.

In FIG. 3 a circuit for an external device 140 is illustrated. The external device 140 comprises a processor 145 for controlling the operations of the external device. The processor 145 and other electrical components of the external device 140 are coordinated by an internal clock 150 and a power source 151. The processor 145 is coupled to a telemetry circuit 146 that includes a telemetry coil 147, a receiver circuit 148 for receiving and processing a telemetry signal that is converted to a digital signal and communicated to the processor 145, and a transmitter circuit 149 for processing and delivering a signal from the processor 145 to the telemetry coil 146. The telemetry coil 147 is an RF coil or alternatively may be a magnetic coil depending on what type of coil the telemetry coil 107 of the implanted control unit 100 is. The telemetry circuit 146 is configured to transmit signals to the implanted control unit 100 containing, e.g., programming or other instructions or information, programmed stimulation protocols, rates and pulse widths, electrode configurations, and other device performance details. The telemetry circuit 146 is also configured to receive telemetry signals from the control unit 100 that may contain, e.g., sensed and/or accumulated data such as sensed information corresponding to physiological parameters, (e.g., sensed EMG activity, sensed nerve activity, sensed responses to stimulation, sensed position information, sensed flow, or sensed movement information). The sensed physiological information may be stored in RAM event memory 158 or may be uploaded and through an external port 153 to a computer, or processor, either directly or through a phone line or other communication device that may be coupled to the processor 145 through the external port 153. The external device 140 also includes ROM memory 157 for storing and providing operating instructions to the external device 140 and processor 145. The external device also includes RAM event memory 158 for storing uploaded event information such as sensed information and data from the control unit, and RAM program memory 159 for system operations and future upgrades. The external device also includes a buffer 154 coupled to or that can be coupled through a port to a user-operated device 155 such as a keypad input or other operation devices. Finally, the external device 140 includes a display device 156 (or a port where such device can be connected), e.g., for display visual, audible or tactile information, alarms or pages.

The external device 140 may take or operate in, one of several forms, e.g. for patient use, compliance or monitoring; and for health care provider use, monitoring, diagnostic or treatment modification purposes. The information may be downloaded and analyzed by a patient home unit device such as a wearable unit like a pager, wristwatch or palm sized computer. The downloaded information may present lifestyle modification, or compliance feedback. It may also alert the patient when the health care provider should be contacted, for example if there is malfunctioning of the device or worsening of the patient's condition.

Other devices and methods for communicating information and/or powering stimulation electrodes as are know in the art may be used as well, for example a transcutaneously inductively coupled device may be used to power an implanted device.

According to one aspect of the invention, the stimulator operates to stimulate and/or manipulate breathing to mitigate (i.e., avoid or reduce effects of) an obstructive respiratory event by stimulating the phrenic nerve, diaphragm or associated tissue according to one or more protocols, to elicit a respiratory response. Examples of such stimulation protocols are described herein with reference to FIGS. 4A-24C. In accordance with another aspect of the invention, such stimulation is provided prior to the onset of an obstructive respiratory event or prior to airway obstruction to prevent an obstructive respiratory event from occurring or the airway from fully closing. In accordance with another aspect of the invention, stimulation is provided at a low level following obstructive sleep apnea or effective airway closure.

According to an aspect, one or more protocols or examples described herein are used to treat one or more diseases, disorders or conditions, for example as described herein.

In accordance with one aspect of the invention as described with respect to FIGS. 4A-4D, 5A-5C, 7A-7B, 8A-8B, 9A-9C, 10A-10C, 12A-12B, 18A-18C, 19A-19C, 20A-20C and 21A-21C, stimulation of the phrenic nerve or diaphragm is provided to increase functional residual capacity, i.e., end expiratory volume, at least until onset of a subsequent respiration cycle. In accordance with the invention, an increased functional residual capacity is believed to assist in maintaining an airway passage open to a sufficient degree to prevent or reduce airway collapse that results in an obstructive respiratory event. Increased functional residual capacity may also improve gas exchange, airway tonicity, and ventilatory stability and treat one or more diseases, disorders or conditions described herein.

In accordance with another aspect of the invention as described with respect to FIGS. 18A-24C, stimulation of the phrenic nerve or diaphragm is provided to stabilize functional residual capacity. Among other effects, stabilizing functional residual capacity is believed to stabilize ventilation, improve upper airway patency, stabilize the upper airway and/or improve gas exchange.

In accordance with another aspect of the invention, as described with respect to FIG. 4A-4D, 5A-5B, 6A-6B, 10A-10C, 11A-11B, 12A-12B or 14A-14B, stimulation of the phrenic nerve or diaphragm is provided to increase tidal volume sufficiently to increase upper airway patency. It is believed that increasing the tidal volume may contribute to stiffening the upper airway. Preferably the same or a lower peak flow with respect to intrinsic flow is provided to avoid an increase in negative pressure applied to the upper airway that would decrease upper airway patency. Therapy may be delivered to increase flow in the case where flow is below normal. In cases where flow is normal, or limited by obstruction, tidal volume may be increased through extension of the inspiration duration. An upper airway hysteresis effect may also occur where the volume of a breath is increased above a normal tidal volume and the stiffening of the upper airway during inspiration does not return entirely to a relaxed resting state. It is accordingly additionally believed that an upper airway hysteresis effect would stiffen the upper air passageway for subsequent breaths and will thereby prevent or mitigate airway narrowing or collapse that results in obstructive sleep apnea. Increasing tidal volume may also improve $O_2$ saturation, and stabilize respiratory drive. Also increasing FRC may mechanically stabilize the upper airway by creating a greater tension one the airway than with a relatively lower FRC.

In accordance with another aspect of the invention, as described with respect to FIGS. 4A-4D, 6A-6C, 9A-9C and 10A-10C, 11A-11B, 12A-12B, 14A-14B, 18A-18C, 19A-19C, 20A-20D, 21A-21D, 22A-22C, 23A-23C, and/or 24A-24C, stimulation of the phrenic nerve or diaphragm is provided during intrinsic breathing during or at the end of an intrinsic inspiration portion of a breathing cycle. For purposes of the invention herein, the intrinsic cycle may be detected near onset of inspiration. Other portions of a breathing cycle may be identified for breathing stimulation. Alternatively, the beginning of the breathing cycle or a portion of the breathing cycle may be predicted, e.g., based on a typical breathing pattern of an individual patient.

A stimulation signal may be provided during inspiration of intrinsic breathing for various purposes. In accordance with a variation of the invention, stimulation is provided during intrinsic inspiration to provide initial and more gradual control of breathing according to a protocol. Then, breathing control protocols may be applied so that airway closure due to stimulation is avoided. Tidal volume is increased gradually so as to balance out an increase in upper airway resistance that can occur with stimulation during intrinsic inspiration. Stimulation of breathing during intrinsic inspiration in accordance with variations of the invention is configured to contribute to creating the effect of increasing functional residual capacity. In some variations of the invention, stimulation during intrinsic breathing is configured to stiffen the upper airway, thereby increasing upper airway patency. Stimulating during inspiration in accordance with a protocol of the invention may also increase upper airway hysteresis. In one embodiment, breathing is stimulated at least in part during intrinsic inspiration so that the resulting tidal volume is greater than intrinsic normal volume, while peak flow is maintained near normal peak flow to avoid upper airway closure. Stimulating during intrinsic inspiration may also be used to normalize breathing in an obstructive sleep apnea patient and to increase ventilatory stability associated with airway obstructions. Stimulating at least in part during intrinsic inspiration may increase inspiration duration which may allow increase of tidal volume without significantly increasing the peak flow. (Increasing peak flow may increase the possibility of airway closure.) According to one embodiment, peak flow is provided at, near or below intrinsic peak flow.

While stimulating breathing during intrinsic inspiration is described herein in use with a device and method of treating obstructive sleep apnea, other breathing related disorders, or other diseases, disorders or conditions, may be treated by stimulating breathing during intrinsic inspiration in accordance with another aspect of the invention.

In accordance with one aspect of invention, stimulation may be provided whereby stimulation may elicit a diaphragm muscle contraction or contractions that are added to intrinsic contraction, i.e., that add to the intrinsic diaphragm EMG. Such added muscle contraction may be provided during inspiration, during exhalation, or during both inspiration and exhalation of a respiratory cycle. Such added muscle contraction may be used to increase inspiration duration or extend inspiration. Such stimulation may also be used to extend or to shorten the exhalation (non-inspiration) duration. According to one aspect, stimulation may provide a high frequency of muscle contraction, i.e., at a frequency greater than one per respiratory cycle. A twitch stimulation may be used to achieve high frequency contractions. The amplitude and pulse duration, and to some extent frequency, may vary depending upon the location and method of diaphragm stimulation. According to another aspect, one or more short, fast muscle contraction stimulations may be provided during a respiration cycle. Such short fast stimulation is generally shorter in duration than that which would elicit a normal intrinsic breath. Such short fast stimulation may be configured to elicit a plurality of additional gas exchanges within or supplemental to an intrinsic breath. Such short fast muscle contraction stimulation may be configured to elicit short fast breaths. The stimulation may increase blood oxygen saturation levels, stabilize ventilation or breathing, increase lung volume, increase FRC, increase tidal volume and or provide a lung volume bias.

In accordance with another aspect of the invention and as illustrated in FIGS. 4A-4D, and 5A-5C the phrenic nerve or diaphragm is stimulated to provide deep inspiration therapy to a subject. Deep inspiration therapy involves stimulating a breath that is of a greater tidal volume than a normal breath. According to a preferred embodiment, deep inspiration stimulation provides a breath having a greater inspiration duration than that of a normal breath. Rather than substantially increasing peak flow or rather than increasing the magnitude of diaphragm contraction, the increase in inspiration duration to increase tidal volume is believed to reduce the likelihood of airway closure with stimulation. Deep inspiration stimulation may be provided intermittently throughout the night or a portion of the night while a patient sleeps, thus preventing an obstructive respiratory event. While deep inspiration therapy is described herein in use with a device and method of treating obstructive sleep apnea, other breathing or related disorders may be treated by deep inspiration therapy.

In accordance with another aspect of the invention as described with respect to FIGS. 6A-6B, 7A-7B, 8A-8B, 9A-9C, 10A-10C, 12A-12B 18A-18C, 19A-19C, 20A-20D, 21A-21D, 22A-22C, 23A-23C, and 24A-24C, the exhalation cycle is manipulated to provide a therapeutic effect. According to one aspect of the invention, increased functional residual capacity is provided by manipulating the exhalation phase. Manipulation of the exhalation phase may be provided using stimulation during the exhalation phase. The exhalation phase may also be manipulated in length or duration. Manipulation may be provided with sustained or twitch contractions as described herein. An increase in duty cycle may be used to manipulate exhalation. Changing the inspiration parameters may also manipulate exhalation. Manipulation of length or duration of inspiration, exhalation or the ratio may thereby manipulate exhalation.

In accordance with another aspect of the invention as described with respect to FIGS. 7A-7B 8A-8B, 9A-9C, 10A-10C, 18A-18C, 19A-19C, 20A-20C and 21A-21C, a stimulation is applied during all or a portion of the respiration cycle to create a lung volume bias. Among other therapeutic effects such stimulation may increase functional residual capacity. Such stimulation may be directed to provide an increased lung volume during a rest phase (end portion of exhalation) of a respiration cycle by sustaining a contraction of the diaphragm. Such stimulation may also provide contractions that result in biasing lung volume. This level of stimulation may vary from patient to patient and may be determined on an individual basis. It may also depend on electrode type and placement. Stimulation may be at a low energy, i.e., lower than that which elicits a normal intrinsic breath.

In accordance with another aspect of the invention, as described with respect to FIGS. 9A-9C, 12A-12B, 13A-13B, and 14A-14B, stimulation of the phrenic nerve or diaphragm is provided to control breathing. According to one aspect of the invention, breathing is controlled either by inhibiting respiratory drive, entraining breathing or other mechanisms. Controlling breathing according to one variation comprises stimulating to control or manipulate the central respiratory drive. Controlling breathing may include taking over breathing to control one or more parameters of a stimulated breath. Entraining breathing may include stimulating at a rate greater than but close to, or equal to the intrinsic respiratory rate until the central pattern generator activates the respiration mechanisms, which includes those of the upper airway, in phase with the stimulation. As an alternative or in addition, inspiration duration may be increased with respect to the total respiration cycle or exhalation. While controlling breathing is described herein in use with a device and method of treating obstructive sleep apnea, other breathing or related disorders may be treated by controlling breathing in accordance with another aspect of the invention. For example, stimulation at a certain time during an intrinsic breathing cycle may trigger an intrinsic breath through reflex mechanisms, and the timing of the stimulus may lead to an entrained central drive. The reflexes may be triggered by induced lung volume changes and may be vagally mediated. In addition to controlling breathing or entraining breathing by initially taking over breathing, breathing may be controlled or entrained using a low energy stimulation of diaphragm or phrenic nerve to trigger these reflexes and/or afferent nerve transmission or otherwise affect central respiratory drive.

According to another aspect of the invention stimulation is used to provide ventilatory stability. Examples of providing ventilatory stability are shown in FIGS. 4A-4D, 5A-5C, 6A-6C, 7A-7B, 8A-8B, 9A-9C, 10A-10B, 11A-11B, 12A-12C 13A-13B, 14A-14B, 18A-18C, 19A-19C, 20A-20D and 21A-21D. "Ventilatory instability is defined herein to mean varying breathing rate, flow, functional residual capacity and/or tidal volume outside of normal variations." Improving ventilatory stability may lead among other things, to avoidance of upper airway obstruction or flow limitations, reduced central apneas, normalized blood gases, increased $O_2$ saturation levels, reduced arousals, reduced sympathetic bias, improved hemodynamics, improved heart function, better sleep quality as well as other improvements in one or more diseases, disorders or conditions, for example, as set forth herein.

Ventilatory stability may be provided by stabilizing the upper airway or by influencing respiratory drive. Ventilatory stability may be provided by controlling breathing in a manner that creates stability in flow, or FRC as well as other respiratory related parameters such as blood gas levels or oxygen desaturations. Ventilatory stability may be provided by entraining breathing. Ventilatory stability may be provided by stimulating breathing to increase a falling tidal volume towards that of a normal breath. Increased ventilatory stability may also be provided by increasing FRC. An increased FRC may reduce minute ventilation by reducing the tidal volumes and therefore providing an increased $PCo2$. Other stimulation may be provided to increase $PCO2$ as well, for example by controlling minute ventilation, exhalation or inspiration and other manners. An increased $PCo2$ will move the $Co2$ levels away from the apnea threshold which is raised during sleep. When the $Co2$ apnea threshold is crossed, it is believed that central drive is reduced often followed by an overshoot (hyperventilation) response if chemoreceptor activation is delayed. Such instability may take the form of one or more types of periodic or unstable breathing. This and other ventilatory instability may be treated or reduced by increasing FRC or improving ventilation for a period of time whereby the stabilizing affects continue for at least some time following the period of stimulation. Stimulation may also be provided to stabilize upper airway to thereby increase ventilatory stability. In accordance with this aspect, stimulation may be provided to increase upper airway stability as described herein to provide a mechanical tension on the airway to stabilize it.

Ventilatory instability can be associated with obstructive respiratory events and can include, for example, variations in breathing rate and/or tidal volume associated with sleep onset, change in sleep state, and REM sleep, or increased obstruction due to positioning while sleeping. According to one aspect, stimulation is provided to create ventilatory stability and to thereby reduce fluctuations in the upper airway passage muscles that may lead to upper airway collapse where ventilatory drive is low or unstable. Stimulation may be provided to physically stabilize the upper airway by increasing FRC or by creating upper airway hysteresis as described herein. Also, instability in ventilatory rate that indicates the onset of obstructive sleep apnea may be treated by controlling breathing, e.g., for a preset period of time.

Instability in ventilatory rate may be treated by normalizing tidal volume using stimulation as described with respect to FIG. 10A-10B, 11A-11B, 18A-18C, 19A-19C, 20A-20C or 21A-21C. Instability in ventilatory rate may be treated by increasing FRC as described for example with respect to FIGS. 4A-4D, 5A-5C, 7A-7B, 8A-8B, 9A-9C, 10A-10B, 11A-11B,12A-12C 13A-13B, 14A-14B, 18A-18C, 19A-19C, 20A-20D and 21A-21D. Instability in ventilatory rate may also be treated by normalizing or stabilizing FRC as described with respect to FIG. 18A-18C, 19A-19C, 20A-20D or 21A-21D. Examples of normalization or stabilization of oxygen desaturations are illustrated in FIGS. 20A-20D and 21A-21D. Instability in ventilation may be treating by controlling or entraining breathing, for example as set forth with respect to FIGS. 9A-9C, 12A-12B, 13A-13B, and 14A-14B.

Referring to FIGS. 4A-4D, stimulation and respiration waveforms illustrating a method using a device in accordance with one aspect of the invention are illustrated. A device and method creates increased functional residual capacity and upper airway patency by providing deep inspiration. In this particular embodiment, deep inspiration is provided by stimulating during a portion of an inspiration cycle. Stimulation may extend beyond the duration of an intrinsic breath. The stimulation is provided to increase tidal volume by extending the duration of the inspiration cycle. (While preferably maintaining peak flow at or near intrinsic peak flow, i.e. normalizing flow.) In accordance with a protocol, stimulation through one or more electrodes associated with the diaphragm or phrenic nerve is provided to cause the diaphragm to contract to cause a deep inspiration breath. Stimulation may be provided when a characteristic preceding an obstructive respiratory event is detected. For example, if erratic breathing occurs or if the tidal volume drops below a given threshold level, then stimulation is provided. The resulting breath comprises a deep inhalation breath (i.e., a greater tidal volume than a normal, intrinsic breath.) A deep inspiration breath may then be repeated periodically to prevent further drop in tidal volume by increasing the functional residual capacity and creating upper airway stiffening. The device may also be programmed to repeat the deep breath a given number of times before ceasing the stimulation.

One possible characteristic of breathing in obstructive sleep apnea patients is a decreasing tidal volume. The ultimate closure of an air passageway in an obstructive sleep apnea event thus may be preceded by a gradual decrease in ventilatory volume. Another possible characteristic of breathing in obstructive sleep apnea patients is an erratic breathing pattern. In a patient who is diagnosed with obstructive sleep apnea, or in other diseases, disorders or conditions, e.g. as described herein, respiration may be monitored using EMG or other sensors that sense respiration parameters corresponding to tidal volume or flow (for example, diaphragm movement which corresponds to airflow may be sensed; impedance plethysmography may be used; or flow itself may be sensed using a sensor implanted in the trachea.) FIGS. 16A-16D illustrate monitoring or detection of various aspects or parameters of respiration on a breath by breath basis. Tidal volume is monitored and a decrease in tidal volume characteristic (FIG. 4A) or an erratic breathing pattern (FIG. 4B) in an obstructive sleep apnea patient is detected. (Monitored tidal volume as used herein may also include a monitored tidal volume correlated signal). Estimated minute ventilation (i.e., determined by multiplying respiratory rate times volume of a breath) may also be used to determine the impending onset of an obstructive respiratory event.

For purposes of detecting a threshold volume on a breath-by-breath basis or in real time, a programmed threshold may be set. The threshold value may be determined when initializing the device as the value at or below which preventative or mitigating treatment is required or is otherwise optimal. This value may be programmed into the device. A minimum safety threshold value may also be established below which stimulation is inhibited to prevent airway closure. As such, the minimum safety threshold may be set as a value sufficiently above a tidal volume where stimulation treatment if provided would further close an air passageway.

When monitoring tidal volume, the area under the inspiration flow curve or EMG envelope of an individual breath may be monitored to determine tidal volume of a breath. The tidal volume is compared to a threshold value for a particular patient. Other parameters may be used to identify when tidal volume has dropped below a predetermined threshold, for example baseline tidal volume rate variance over a period of time may be monitored and compared to a normal variance. The normal variance may be determined on a patient-by-patient basis and programmed into the device.

FIG. 4A illustrates a breathing pattern where a decrease in tidal volume ultimately ends in an obstructive sleep apnea event. Accordingly, tidal volume of intrinsic breaths 411-415 of an obstructive sleep apnea patient is shown in FIG. 4A. The tidal volume of breaths 411-415 gradually decreases until the airway narrows ultimately leading to an airway obstruction. An obstructive respiratory event occurs with total airway closure after breath 415. An obstructive respiratory event may also be an airway narrowing, e.g., hypopnea. An obstructive respiratory event may be detected by monitoring a decrease in tidal volume, for example as a predetermined percentage of normal or intrinsic tidal volume. The threshold 450 below which treatment is to be provided by the device is shown in FIGS. 4A-4D. FIG. 4D illustrates a stimulation protocol corresponding to the resulting tidal volume waveforms of FIG. 4C.

FIG. 4C illustrates tidal volume of a patient treated using a deep inspiration stimulator. The stimulator detects the drop in tidal volume (breath 413) below a threshold level as described above with respect to FIGS. 4A-4B. During the subsequent breath 414, stimulation 434 (schematically illustrated as an envelope of a burst of pulses) is provided by the stimulator to provide a deep inspiration breath 424 with the breath 414. The deep inspiration breath 424 comprises a breath that has a tidal volume greater than the tidal volume of a normal or intrinsic breath. After one or more deep inspiration breath stimulations, the tidal volume is expected to return to normal or close to normal, e.g. at breaths 425-429. Synchronization is provided whereby the onset of inspiration is detected and stimulation is provided during the breath. According to one variation, a tidal volume that is greater than or equal to a predetermined percentage of a normal inspiration is detected (e.g. 10% of tidal volume as described with respect to FIGS. 16A-16E). Then when the onset of the next inspiration is detected, stimulation is provided. Additional periodic delivery of deep inspiration paced breaths may be provided synchronously or asynchronously with the intrinsic breathing, to prevent or mitigate drops in tidal volume. In accordance with this aspect of the invention, as illustrated in FIG. 4D an additional pacing pulse or burst of pulses 439 is provided to stimulate deep inspiration breath 419. Thus, the therapy described with reference to FIG. 4D may prevent a further drop in tidal volume, thereby reducing the occurrence of obstructive respiratory events or other breathing related disorders.

FIGS. 5A-5C illustrate use of a deep inspiration stimulator in accordance with the invention. FIG. 5A illustrates a breathing pattern where a decrease in tidal volume ultimately ends in an obstructive respiratory event. Accordingly, tidal volume of intrinsic breaths 511-515 of an obstructive sleep apnea patient is shown in FIG. 5A with the airway ultimately closing after breath 515. In FIG. 5A, no treatment is provided. Other pre-obstructive breathing characteristics may also be used to determine when an OSA event is likely to be imminent.

A threshold 550 below which treatment is to be provided by the device is shown in FIGS. 5A and 5B. This threshold may be determined in a manner similar to that described with respect to FIGS. 4A-4C. FIG. 5C illustrates a stimulation protocol corresponding to the resulting tidal volume waveforms of FIG. 5B. FIG. 5B illustrates the tidal volume of a patient treated using a deep inspiration stimulator who would otherwise have had a breathing pattern shown in FIG. 5A. The stimulator detects the drop in tidal volume (breath 513) below a threshold level 550 in a manner similar to that described above with respect to FIGS. 4A-4D. Prior to what would have been the subsequent breath 514, i.e., at some point during the intrinsic exhalation period or rest period, the stimulator provides stimulation 533 to elicit a deep inspiration breath 523 (FIG. 5B). The deep inspiration breath 523 comprises a breath with a tidal volume greater than the tidal volume of an intrinsic or normal breath. Preferably, the peak flow remains relatively normal while inspiration duration increases thus increasing tidal volume. After one or more deep inspiration breath stimulations, the tidal volume returns to normal, e.g., at breaths 524-525. At breaths 526,527 a slight decrease in respiratory drive is shown with a decreased tidal volume. Periodic delivery of deep inspiration breaths may be provided to prevent or mitigate drops in tidal volume. In accordance with this aspect of the invention, as illustrated in FIG. 5C an additional pacing pulse or burst of pulses 538 is provided prior to the onset of the next intrinsic breath to stimulate deep inspiration breath 528 which is then followed by a normal breath 529. The deep inspiration breaths 523 or 528 are intended to increase the functional residual capacity of the lung and/or enhance upper airway patency. Thus, the therapy may prevent further drop in tidal volume, thereby reducing the incidence of obstructive sleep apnea or other breathing related disorders.

FIGS. 6A-6B illustrate stimulation and inspiration waveforms corresponding to a variation of stimulation device and method of the invention. The stimulation protocol of FIGS. 6A-6B provides stimulation at the end of an inspiration cycle increasing inspiration duration, thereby increasing tidal volume. A resulting normalized peak flow and increased tidal volume is believed to stiffen or lengthen the upper airway and may create an upper airway hysteresis effect. Increased tidal volume may provide more time and volume for gas exchange. Among other effects, normalized peak flow and increased tidal volume are believed to prevent airway collapse attributable to obstructive sleep apnea.

FIG. 6A illustrates normal inspiration duration 610 of an intrinsic breath and increased inspiration duration 620 that would result from stimulation 650 shown in FIG. 6B. Stimulation 650 is provided at the end of an inspiration period for a predetermined amount of time $T_6$ to maintain flow and prolong inspiration for the additional period of time $T_6$. The end of the inspiration period may be determined in a manner as described with reference to FIGS. 16A-16D herein. The time $T_6$ may be selected and/or programmed into the device. The time may be determined to elicit a desired response. A short stimulation period, for example, as short as 0.1 seconds may be used.

FIGS. 7A-7B illustrate stimulation and inspiration waveforms corresponding to a variation of a stimulation device and method of the invention. The stimulation protocol of FIGS. 7A-7B provides low level stimulation at the beginning or the end of an exhalation portion of a respiration cycle, or at some time within the exhalation portion of the respiration cycle. This is believed to preserve lung volume prior to the next inspiration. The manipulation of the exhalation cycle is thus believed to increase functional residual capacity. FIG. 7A illustrates tidal volume 730 that would result from stimulation 750 shown in FIG. 7B. Stimulation 750 is provided at an end portion of an exhalation cycle to preserve some volume 740 for the next inspiration cycle thus increasing the functional residual capacity. The end of the exhalation cycle may be determined by determining the end of inspiration and then based on a known respiration rate, estimating the time of the end of the exhalation cycle. Alternatively, flow correlated respiration parameters may be sensed and the desired portion of the exhalation cycle may be determined. FIGS. 16A-16D illustrate manners for determining portions of a respiration cycle.

FIGS. 8A-8B illustrate stimulation and inspiration waveforms corresponding to a variation of a stimulation device and method or the invention. The stimulation protocol of FIG. 8B provides a low level of a continuous stimulation to cause the diaphragm to remain slightly contracted, thereby increasing functional residual capacity. FIG. 8B illustrates stimulation provided while FIG. 8A illustrates tidal volume. As shown, the tidal volume is elevated during the end portion of the exhalation cycle 840 (FIG. 8A) relative to end expiratory tidal volume before the stimulation.

Figure 9A:
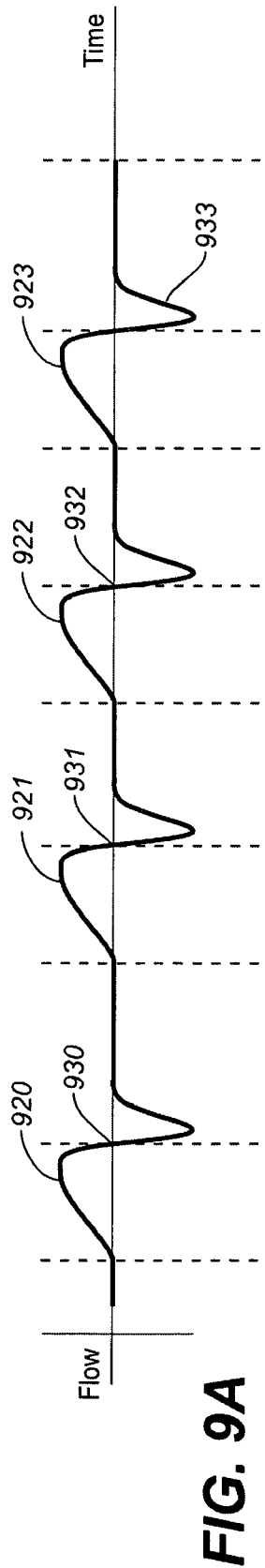
FIGS. 9A, 9B and 9C are schematic illustrations respectively of airflow, tidal volume and corresponding stimulation waveforms illustrating a stimulation method using a stimulation device in which stimulation is applied in accordance with the invention.
Figure 9B:
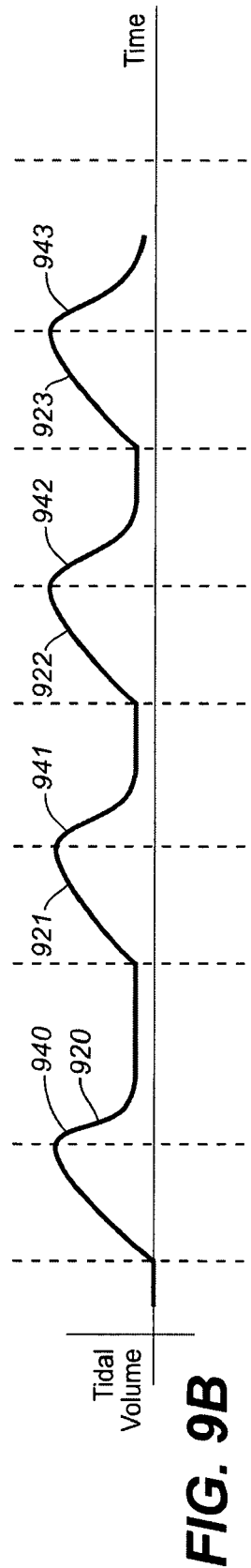
Figure 9C:
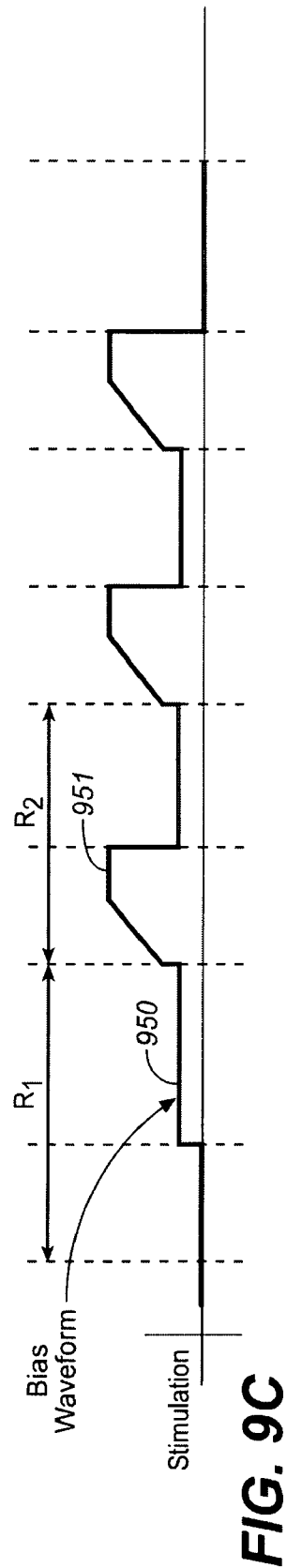

FIGS. 9A-9C illustrate stimulation and inspiration waveforms corresponding to a variation of a stimulation device and method of the invention. The stimulation protocol provides a combination of therapies or protocols including increasing functional residual capacity and controlling breathing. The stimulation protocols manipulate exhalation and control breathing. The stimulation protocol of FIGS. 9A-9C provides a low current stimulation 950 as shown in FIG. 9C during the exhalation phase of a respiration cycle and a stimulated breath 951 delivered at the end of exhalation. The stimulated breath 951 is provided at a higher rate R2 than the intrinsic rate R1. The stimulation 950 is applied between the end of inspiration cycles 920, 921, 922 and the onset of the next inspiration cycles, 921, 922, 923 respectively to increase functional residual capacity. Stimulation 951 produces inspiration cycles 920, 921, 922, 923. Flow waveforms 930, 931, 932, 933 respectively of respiration cycles 920, 921, 922, 923 are shown in FIG. 9A. Tidal volume waveforms 940, 941, 942, 943 respectively of respiration cycles 920, 921, 922, 923 are shown in FIG. 9B.

Figure 10A:
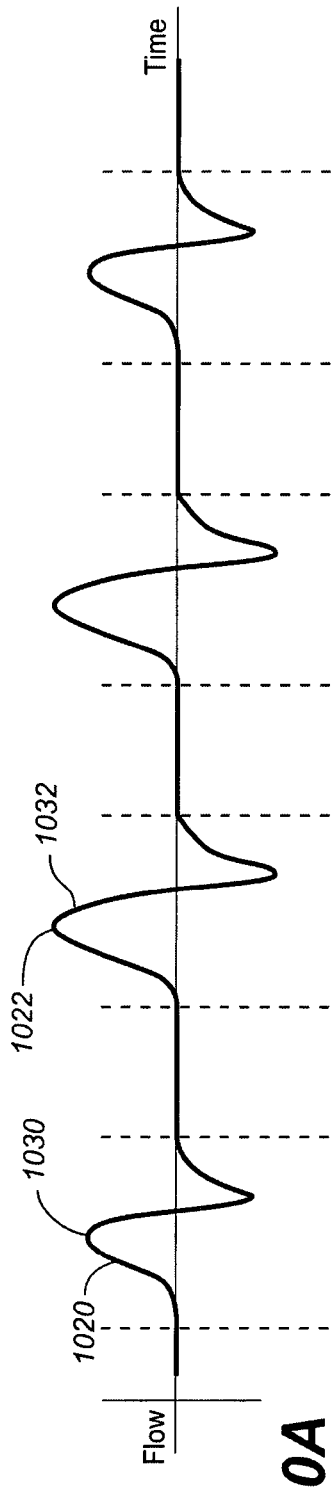
FIGS. 10A, 10B and 10C are schematic illustrations respectively of airflow, tidal volume and corresponding stimulation waveforms illustrating a stimulation method using a stimulation device in which stimulation is applied in accordance with the invention.
Figure 10B:
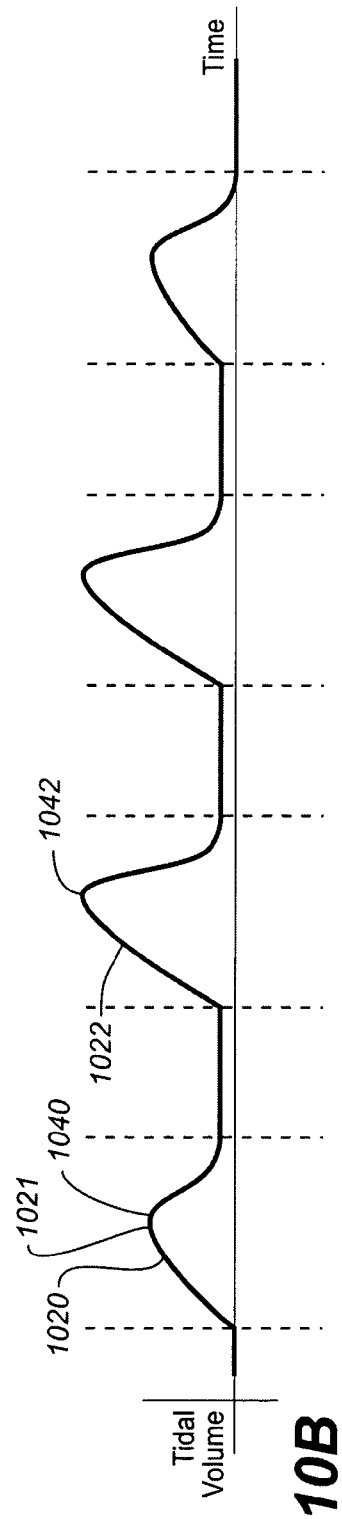
Figure 10C:
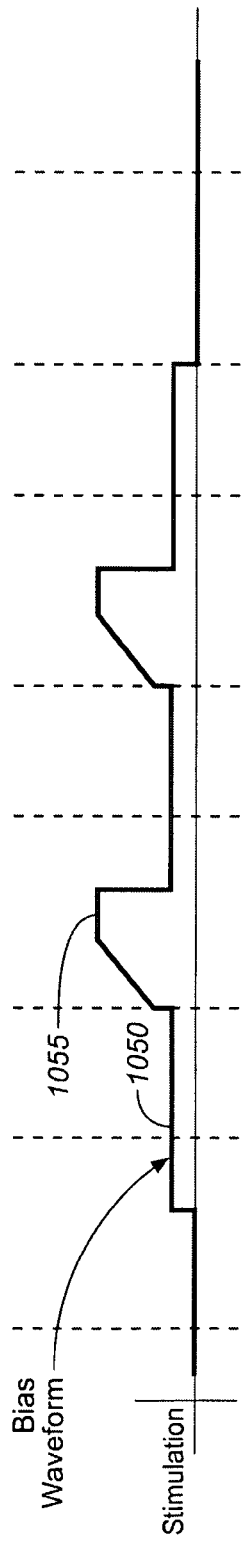

FIGS. 10A-10B illustrate stimulation and inspiration waveforms corresponding to a variation of a stimulation device and method of the invention. Stimulation is provided during the inspiration cycle in a manner shown in FIGS. 7A-7B to increase inspiration duration and tidal volume (with normalized peak flow) in order to stiffen the upper airway. Also, a low level stimulation is provided to increase lung capacity at the end of inspiration and until the beginning of the next inspiration cycle to increase the functional residual capacity. A first intrinsic respiration cycle 1020 is illustrated. At the onset of exhalation 1021 of the respiration cycle 1020, a low level stimulation 1050 is applied until the onset of the inspiration cycle of the next respiration cycle 1022. At the detection of the onset of the next respiration cycle 1022 (as described in FIGS. 16A-16E), stimulation 1055 is provided. The stimulation 1055 is applied at least in part during the inspiration cycle 1022. The corresponding tidal volumes 1040, 1042 of respiration cycles 1020, 1022 respectively are illustrated in FIG. 10A. The corresponding flows 1030, 1032 of respiration cycles 1020, 1022 respectively are shown in FIG. 10B.

Referring to FIGS. 11A and 11B, stimulation and inspiration waveforms illustrate a stimulation device and method of the invention. Stimulation is provided in a manner similar to that described with reference to FIGS. 4A-4D. In accordance with FIGS. 11A and 11B, stimulation is provided to prevent or mitigate obstructive sleep apnea by stabilizing the tidal volume. FIG. 11A schematically shows the tidal volume as sensed by EMG sensors and illustrates the intrinsic breathing 1111-1117 of a subject, as well as the resulting breathing 1124, 1125. FIG. 11B illustrates the stimulation pulse envelopes 1160 of stimulation applied to the diaphragm or phrenic nerve of a subject in accordance with one aspect of the invention. Referring to FIG. 11A, the tidal volume from intrinsic breathing gradually decreases (1111, 1112) until it falls below a threshold level 1150 (1113-1115) and then resumes normal tidal volume (1116-1117) after treatment. After breath 1113 is detected below threshold level 1150, a stimulation pulse 1160 is provided during and in synchronization with the subsequent breath 1114, 1115 to thereby provide the resulting breath. The resulting breaths have waveforms 1124, 1125 with tidal volumes increased to a level of normal breathing. According to one variation, stimulation is provided with the goal of stabilizing or normalizing breathing. After stimulating for a given period of time or number of breaths, breathing is monitored to determine if it is normalized (for example with breaths 1116, 1117) at which time the stimulation may be discontinued.

Figure 12A:
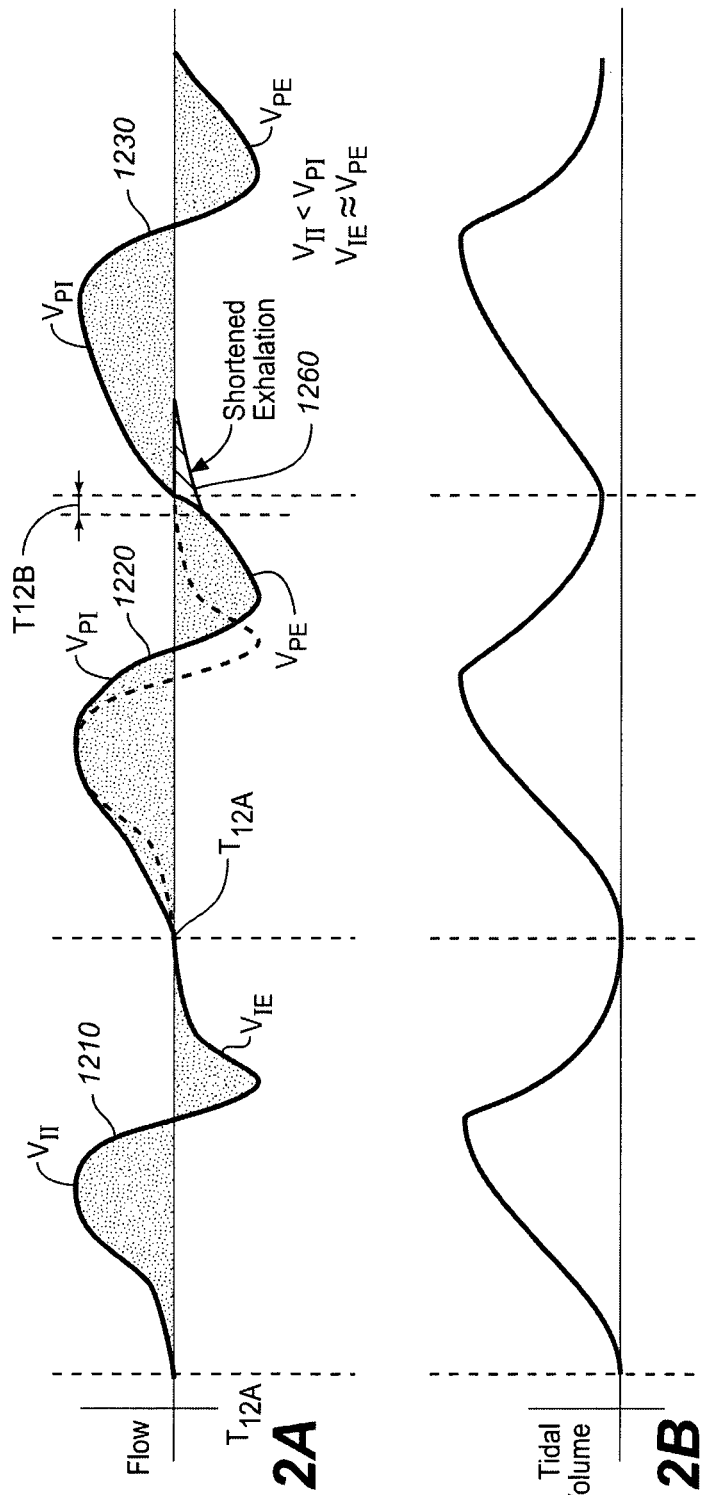
FIGS. 12A, 12B and 12C are schematic illustrations respectively of flow and tidal volume respiration response and stimulation waveforms illustrating a stimulation method using a stimulation device according to the invention.
Figure 12B:
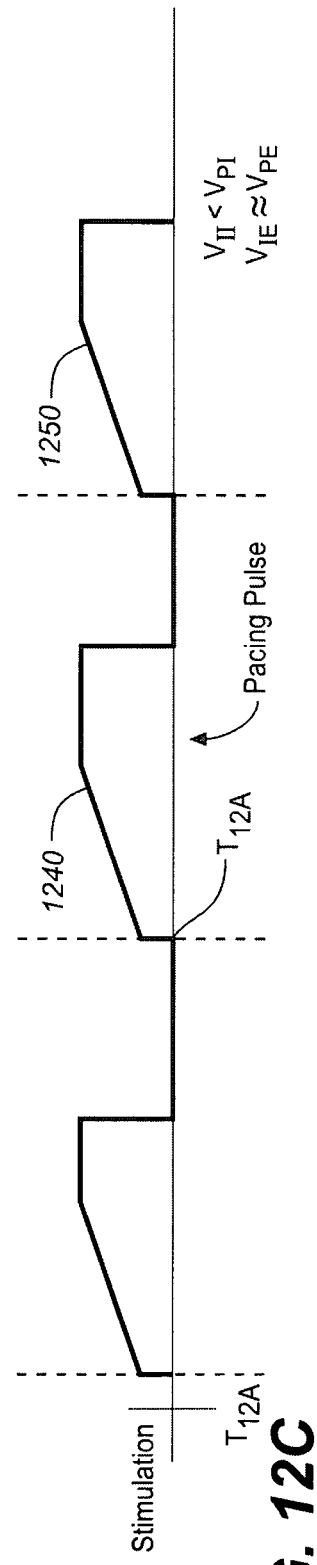
Figure 12C:
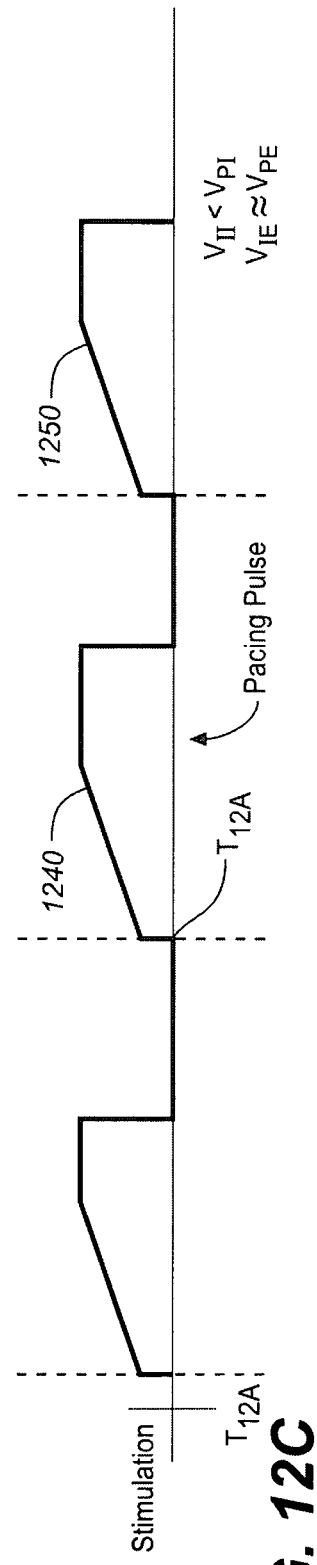

FIGS. 12A-12B illustrate stimulation and inspiration waveforms corresponding to a variation of a stimulation device and method of the invention. The stimulation protocol of FIGS. 12A-12B provides a long rising stimulation during at least the inspiration portion of a respiration cycle to increase inspiration time of the cycle with respect to expiration time (or total percentage of the cycle that corresponds to inspiration). Using breathing control therapy to lengthen the inspiratory duration, expiratory time is reduced and the baseline relaxation lung volume is not completely restored, leading to an increased functional residual capacity. The stimulation protocol thereby manipulates or shortens the length of the exhalation portion of the respiration cycle. In addition, the respiration rate is increased to shorten the exhalation portion of the respiration waveform. Thus, the protocol is directed to increasing the functional residual capacity of the lungs by manipulating the expiration phase of the respiration cycle.

FIG. 12A illustrates flow and FIG. 12B illustrates corresponding stimulation. Referring to FIG. 12A a first paced breath 1210 (with parameters like an intrinsic breath) is shown with an intrinsic inspiration volume $V_{II}$ and an intrinsic expiration volume $V_{1E}$. Prior to time $T_{12A}$, breathing may be entrained (for example, as described with respect to FIGS. 13A and 13B herein) at a rate slightly faster than the intrinsic rate but at approximately a normal tidal volume and waveform 1210. Thereafter, stimulation 1240 is applied during a rest period (i.e. at an end portion of the exhalation phase) of a respiration cycle 1220 following breath 1210. The stimulation is provided using a long rising pacing pulse so that the respiration cycle is lengthened by a time $T_{12B}$ to prevent full expiration before the next inspiration cycle of the next breath 1230 which is provided by stimulation 1250. Stimulation 1250 is provided at a rate slightly faster than the previous stimulation 1240. Thus, exhalation is shortened, preventing exhalation portion 1260, and thus increasing the functional residual capacity of the lungs.

Referring to FIGS. 13A-13B, stimulation and respiration waveforms illustrating a stimulation method using a stimulation device in accordance with one aspect of the invention are illustrated. According to FIGS. 13A-13B, breathing is stabilized by stimulating to control or manipulate breathing. FIGS. 13A-13B illustrate a variation of a technique for controlling breathing.

FIG. 13A illustrates the flow of air representing respiration waveforms over time. Breathing control may be used for a number of different purposes. It may be done with or without sensing a condition that indicates a respiratory disturbance is present or occurring. It may be done for a predetermined period of time or during certain times of day or during certain sleep cycles. It may be done to stabilize breathing.

For example, if tidal volume falls below a predetermined threshold, stimulation may begin. Stimulation may also be provided periodically or at times of greater vulnerability to obstructive sleep apnea or other disorders associated with breathing disorders. FIG. 13B illustrates envelopes 1340 of stimulation pulses provided to control breathing during the course of stimulation. FIG. 13A illustrates the breaths 1360 resulting from the stimulation illustrated in FIG. 13B.

According to this embodiment, the stimulator first takes over breathing by providing stimulation 1340 (as illustrated in FIG. 13B) at a time during an end portion 1320 of the exhalation phase of an intrinsic respiration cycle, prior to the onset of the next respiration cycle (As illustrated in FIG. 13A). The stimulation 1340 is provided at a rate greater than the intrinsic rate, i.e., where the cycle length T1 is less than the intrinsic cycle length T1+x. As illustrated the duration of the intrinsic respiration cycle is $T_1$+x. The duration of the respiration cycles of the stimulated breathing begins at $T_1$ to take over breathing. After a period of time of taking over breathing, the respiration cycle length is then gradually increased to T1+m, t1+n, and T1+o where m<n<o<x and where o approaches x in value. Breathing is thereby controlled and ventilation is accordingly stabilized.

According to one aspect of the invention, breathing is believed to be controlled by stimulating for a period of time at a rate greater than but close to the intrinsic respiratory rate. Breathing may be controlled through inhibition of the central respiratory drive or entrainment. In order to entrain breathing, stimulation may be provided until the central pattern generator activates the respiration mechanisms, which includes those of the upper airway, in phase with the stimulation through various feedback mechanisms. It is believed that breathing may be entrained when the central respiratory drive is conditioned to adapt to stimulation. When breathing is entrained, it may be possible to further slow respiration rate or the respiration cycle length so that it is longer than the intrinsic length 1320.

Some methods for controlling breathing are described for example in U.S. application Ser. No. 10/966,474, filed Oct. 15, 2004 and incorporated herein by reference.

Figure 14A:
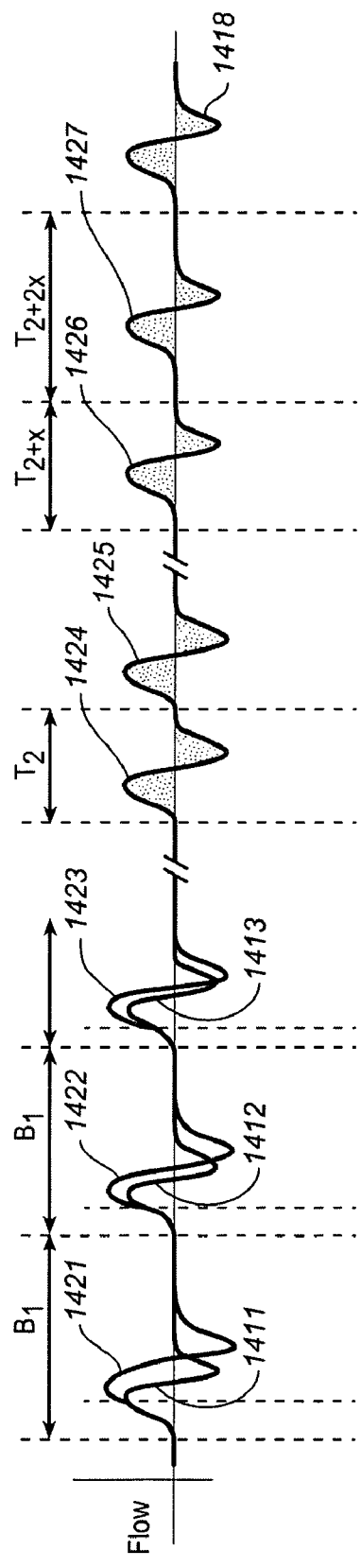
FIGS. 14A and 14B are schematic illustrations respectively of respiration response and stimulation waveforms illustrating a stimulation method using a stimulation device according to the invention.
Figure 14B:
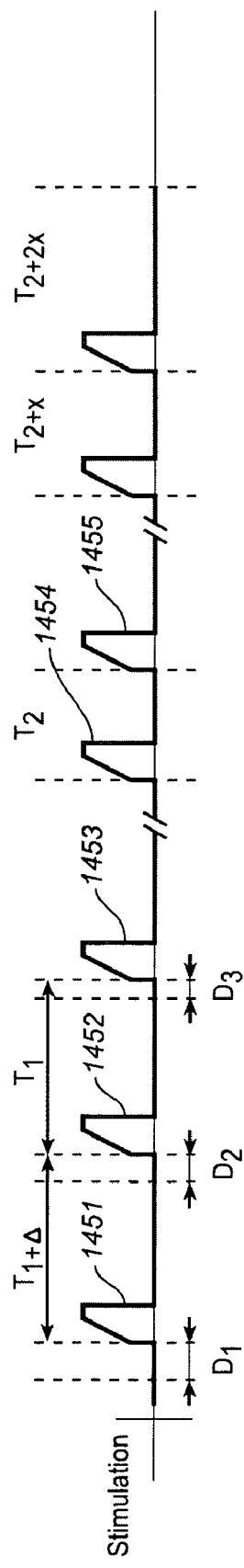

Referring to FIGS. 14A and 14B inspiration flow waveforms and stimulation pulse envelope waveforms are shown corresponding to a variation of a stimulation device and method of the invention. In accordance with this variation, the stimulation device stimulates during intrinsic breaths 1411, 1412, 1413 to provide resulting breaths 1421, 1422, 1423. The intrinsic breaths occur at a cycle length B1 (corresponding to a breathing rate) as illustrated in FIG. 14A. The first stimulation 1451 is applied at a delay D1 from the onset of intrinsic breath 1411. The next stimulation 1452 is provided at a delay D2 from the onset of intrinsic breath 1412 and the subsequent stimulation pulse 1453 is provided at a delay D3 from the onset of intrinsic breath 1413. The time between the first and second stimulation 1451 and 1452 is $T_{1+\Delta}$ a while the time between the second and third stimulation 1452 and 1453 is $T_1$, i.e., shorter. Thus stimulation is provided gradually closer and closer to the onset of inspiration to gently take over breathing with stimulation at least in part during intrinsic inspiration. The stimulation 1453 is essentially synchronous with the start of the intrinsic inspiration 1413, to create the resulting breath 1423. Stimulation may be delivered at this rate (i.e. intrinsic) for a period of time. Then the next stimulus 1454 is delivered at a rate faster than normal at a respiration cycle length timed to thereby elicit paced breath 1424. The next stimulus 1455 is delivered at the interval T2, to induce another paced breath 1425, and this may be continued for some time in order to control breathing. This may lead to the entrainment of the central respiratory control system. Also, rate may be increased gradually until no intrinsic breaths occur between the paced breaths. When control of respiratory rate is achieved (and possibly entrainment), if a slowing of the breathing rate is desired, the pacing rate can be decreased gradually as shown schematically in the Figure by stimuli delivered at a cycle length of T2+x, followed by T2+2x, inducing paced breaths 1426 and 1427. It is believed that if entrained, if desired, the stimulation rate may bring the respiration rate slower than the intrinsic rate and tidal volume may be manipulated. After a period of time or after breathing has been controlled as desired, the intrinsic breathing may be allowed to resume, for example, as shown with breath 1418. The patient may be weaned off stimulation, for example, as described herein.

In accordance with another aspect of the invention, the phrenic nerve or diaphragm may be stimulated using the low level stimulation as described herein, through an OSA event after obstructive sleep apnea event has occurred.

The stimulation described or shown herein may be comprised of several stimulation parameters. For example a burst of pulses may form a square pulse envelope or may ramp up or down in amplitude or a combination thereof. The frequencies may vary or may be varied depending upon a desired result. In accordance with one embodiment, the burst (or pulse) frequency ranges between 5-500 Hz and more preferably between 20-50 Hz. However, other frequency ranges may be used as desired. Low level pulses or continuous stimulation may comprise stimulation at about 8 mA or less or may be determined on a case-by-case basis. However, other amplitudes and frequencies may be used as desired. The stimulation may be monophasic or may be biphasic. Stimulation may be provided in response to sensing respiration or other parameters. Alternatively, stimulation may be provided periodically or during specific times, for example during sleep, during sleep stage transitions, or during non-REM sleep.

Stimulation may also be slowly phased out. That is the patients may be weaned from stimulation slowly. In general, when paced breathing is ongoing, and the therapy is to be stopped, it may be beneficial to wean the patient off the therapy to avoid creating apnea that may lead to obstructions or arousals. Weaning off would involve a gradual decrease in rate, until an intrinsic breath is detected. Once an intrinsic breath is detected, the device would discontinue pacing and would return to monitoring mode. An example of a protocol for weaning a patient off from stimulation is described, for example, in U.S. application Ser. No. 10/686,891 filed Oct. 15, 2003. Other variations of weaning patients off are also possible.

Figure 15:
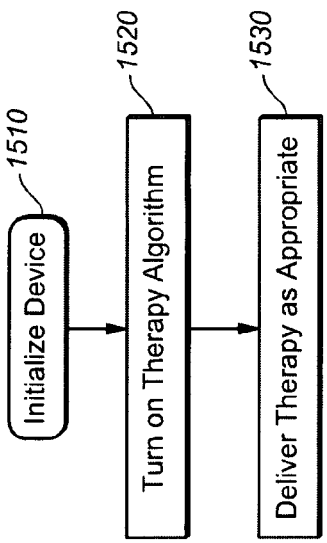
FIG. 15 is a flow chart illustrating operation of a device in accordance with the invention.

FIG. 15 is a flow chart illustrating operation of a system or device in accordance with the invention. An implanted device is initialized during an initialization period 1510. During the initialization period, among other things, the thresholds may be set up for triggering or inhibiting therapy. The thresholds may be set up by observing patient breathing over time. Therapy modalities may also be chosen, for example by testing various stimulation protocols to optimize therapy. For example, information obtained from one or more breaths can be used to set pacing parameters for subsequent therapies. Examples of data that can be obtained from one or a series of breaths include: rate, tidal volume, inspiration duration, flow parameters, peak flow, and/or duty-cycle. In the case of paced breathing therapies or breathing control (and possible entrainment), the rate of intrinsic breathing could be measured, and then paced breathing could be delivered, for example, at a faster rate than the measured rate. As another example, one could measure the inspiration duration of previous intrinsic breaths, and induce a breath to create an inspiration duration longer (or shorter) than the previous intrinsic breaths. During initialization or when updating the device, test stimulation signals and measured responses may be used to determine appropriate stimulation parameters.

During operation, the therapy is turned on 1520. This may be done automatically or manually. Therapy is delivered 1530 as is determined to be appropriate for a particular patient in accordance with one or more protocols, for example as described herein.

Referring to FIGS. 17A-17E diaphragm/phrenic nerve bias stimulation is illustrated. Optionally abdominal and chest wall stimulation may be provided in combination with diaphragm stimulation. Respiration related waveforms illustrate a stimulation device and method in accordance with the invention.

FIG. 17A illustrates the EMG envelopes 1720 corresponding to a subject's breathing. As is generally known, the EMG envelope is generally correlated to tidal volume. EMG amplitude is correlated to respiratory effort which increases during flow limitation and when no flow limitation exists is correlated to tidal volume. FIG. 17B illustrates flow or the inverse of an upper airway pressure waveform 1730 (or an other flow correlated signal). The upper airway pressure waveform may be sensed, for example using sensor 86 positioned in the mouth (epiglossal). The sensed pressure corresponds to the breathing of the subject as indicated by the EMG envelope 1720 of FIG. 17A.

A lung volume bias stimulation 1750 is applied (FIG. 17D) to the diaphragm or phrenic nerve. The bias stimulation may be provided for a predetermined period of time or on-demand, based on sensed information, for example, that indicates a greater likelihood of a respiratory disorder event occurring, for example by identifying a breathing pattern prior to onset of OSA or other disorder, or by identifying a flow limitation from an EMG. The stimulation may be provided at a level that is sufficiently low to permit intrinsic breathing to occur while stimulating. That is stimulation may be provided at a level that elicits a biased volume below or increased FRC, at or above the volume of a typical intrinsic tidal volume, provided that breathing may occur during the stimulation. The bias stimulation 1750 may be provided at or during a particular portion of an intrinsic respiration cycle. For example, the bias stimulation 1750 may be triggered at the beginning of the downward slope 1723 of the EMG envelope 1720 (FIG. 17A), at the peak 1732 of flow or inverse of upper airway pressure 1730 (FIG. 17B), or at approximately the 50% point 1743 of increasing tidal volume or inverse of intrapleural pressure 1740 (FIG. 17C). These points may be determined by analyzing the waveforms, for example, as described with respect to FIGS. 16A-16E. The bias stimulation may be provided for a predetermined period of time based on a subject's innate respiration cycle. While a specific trigger point and bias stimulation duration are described with reference to FIGS. 17A-17E, discrete bias (i.e., bias stimulation that is provided during discrete or periodic intervals, or that is timed to a particular portion of a respiration cycle) may be timed in a number of manners. The timing of the stimulation may be determined by analyzing the respiration waveform, e.g., EMG, flow, upper airway pressure, intrapleural pressure, tidal volume, or other respiration cycle correlated parameter, to determine the appropriate trigger threshold. Stimulation may also be provided a predetermined time after a trigger point is detected or determined. The bias stimulation may be initiated during a portion of an inspiration cycle, at the end of the inspiration cycle or just prior to a subsequent inspiration cycle. The bias stimulation may be provided during at least a portion of the exhalation cycle (i.e. the portion of the respiration cycle between the end of a first inspiration and the onset of the next inspiration). Bias stimulation may be triggered at or during a portion of an exhalation cycle. The system, for example may wait a percentage of an intrinsic exhalation period. This intrinsic exhalation period may be determined a number of ways. For example, the duration of an intrinsic inspiration period may be subtracted from the duration of an intrinsic respiration cycle. Alternatively, an intrinsic exhalation period may be determined by measuring the duration of one or more intrinsic expiration cycles using a flow correlated signal.

FIG. 17E illustrates a stimulation protocol of either a chest wall or abdominal muscles (muscles or associated nerves). Stimulation is provided, e.g. using electrodes 58 or 59, to augment diaphragm stimulation. A stimulation signal 1770, may be provided prior to onset of a subsequent inspiration, for example, during inspiration, at the end of inspiration or during exhalation. The stimulation may be provided to increase or supplement inspiration and/or may be used to reduce paradoxical movement of one or more of the stimulated muscles with respect to the diaphragm, that may occur during diaphragm stimulation.

A stimulation signal 1770 may be synchronized as illustrated by providing stimulation a preset period 1772 following beginning of bias stimulation 1750. A stimulation signal may also be provided at some time during an EMG envelope 1720 or at the end 1721 of and EMG envelope (FIG. 17A); during positive flow or at the beginning 1731 of negative flow of a breath or a correlated signal (FIG. 17B); or before during or after the peak 1741 of tidal volume or a correlated signal (FIG. 17C). It is believed that such stimulation may assist in controlling lung volume prior to a subsequent inspiration, or may assist in supplementing functional residual capacity. A stimulation signal 1775 may also be triggered during inspiration, e.g. at the beginning of an EMG envelope (FIG. 17A), at the beginning of positive flow or correlated signal (FIG. 17B), or at the beginning of the upward slope of tidal volume or a correlated signal (FIG. 17C). It is believed that such stimulation may augment diaphragm stimulation, or augment inspiration and/or may coordinate movement with diaphragm movement to reduce or avoid paradoxical movement with the diaphragm when providing diaphragm stimulation in accordance with one or more of the therapies, methods, devices or applications described herein.

Figures 18A, 18B, 18C:
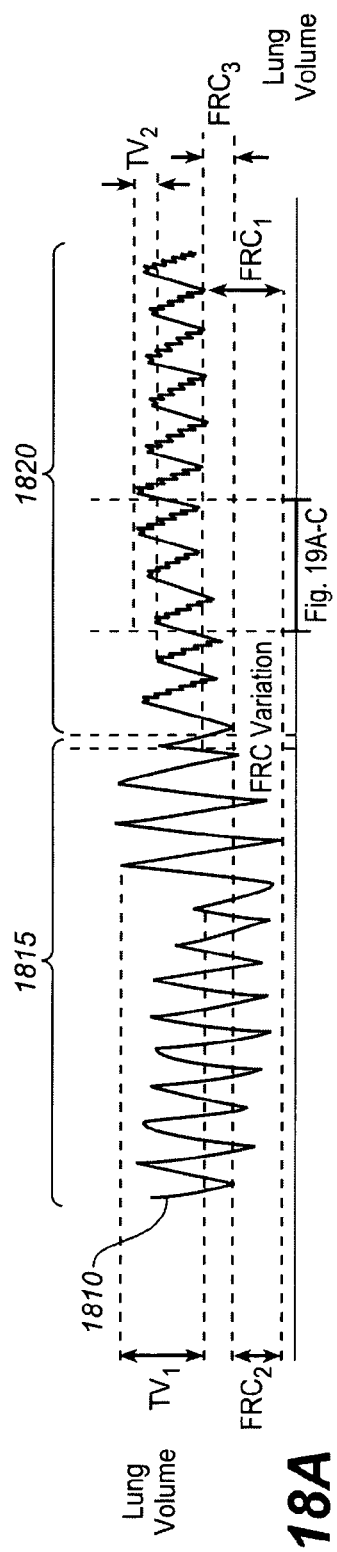
FIGS. 18A, 18B, and 18C are schematic illustrations respectively of lung volume, flow and diaphragm stimulation applied in accordance with the invention.

Referring to FIGS. 18A-18C, diaphragm and phrenic nerve stimulation and various aspects in accordance with the invention are illustrated. FIG. 18A illustrates a waveform 1810 correlated to lung volume of a subject. FIG. 18B illustrates a waveform 1830 correlated to airflow of the subject and corresponding to the waveform 1810 of FIG. 18A. FIG. 18C illustrates a stimulation signal 1860 applied to tissue of the subject to elicit a lung or diaphragm response. Portion 1815 of waveform 1810 illustrates volume during intrinsic breathing without stimulation. Portion 1820 of waveform illustrates volume during intrinsic breathing with stimulation. The stimulation is configured so that the tidal volume fluctuation V1 or a function or average thereof during intrinsic breathing is greater than tidal volume fluctuation V2 or function or average thereof when stimulation 1860 is applied. The stimulation is further configured so that the functional residual capacity FRC1 is increased when stimulation is applied. In addition the stimulation is configured so that fluctuation FRC3 of functional residual capacity (or function or average thereof) when stimulation 1860 is applied, is less than the fluctuation FRC2 of functional residual capacity (or function or average thereof) when no stimulation is applied. As shown in more detail in FIGS. 19A-19C, such stimulation is provided to elicit high frequency diaphragm contractions.

Portion 1835 of waveform 1830 illustrates flow when there is no stimulation. Portion 1840 of waveform 1830 illustrates flow when stimulation is applied during intrinsic breathing.

The stimulation is configured so that the fluctuation in peak flow F2 (or function or average thereof) when stimulation 1860 is applied, is less than the fluctuation in peak flow F1 (or function or average thereof) when there is no stimulation. Stimulation if further configured to reduce flow limitations or obstructive disorders. Breaths 1836 of portion 1835 exhibit a flattened peak flow indicating some flow limitation. Breaths 1841 of portion 1840 exhibit flow waveforms indicative of improved flow and reduced flow limitation.

FIGS. 19A-19C illustrate an enlarged view of a portion of FIGS. 18A-18C, respectively. FIG. 19A illustrates a waveform 1810 correlated to lung volume of a subject. FIG. 19B illustrates a waveform 1830 correlated to airflow of the subject and corresponding to the waveform 1810 of FIG. 19A. FIG. 19C illustrates a stimulation signal 1860 applied to tissue of the subject to elicit a diaphragm response. The stimulation is configured to increase FRC, decrease fluctuations in flow and FRC. The stimulation is further configured to provide high frequency contractions of the diaphragm to elicit high frequency changes in flow 1842. Stimulation is further configured to elicit high frequency changes in volume 1822. The stimulation signal may be provided for a duration of a plurality of breaths or only during a portion or portions of a breathing cycle such as, e.g. inspiration or exhalation or specific portions thereof. Stimulation may be configured to elicit a plurality of gas exchanges, flow or volume fluctuations during in intrinsic respiration cycle. Such plurality of gas exchanges, flow or volume fluctuations may be elicited during specific portions of a respiratory cycle, during inspiration and/or during exhalation. The stimulation may be turned on and off for period of time or triggered by an occurrence of an event.

Referring to FIGS. 20A-20D, diaphragm and phrenic nerve stimulation and various aspects in accordance with the invention are illustrated. FIG. 20A illustrates a waveform 2010 correlated to lung volume of a subject. FIG. 20B illustrates a waveform 2030 correlated to airflow of the subject and corresponding to the waveform 2010 of FIG. 20A. FIG. 20C illustrates oxygen saturation levels 2050 corresponding to respiration and stimulation shown in FIGS. 20A, 20B and 20D. FIG. 20D illustrates a stimulation signal 2060 applied to tissue of the subject to elicit a diaphragm response. Portion 2015 of waveform 2010 illustrates volume during intrinsic breathing without stimulation. Portion 2020 of waveform 2010 illustrates volume during intrinsic breathing with stimulation.

Portion 2035 of waveform 2030 illustrates flow when there is no stimulation. Portion 2040 of waveform 2030 illustrates flow when stimulation is applied during intrinsic breathing. Breathing during period 2005 of portion 2015 and of portion respectively exhibit a sudden increase in FRC (FIG. 20A) and an increase and fluctuations in peak flow (FIG. 20B) indicating arousal occurring. Breathing in portion 2020 exhibits a low variability in FRC and breathing in portion 2040 exhibits low variability in peak flow indicating a reduction in arousals.

As shown in FIG. 20C, oxygen saturation levels decrease roughly corresponding to period 2006 occurring just prior to arousal during period 2005, to a level 2057 below the desaturation threshold 2055 (about 90%). During stimulation oxygen saturation levels 2056 are above the desaturation threshold 2055.

The stimulation 2060 is configured to reduce the number or impact of arousals when stimulation is present. One measure of such arousals may include, e.g., the AHI index, arousal index, or other measures used in sleep evaluation or sleep studies.

Referring to FIGS. 21A-21D, diaphragm and phrenic nerve stimulation and various aspects in accordance with the invention are illustrated. FIG. 21A illustrates a waveform 2110 correlated to lung volume of a subject. FIG. 21B illustrates a waveform 2130 correlated to airflow of the subject and corresponding to the waveform 2110 of FIG. 21A. FIG. 21C illustrates oxygen saturation levels 2150 corresponding to respiration and stimulation shown in FIGS. 21A, 21B and 21D. FIG. 21D illustrates a stimulation signal 2160 applied to tissue of the subject to elicit a diaphragm response. Portion 2115 of waveform 2110 illustrates volume during intrinsic breathing without stimulation. Portion 2120 of waveform 2110 illustrates volume during intrinsic breathing with stimulation.

Portion 2135 of waveform 2130 illustrates flow when there is no stimulation. Portion 2140 of waveform 2130 illustrates flow when stimulation is applied during intrinsic breathing. Breathing during periods 2105 of portion 2115 and 2135 exhibit periodic breathing due to fluctuations in lung volume (FIG. 21A) and flow (21B) indicating a respiratory disturbance or disorder or a precursor to apnea. Oxygen saturation levels 2157 are below the desaturation threshold 2155 roughly during period 2105 corresponding to periodic breathing. During stimulation oxygen saturation levels 2156 are above the desaturation threshold 2155.

The stimulation 2160 is configured to treat ventilatory instability or periodic breathing or avoid the onset of apnea (with obstructive and/or central respiratory drive components). Accordingly, stimulation may be triggered by detection of unstable breathing or periodic breathing or stimulation may be provided periodically to prevent unstable or periodic breathing.

In accordance with the invention, stimulation signals 1860, 1960, 2060, and 2160 are configured, e.g., with pulse energy and frequency, to elicit twitch and sustained activation of the diaphragm muscle or contractions with both sustained and twitch components. They are configured to elicit short fast breaths or gas exchanges. They are configured to elicit high frequency breaths during intrinsic breathing. They may be configured to increase gas exchange during breathing in a damaged or diseased lung. Stimulation in a range that includes sustained and twitch contraction is believed to produce a sustained effect with a more gradual increase in FRC. The FRC may be increased over a longer period of time, e.g., over a period greater than one breathing cycle. According to another aspect of the invention stimulation is provided at a level that avoids arousals when stimulating during sleep. According to another variation stimulation energy may be tailored to elicit small twitch contractions to cause small low lung volume changes (i.e., at a tidal volume of up to about 20% of a tidal volume of an intrinsic respiration cycle). According to one variation, the stimulation signal frequency is adjusted to elicit such stimulation. The combination of pulse energy and frequency produces the desired diaphragm activation. The pulse width and amplitude of the pulses may be adjusted according to the location and method of stimulation (e.g., diaphragm or phrenic nerve).

Stimulation parameters such as amplitude, pulse width, and pulses per burst may be selected to elicit the desired response. In addition, a composite signal of a plurality of frequencies may be used. Additionally frequencies or other parameters may be selected for use based on one or more types of targeted muscle fibers to elicit a desirable diaphragm contraction.

Figure 22A:
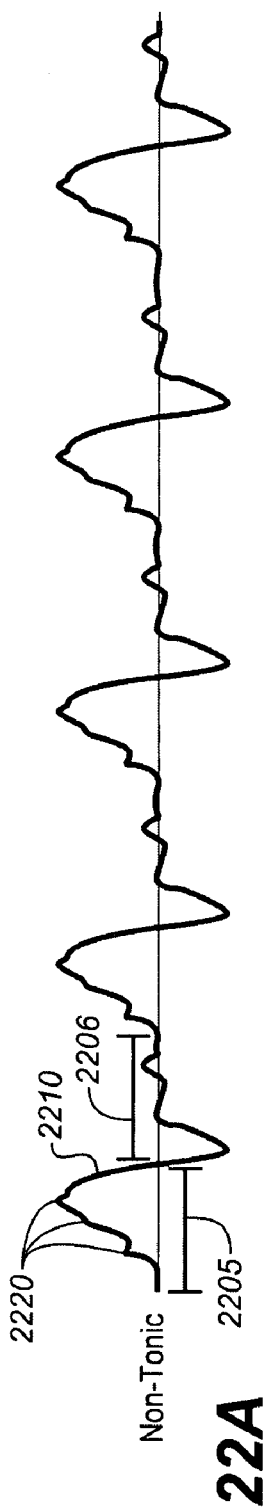
FIGS. 22A, 22B and 22C are schematic illustrations of respectively of flow, lung volume and diaphragm stimulation applied in accordance with the invention.
Figure 22B:
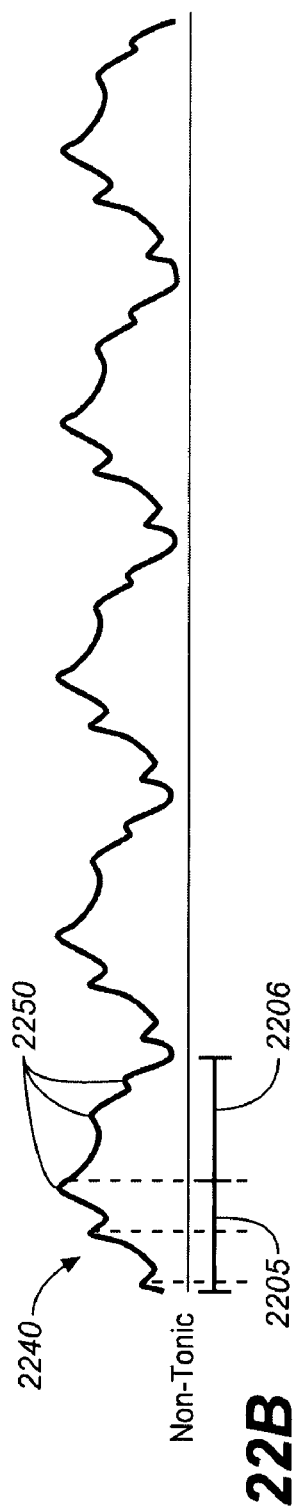
Figure 22C:
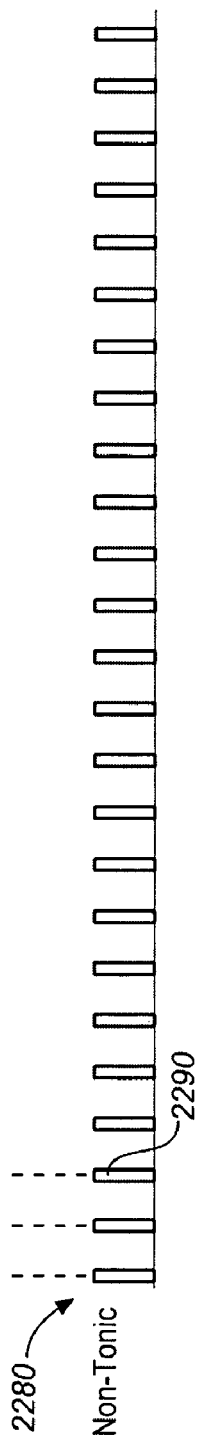

Referring to FIGS. 22A to 22C a twitch stimulation and response is illustrated. Stimulation signal 2280 shown in FIG. 22C is provided during intrinsic breathing. Flow waveform 2210 and volume waveform 2240 are shown in FIGS. 22A and 22B respectively. A twitch contraction results from each pulse 2290 of the signal 2280 resulting in small flow oscillations 2220 and small tidal volume oscillations 2250 result from each stimulation pulse of the pulse train of signal 2280. As illustrated in FIGS. 22A to 22C, a high frequency of contractions is elicited by the signal 2280 whereby a plurality of volume and/or flow oscillations occur within a breath. Stimulation may be provided during either or both of an inspiration period 2205 and an exhalation period 2206. An amplitude, pulse duration and frequency of stimulation provides sufficient energy to cause a depolarization and/or resulting sufficient muscle contraction to cause the flow or volume oscillations. However, the contractions are not sustained sufficiently to provide sustained contraction. While such pulse duration, amplitudes and frequencies vary depending on the type of stimulation provided and the construct and location of the electrodes, according to one variation, a frequency of between less than 5 Hz is provided to elicit twitch contractions.

Referring to FIGS. 23A to 23C a combined twitch and sustained stimulation and response is illustrated. Stimulation signal 2380 shown in FIG. 23C is provided during intrinsic breathing. Flow waveform 2310 and volume waveform 2340 are shown in FIGS. 23A and 23B respectively. A twitch contraction results from each pulse 2390 of the signal 2380 resulting in small flow oscillations 2320 and small tidal volume oscillations 2350 result from each stimulation pulse of the pulse train of signal 2280. In addition a degree of sustained contraction occurs whereby a sustained, gradual increase in functional residual capacity or minimum lung volume occurs during a stimulation period 2360. As further illustrated, the functional residual capacity may gradually decrease for a period 2370 after the stimulation period. However, there may be a period of normalization of breathing or ventilatory stability following stimulation. As illustrated in FIGS. 23A to 23C, a high frequency of contractions is elicited by the signal 2380 whereby a plurality of volume and/or flow oscillations occur within a breath. Stimulation may be provided during either or both of an inspiration period 2305 and an exhalation period 2306. An amplitude, pulse duration and frequency of stimulation provides sufficient energy to cause contraction with a twitch component and a sustained component. While such pulse duration, amplitudes and frequencies vary depending on the type of stimulation provided and the construct and location of the electrodes, according to one variation, a frequency of between about 3 Hz and 30 Hz is provided and more preferably between about 5 Hz and 20 Hz, to elicit twitch contractions and sustained contractions resulting in both high frequency oscillations in airflow and a slow gradual change in volume or functional residual capacity.

Referring to FIGS. 24A to 24C a sustained stimulation and response is illustrated. Stimulation signal 2480 shown in FIG. 24C is provided during intrinsic breathing. Flow waveform 2410 and volume waveform 2440 are shown in FIGS. 24A and 24B respectively. A predominantly sustained contraction occurs when stimulation is applied during intrinsic breathing whereby a sustained increase in functional residual capacity or minimum lung volume occurs. As further illustrated, the functional residual capacity generally decreases after the stimulation period. However, there may be a period of normalization of breathing or ventilatory stability following stimulation. Stimulation may be provided during either or both of an inspiration period 2405 and an exhalation period 2406. An amplitude, pulse duration and frequency of stimulation provides sufficient energy to cause a depolarization and resulting sufficient muscle contraction to cause sustained contractions. While such pulse duration, amplitudes and frequencies vary depending on the type of stimulation provided and the construction and location of the electrodes, according to one variation, a frequency of above about 20 Hz and more preferable between about 25 and 50 Hz is provided to elicit sustained contractions.

The protocols set forth herein may vary or other stimulation protocols are contemplated herein and may be used in accordance with the invention to treat respiration related disorders or other diseases, disorders or conditions.

While the invention has been exemplified with respect to treating respiratory insufficiencies and in particular, obstructive sleep apnea, various aspects of the invention are not limited to use in obstructive sleep apnea patients. Various techniques for eliciting lung or diaphragm response may be used for a variety of diseases, disorders and conditions as described herein.

For example, stimulating breathing during intrinsic inspiration may be used in numerous ways as described herein to treat a variety of diseases disorders or conditions, improve gas exchange open airway stabilize ventilation useful in any treatment involving control of breathing or ventilation. Stimulating during intrinsic inspiration may be used as a technique to gradually begin to control or manipulate breathing parameters such as breathing rate, inspiration duration and tidal volume. Stimulation during intrinsic breathing may be used with a number of breathing control protocols to initiate control of breathing, e.g., to gradually take over or to entrain breathing and to gradually control or manipulate breathing parameters. In accordance with one aspect of the invention, stimulation is provided during intrinsic breathing. In accordance with another aspect of the invention an increased or supplemental lung volume is provided over intrinsic breathing. In accordance with one aspect of the invention such supplemental lung volume comprises an increase in tidal volume with respect to existing tidal volume. In accordance with another aspect of the invention such supplemental lung volume may comprise an increased functional residual capacity (FRC) or an increased end expiratory lung volume. In accordance with another aspect of the invention a biased lung volume may be provided. In accordance with one aspect, stimulation is provided during intrinsic breathing to provide improved gas exchange.

The various techniques used to increase functional residual capacity maybe used in connection with any therapy where an increase in functional residual capacity results in a desired benefit.

Likewise, therapy described herein that stiffen the upper airway may also be used in any therapy for a breathing related disorder where the effects of improving upper airway patency are beneficial.

Similarly the techniques for controlling or entraining breathing as described herein may be used in other therapeutic applications where controlling or entraining breathing is desired.

Similarly, techniques for creating ventilatory stability as described herein may be used in other therapeutic application where stabilization is beneficial.

Similarly, the techniques for increasing or augmenting gas exchange may be used in therapeutic applications where improved gas exchange is beneficial.

Similarly, techniques for providing twitch stimulation may be used in therapeutic applications where a therapeutic benefit is provided.

Similarly techniques for providing high frequency contraction stimulation may be used in therapeutic applications where a therapeutic benefit is provided Similarly, techniques for providing low energy stimulation may be used in therapeutic application where a therapeutic benefit is provided.

Similarly, the techniques for manipulating minute ventilation may be used in therapeutic applications where a benefit is realized by controlling breathing, respiratory drive, manipulating gas exchange or improving ventilatory stability.

Stimulation may be triggered by detection of sleep disordered breathing or a precursor to sleep disordered breathing e.g. to an apnea event. Stimulation may also be provided upon detection of factors that show a general predisposition towards arousals or ventilatory instability, while such factors are not necessarily immediate precursors or predictors of imminent onset of a sleep disordered breathing event that a precursor predicts e.g. as with Cheynes-Stokes which immediately precedes apnea. According to one aspect of the invention, stimulation is provided in patients with a predisposition for sleep disordered breathing before desaturations occur or increased PCO2 levels occur to a degree that the patient's system initiates a corrective response (e.g. arousal or hyperventilation).

Stimulation may be provided at various times during sleep or various sleep stages or sleep transitions, including but not limited to, for example: prior to sleep, at sleep onset, upon detection of dropping tidal volume, upon detection of transition into REM or non-REM or during REM or non-REM sleep, or upon changes in breathing patterns, including but not limited to breathing rate.

In accordance with another aspect of the invention, diaphragm stimulation therapies described herein may be used in combination with other medical devices. Such use includes disease states where there are comorbidities with the diseases, disorders or conditions being treated with diaphragm stimulation. Also such combination may be provided where there is no connection with the other therapy but where a combination would be expeditious for the patient or reduce the number of implanted components when the devices are combined.

For example, sleep apnea often occurs in combination with other clinical conditions, which include cardiovascular disease, hypertension, diabetes, and obesity. Therefore it would be beneficial for these therapies to be provided as a component of multiple therapy system, which includes other medical device therapies. Including being in combination with, cardiac rhythm management devices, obesity control devices, and diabetes management devices. This would require either communication between two medical device controllers or one controller in communication with two different therapy delivery modules. The benefit to the patient could be a reduction in the amount of implanted hardware and electrodes, less surgical risk for device implants, better disease diagnostics, and simultaneous treatment of comorbidities, which would result in better outcomes.

The various stimulation protocols described herein may be combined in a variety of manners to achieve desired results.

While stimulation of diaphragm related nerves or muscles are described herein it is also contemplated that electrical excitation of an implanted or attached artificial muscle may be used to move the diaphragm and accordingly electrically stimulate the diaphragm as described herein is intended to include electrical excitation of such artificial muscle or excitable polymer material.

The invention claimed is:

1. A method for providing therapeutic electrical stimulation to improve gas exchange in a patient, comprising:
  identifying the patient having intrinsic respiration; and,
  applying electrical stimulation pulses targeted to diaphragm or phrenic nerve tissue of the patient at a stimulation frequency greater than a frequency of an intrinsic respiration rate at a pulse energy and frequency effective to induce a plurality of twitch contractions in the diaphragm which result in flow oscillations during a single intrinsic breath and where the flow oscillations are superimposed upon the intrinsic breath.

2. The method of claim 1 further comprising stiffening an airway of the patient prior to or while applying electrical stimulation pulses targeted to diaphragm or phrenic nerve tissue.

3. The method of claim 2 wherein stiffening an airway comprises applying an electrical stimulation to a hypoglossal nerve.

4. The method of claim 1 wherein identifying comprises identifying a patient having at least one indication selected from upper airway resistance syndrome, chronic obstructive pulmonary disease, asthma, lung injury, respiratory failure, heart failure, ventilatory instability, and sleep breathing disorders.

5. The method of claim 1 further comprising applying an electrical stimulation to open or preserve airway patency while applying electrical stimulation pulses targeted to diaphragm or phrenic nerve tissue.

6. The method of claim 1 whereby gas exchange in the patient is improved by increasing a ventilated surface area of alveoli or bronchioles in at least one lung of the patient.

7. The method of claim 1 wherein the stimulation frequency has a rate of between 10 to 150 times greater than the frequency of the intrinsic respiration rate.

8. The method of claim 1 wherein the stimulation frequency has a rate of between 15 to 50 times greater than the frequency of the intrinsic respiration rate.

9. The method of claim 1 wherein the stimulation pulses elicit non-physiologic flow characteristics from the diaphragm such that gas exchange in the patient is improved.

10. The method of claim 1 wherein applying electrical stimulation pulses contracts the diaphragm at a rate of between 3 to 15 contractions per second.

11. The method of claim 1 wherein the stimulation frequency elicits flow oscillations such that gas exchange in the patient is increased.

12. The method of claim 1 wherein applying electrical stimulation pulses further comprises normalizing or increasing a functional residual capacity of a lung volume.

13. The method of claim 1 wherein applying electrical stimulation pulses comprises applying the pulses transvenously to the diaphragm or phrenic nerve tissue.

14. The method of claim 1 wherein applying electrical stimulation pulses comprises applying the stimulation during an inspiration of the patient.

15. The method of claim 1 wherein applying electrical stimulation pulses comprises applying the stimulation during an exhalation of the patient.

16. The method of claim 1 wherein applying electrical stimulation comprises applying the stimulation at a frequency greater than a frequency of an intrinsic respiration rate whereby a functional residual capacity is sustained or increased.

17. The method of claim 16 further comprising entraining a respiration of the patient whereby the stimulation pulses are applied at a rate greater than or equal to the intrinsic respiration rate until a length of the intrinsic respiration rate is lengthened.

18. The method of claim 16 further comprising applying a deep inspiration therapy to the patient whereby the one or more breaths are stimulated to have an inspiration duration greater than an inspiration duration during intrinsic respiration.

* * * * *